United States Patent
Braun et al.

(10) Patent No.: US 12,415,786 B2
(45) Date of Patent: Sep. 16, 2025

(54) SUBSTITUTED 2-HETEROARYLAMINOBENZENES AND THE SALTS THEREOF AND THEIR USE AS HERBICIDAL AGENTS

(71) Applicant: Bayer Aktiengesellschaft, Leverkusen (DE)

(72) Inventors: Ralf Braun, Ramberg (DE); Michael Charles McLeod, Frankfurt (DE); Alexandra Manos-Turvey, Siegburg (DE); David Michael Barber, Frankfurt am Main (DE); Harald Jakobi, Frankfurt (DE); Dirk Schmutzler, Hattersheim (DE); Anu Bheemaiah Machettira, Frankfurt am Main (DE); Elisabeth Asmus, Hösbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 911 days.

(21) Appl. No.: 17/593,749

(22) PCT Filed: Mar. 23, 2020

(86) PCT No.: PCT/EP2020/057976
§ 371 (c)(1),
(2) Date: Sep. 23, 2021

(87) PCT Pub. No.: WO2020/193474
PCT Pub. Date: Oct. 1, 2020

(65) Prior Publication Data
US 2022/0169618 A1  Jun. 2, 2022

(30) Foreign Application Priority Data
Mar. 27, 2019 (EP) .................................. 19165444

(51) Int. Cl.
| | |
|---|---|
| C07D 239/42 | (2006.01) |
| A01N 25/32 | (2006.01) |
| A01N 43/40 | (2006.01) |
| A01N 43/54 | (2006.01) |
| A01P 13/00 | (2006.01) |
| C07D 213/74 | (2006.01) |
| C07D 401/12 | (2006.01) |

(52) U.S. Cl.
CPC ........... C07D 239/42 (2013.01); A01N 25/32 (2013.01); A01N 43/40 (2013.01); A01N 43/54 (2013.01); A01P 13/00 (2021.08); C07D 213/74 (2013.01); C07D 401/12 (2013.01)

(58) Field of Classification Search
CPC ........ C07D 239/42; A01P 13/00; A01N 25/32; A01N 43/40
See application file for complete search history.

(56) References Cited

U.S. PATENT DOCUMENTS

2002/0035094 A1 * 3/2002 Mantlo ..................... A61P 3/10
514/346
2011/0105472 A1   5/2011 Greul et al.

FOREIGN PATENT DOCUMENTS

| AU | 535637 B2 | 3/1984 |
|---|---|---|
| CN | 102123591 A | 7/2011 |
| CN | 106488913 A | 3/2017 |
| EP | 0008192 A1 | 2/1980 |
| EP | 0061913 A2 | 10/1982 |
| JP | 61236766 A | 10/1986 |
| WO | 2016010731 A1 | 1/2016 |

OTHER PUBLICATIONS

International Search Report mailed May 6, 2020 for PCT Application No. PCT/EP2020/057976 filed Mar. 23, 2020, 4 pages.
STN Chemical Catalog Supplier: Aurora Fine Chemicals, Registry, CAS 1410121-92-4.

* cited by examiner

Primary Examiner — Zohreh A Fay
(74) Attorney, Agent, or Firm — Paul D. Tietz; Alexandria Quezada; Gale Wesley Starkey

(57) ABSTRACT

Described are substituted 2-heteroarylaminobenzenes of the general formula (I)

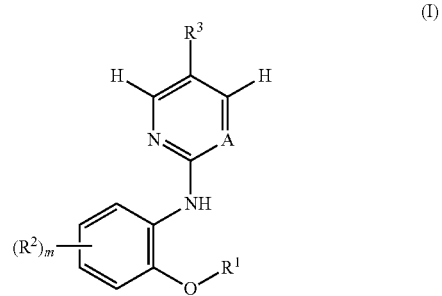

and their use as herbicides, in particular for controlling broad-leaved weeds and/or weed grasses in crops of useful plants and/or as plant growth regulators for influencing the growth of crops of useful plants. The present invention further relates to herbicidal and/or plant growth-regulating compositions comprising one or more compounds of the general formula (I).

20 Claims, No Drawings

SUBSTITUTED 2-HETEROARYLAMINOBENZENES AND THE SALTS THEREOF AND THEIR USE AS HERBICIDAL AGENTS

CROSS REFERENCE TO RELATED APPLICATIONS

This application is a national stage application under 35 U.S.C. § 371 of International Application No. PCT/EP2020/057976, filed internationally on Mar. 23, 2020, which claims the benefit of priority of European Application No. 19165444.1, filed Mar. 27, 2019.

The invention relates to the technical field of crop protection agents, in particular that of herbicides for the selective control of broad-leaved weeds and weed grasses in crops of useful plants.

Specifically, the present invention relates to substituted 2-heteroarylaminobenzenes and salts thereof, to processes for their preparation and to their use as herbicides.

In their application, crop protection agents known to date for the selective control of harmful plants in crops of useful plants or active compounds for controlling unwanted vegetation sometimes have disadvantages, be it (a) that they have no or else insufficient herbicidal activity against particular harmful plants, (b) that the spectrum of harmful plants which can be controlled with an active compound is not wide enough, (c) that their selectivity in crops of useful plants is too low and/or (d) that they have a toxicologically unfavorable profile. Furthermore, some active compounds which can be used as plant growth regulators for a number of useful plants cause unwanted reduced harvest yields in other useful plants or are not compatible with the crop plant, or only within a narrow application rate range. Some of the known active compounds cannot be produced economically on an industrial scale owing to precursors and reagents which are difficult to obtain, or they have only insufficient chemical stabilities. In the case of other active compounds, the activity is too highly dependent on environmental conditions, such as weather and soil conditions.

The herbicidal activity of these known compounds, in particular at low application rates, and/or their compatibility with crop plants remain in need of improvement.

AU535637, EP8192, EP61913, JP61236766 and WO2016/010731 describe heteroaryloxybenzenes to which a herbicidal action has been ascribed.

However, substituted 2-heteroarylaminobenzenes or salts thereof as herbicidally active compounds have hitherto not been described.

Surprisingly, it has now been found that certain substituted 2-heteroarylaminobenzenes or salts thereof are particularly suitable as herbicidally active compounds.

Accordingly, the present invention provides substituted 2-heteroarylaminobenzenes of the general formula (I) or salts thereof

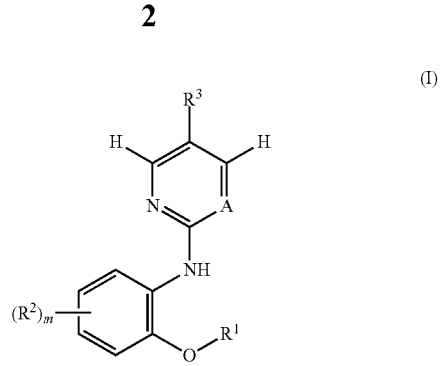

in which
A represents nitrogen or —CX—,
X represents hydrogen or halogen,
$R^1$ represents an optionally substituted aryl or heteroaryl, where each ring or each ring system is optionally substituted by up to 5 substituents independently selected from the group $R^5$,
$R^2$ independently of the others represents halogen, cyano, nitro, formyl, formamide, $(C_1-C_8)$-alkyl, $(C_1-C_8)$-haloalkyl, $(C_2-C_8)$-alkenyl, $(C_2-C_8)$-alkynyl, $(C_2-C_8)$-haloalkenyl, $(C_2-C_8)$-haloalkynyl, $(C_3-C_8)$-cycloalkyl, $(C_3-C_6)$-halocycloalkyl, $(C_3-C_6)$-cycloalkyl-$(C_1-C_6)$-alkyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, $(C_1-C_8)$-alkylcarbonyl, $(C_1-C_8)$-haloalkylcarbonyl, $(C_3-C_8)$-cycloalkylcarbonyl, carboxyl, $(C_1-C_8)$-alkoxycarbonyl, $(C_1-C_8)$-haloalkoxycarbonyl, $(C_3-C_8)$-cycloalkoxycarbonyl, carbamoyl, $(C_2-C_8)$-alkylaminocarbonyl, $(C_2-C_{10})$-dialkylaminocarbonyl, $(C_3-C_{10})$-cycloalkylaminocarbonyl, $(C_1-C_4)$-alkoxycarbonyl-$(C_1-C_4)$-alkyl, $(C_1-C_4)$-haloalkoxycarbonyl-$(C_1-C_4)$-alkyl, carboxy-$(C_1-C_4)$-alkyl, hydroxy, $NR^4R^6$, $(C_1-C_8)$-alkoxy, $(C_1-C_8)$-haloalkoxy, $(C_1-C_8)$-alkylthio, $(C_1-C_8)$-haloalkylthio, $(C_3-C_8)$-cycloalkylthio, $(C_1-C_4)$-alkoxy-$(C_1-C_4)$-alkylthio, $(C_1-C_8)$-alkylsulfinyl, $(C_1-C_8)$-haloalkylsulfinyl, $(C_3-C_8)$-cycloalkylsulfinyl, $(C_1-C_4)$-alkoxy-$(C_1-C_4)$-alkylsulfinyl, $(C_1-C_8)$-alkylsulfonyl, $(C_1-C_8)$-haloalkylsulfonyl, $(C_3-C_8)$-cycloalkylsulfonyl, $(C_1-C_4)$-alkoxy-$(C_1-C_4)$-alkylsulfonyl, $(C_1-C_8)$-alkylaminosulfonyl, $(C_2-C_8)$-dialkylaminosulfonyl or $(C_3-C_8)$-trialkylsilyl,
m represents 0, 1, 2 or 3,
$R^3$ represents hydrogen, halogen, cyano, nitro, $(C_1-C_8)$-alkyl, $(C_1-C_8)$-haloalkyl, $(C_2-C_4)$-alkenyl, $(C_2-C_4)$-alkynyl, $(C_3-C_6)$-cycloalkyl, $(C_3-C_6)$-cycloalkyl-$(C_1-C_6)$-alkyl, $(C_1-C_8)$-alkoxy, $(C_1-C_8)$-haloalkoxy, $(C_1-C_8)$-alkylthio, $(C_1-C_8)$-haloalkylthio, $(C_1-C_8)$-alkylsulfinyl, $(C_1-C_8)$-haloalkylsulfinyl, $(C_1-C_8)$-alkylsulfonyl, $(C_1-C_8)$-haloalkylsulfonyl,
$R^4$, $R^6$ independently of one another represent hydrogen, $(C_1-C_8)$-alkyl, $(C_1-C_8)$-haloalkyl, aryl-$(C_1-C_6)$-alkyl, heteroaryl-$(C_1-C_6)$-alkyl, $(C_3-C_6)$-cycloalkyl, $(C_3-C_6)$-cycloalkyl-$(C_1-C_6)$-alkyl, $(C_3-C_6)$-halocycloalkyl, $(C_3-C_6)$-halocycloalkyl-$(C_1-C_4)$-alkyl, $(C_2-C_8)$-alkenyl, $(C_2-C_8)$-alkynyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, $(C_1-C_8)$-alkylcarbonyl, $(C_1-C_8)$-haloalkylcarbonyl, $(C_3-C_8)$-cycloalkylcarbonyl, formyl, $(C_1-C_8)$-alkoxycarbonyl, $(C_1-C_8)$-haloalkoxycarbonyl, $(C_3-C_8)$-cycloalkoxycarbonyl, $(C_1-C_8)$-alkylaminocarbonyl, $(C_2-C_8)$-dialkylaminocarbonyl, $(C_3-C_8)$-cycloalkylaminocarbonyl, and $R^5$ represents hydrogen, halogen, cyano, nitro, formyl, $(C_1-C_8)$-alkyl, $(C_1-C_8)$-haloalkyl, $(C_2-C_8)$-alkenyl, $(C_2-C_8)$-alkynyl, $(C_2-C_8)$-haloalkenyl, $(C_2-C_8)$-haloalkynyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, $(C_1-C_8)$-alkylcarbonyl, $(C_1-C_8)$-haloalkylcarbonyl, $(C_3-C_8)$-cycloalkylcarbonyl, carboxyl, $(C_1-C_8)$-alkoxycarbonyl, $(C_1-C_8)$-haloalkoxycarbonyl, $(C_3-C_8)$-cycloalkoxycarbonyl, $(C_1-C_8)$-alkylaminocarbonyl, $(C_2-C_8)$-dialkylaminocarbonyl, $(C_3-C_8)$-cycloalkylaminocarbonyl, hydroxy, $(C_1-C_8)$-alkoxy, $(C_1-C_8)$-haloalkoxy, $(C_1-C_8)$-alkylthio, $(C_1-C_8)$-haloalkylthio, $(C_3-C_8)$-cycloalkylthio, $(C_1-C_8)$-alkylsulfinyl, $(C_1-C_8)$-haloalkylsulfinyl, $(C_3-C_8)$-cycloalkylsulfinyl, $(C_1-C_8)$-alkylsulfonyl, $(C_1-C_8)$-haloalkylsulfonyl, $(C_3-C_8)$-cycloalkylsulfonyl, $(C_1-C_8)$-alkylaminosulfonyl, $(C_2-C_8)$-dialkylaminosulfonyl or $(C_3-C_8)$-trialkylsilyl, except for the compounds listed below:
2-(2-phenoxyphenylamino)pyridine
5-bromo-2-(2-phenoxyphenylamino)pyridine
5-chloro-2-(2-phenoxyphenylamino)pyridine
2-(2-phenoxyphenylamino)pyrimidine
5-bromo-2-(2-phenoxyphenylamino)pyrimidine
5-iodo-2-(2-phenoxyphenylamino)pyrimidine
2-(2-(2-pyridyloxy)phenylamino)pyridine.

The compounds of the general formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts comprise the conjugate base of the acid as the anion. Suitable substituents in deprotonated form, for example sulfonic acids, particular sulfonamides or carboxylic acids, are capable of forming internal salts with groups, such as amino groups, which are themselves protonatable. Salts may also be formed by action of a base on compounds of the general formula (I). Suitable bases are, for example, organic amines such as trialkylamines, morpholine, piperidine and pyridine, and the hydroxides, carbonates and bicarbonates of ammonium, alkali metals or alkaline earth metals, especially sodium hydroxide, potassium hydroxide, sodium carbonate, potassium carbonate, sodium bicarbonate and potassium bicarbonate. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula $[NR^aR^bR^cR^d]^+$ in which $R^a$ to $R^d$ are each independently an organic radical, especially alkyl, aryl, arylalkyl or alkylaryl. Also suitable are alkylsulfonium and alkylsulfoxonium salts, such as $(C_1-C_4)$-trialkylsulfonium and $(C_1-C_4)$-trialkylsulfoxonium salts.

The substituted 2-heteroarylaminobenzenes of the general formula (I) according to the invention may, depending on external conditions such as pH, solvent and temperature, possibly be present in various tautomeric structures, all of which are embraced by the general formula (I).

The compounds of the formula (I) used in accordance with the invention and salts thereof are referred to hereinafter as "compounds of the general formula (I)".

The invention particularly preferably provides compounds of the general formula (I), in which A represents nitrogen or —CX—, X represents hydrogen or halogen, $R^1$ represents an optionally substituted aryl or heteroaryl, where each ring or each ring system is optionally substituted by up to 5 substituents independently selected from the group $R^5$, $R^2$ independently of the others represents halogen, cyano, nitro, formyl, formamide, $(C_1-C_4)$-alkyl, $(C_1-C_4)$-haloalkyl, $(C_2-C_4)$-alkenyl, $(C_2-C_4)$-alkynyl, $(C_2-C_4)$-haloalkenyl, $(C_3-C_8)$-cycloalkyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylcarbonyl, $(C_1-C_4)$-haloalkylcarbonyl, carboxyl, $(C_1-C_4)$-alkoxycarbonyl, $(C_1-C_4)$-haloalkoxycarbonyl, $(C_3-C_6)$-cycloalkoxycarbonyl, carbamoyl, $(C_2-C_4)$-alkylaminocarbonyl, $(C_2-C_6)$-dialkylaminocarbonyl, $(C_1-C_4)$-alkoxycarbonyl-$(C_1-C_4)$-alkyl, $(C_1-C_4)$-haloalkoxycarbonyl-$(C_1-C_4)$-alkyl, carboxy-$(C_1-C_4)$-alkyl, hydroxy, $NR^4R^6$, $(C_1-C_4)$-alkoxy, $(C_1-C_4)$-haloalkoxy, $(C_1-C_4)$-alkylthio, $(C_1-C_4)$-alkylsulfinyl, $(C_1-C_4)$-alkylsulfonyl, $(C_1-C_4)$-alkylaminosulfonyl, $(C_2-C_6)$-dialkylaminosulfonyl or $(C_3-C_6)$-trialkylsilyl, m represents 0, 1, 2 or 3, $R^3$ represents hydrogen, halogen, cyano, nitro, $(C_1-C_4)$-alkyl, $(C_2-C_4)$-alkenyl, $(C_2-C_4)$-alkynyl, $(C_1-C_4)$-haloalkyl, $(C_3-C_6)$-cycloalkyl, $(C_3-C_6)$-cycloalkylmethyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl, $R^4$, $R^6$ independently of one another represent hydrogen, $(C_1-C_4)$-alkyl, $(C_1-C_4)$-haloalkyl, aryl-$(C_1-C_4)$-alkyl, heteroaryl-$(C_1-C_4)$-alkyl, $(C_2-C_4)$-alkenyl, $(C_2-C_4)$-alkynyl, $(C_1-C_4)$-alkylcarbonyl, formyl or $(C_1-C_4)$-alkoxycarbonyl, and $R^5$ represents hydrogen, halogen, cyano, nitro, formyl, $(C_1-C_4)$-alkyl, $(C_1-C_4)$-haloalkyl, $(C_2-C_4)$-alkenyl, $(C_2-C_4)$-alkynyl, $(C_2-C_4)$-haloalkenyl, $(C_2-C_4)$-haloalkynyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylcarbonyl, $(C_1-C_4)$-haloalkylcarbonyl, carboxyl, $(C_1-C_4)$-alkoxycarbonyl, $(C_1-C_4)$-haloalkoxycarbonyl, $(C_3-C_6)$-cycloalkoxycarbonyl, $(C_1-C_4)$-alkylaminocarbonyl, $(C_2-C_6)$-dialkylaminocarbonyl, $(C_3-C_6)$-cycloalkylaminocarbonyl, hydroxy, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl, $(C_1-C_4)$-alkylaminosulfonyl, $(C_2-C_6)$-dialkylaminosulfonyl or $(C_3-C_6)$-trialkylsilyl, except for the compounds listed below:
2-(2-phenoxyphenylamino)pyridine
5-bromo-2-(2-phenoxyphenylamino)pyridine
5-chloro-2-(2-phenoxyphenylamino)pyridine
2-(2-phenoxyphenylamino)pyrimidine
5-bromo-2-(2-phenoxyphenylamino)pyrimidine
5-iodo-2-(2-phenoxyphenylamino)pyrimidine
2-(2-(2-pyridyloxy)phenylamino)pyridine.

The invention very particularly preferably provides compounds of the general formula (I) in which
A represents nitrogen or —CX—,
X represents hydrogen, fluorine or chlorine,
$R^1$ represents an optionally substituted phenyl, pyridyl or pyrimidyl, where each ring or each ring system is optionally substituted by up to 5 substituents independently selected from the group $R^5$,
$R^2$ independently of the others represents halogen, cyano, nitro, $(C_1$-$C_4)$-alkyl, $(C_1$-$C_4)$-haloalkyl, $NR^4R^6$, $(C_1$-$C_4)$-alkoxycarbonyl, $(C_1$-$C_4)$-alkylthio or $(C_1$-$C_4)$-alkoxy,
m represents 0, 1, 2 or 3,
$R^3$ represents hydrogen, halogen, cyano, nitro, $(C_1$-$C_4)$-alkyl, $(C_1$-$C_4)$-haloalkyl, $(C_2$-$C_4)$-alkenyl, $(C_2$-$C_4)$-alkynyl, $(C_2$-$C_4)$-haloalkenyl, $(C_2$-$C_4)$-haloalkynyl, cyclopropyl, cyclopropylmethyl, $(C_1$-$C_4)$-alkoxy, $(C_1$-$C_4)$-haloalkoxy, $(C_1$-$C_4)$-alkylthio or $(C_1$-$C_4)$-haloalkylthio,
$R^4$, $R^6$ independently of one another represent hydrogen, $(C_1$-$C_4)$-alkyl, $(C_1$-$C_4)$-alkylcarbonyl or $(C_1$-$C_4)$-alkoxycarbonyl,
and
$R^5$ represents hydrogen, halogen, cyano, $(C_1$-$C_4)$-alkyl, $(C_1$-$C_4)$-haloalkyl, $(C_1$-$C_4)$-alkylthio, $(C_1$-$C_4)$-alkoxy or $(C_1$-$C_4)$-haloalkoxy,
except for the compounds listed below:
2-(2-phenoxyphenylamino)pyridine
5-bromo-2-(2-phenoxyphenylamino)pyridine
5-chloro-2-(2-phenoxyphenylamino)pyridine
2-(2-phenoxyphenylamino)pyrimidine
5-bromo-2-(2-phenoxyphenylamino)pyrimidine
5-iodo-2-(2-phenoxyphenylamino)pyrimidine
2-(2-(2-pyridyloxy)phenylamino)pyridine.

The invention likewise further preferably provides compounds of the general formula (I), in which
A represents nitrogen or —CX—,
X represents hydrogen, fluorine or chlorine,
$R^1$ represents an optionally substituted phenyl, pyridyl or pyrimidyl, where each ring or each ring system is optionally substituted by up to 5 substituents independently selected from the group $R^5$,
$R^2$ independently of the others represents halogen, cyano, nitro, $(C_1$-$C_4)$-alkyl, $(C_1$-$C_4)$-haloalkyl, $(C_1$-$C_4)$-alkoxycarbonyl, $(C_1$-$C_4)$-alkylthio, $NR^4R^6$ or $(C_1$-$C_4)$-alkoxy,
m represents 0, 1, 2 or 3,
$R^3$ represents hydrogen, halogen, cyano, $(C_1$-$C_4)$-alkyl, $(C_1$-$C_4)$-haloalkyl, cyclopropyl, cyclopropylmethyl, $(C_1$-$C_4)$-alkoxy, $(C_1$-$C_4)$-haloalkoxy, $(C_1$-$C_4)$-alkylthio or $(C_1$-$C_4)$-haloalkylthio,
$R^4$, $R^6$ independently of one another represent hydrogen or methyl, and
$R^5$ represents hydrogen, halogen, cyano, $(C_1$-$C_4)$-alkyl, $(C_1$-$C_4)$-haloalkyl, $(C_1$-$C_4)$-alkylthio, $(C_1$-$C_4)$-alkoxy or $(C_1$-$C_4)$-haloalkoxy,
except for the compounds listed below:
2-(2-phenoxyphenylamino)pyridine
5-bromo-2-(2-phenoxyphenylamino)pyridine
5-chloro-2-(2-phenoxyphenylamino)pyridine
2-(2-phenoxyphenylamino)pyrimidine
5-bromo-2-(2-phenoxyphenylamino)pyrimidine
5-iodo-2-(2-phenoxyphenylamino)pyrimidine
2-(2-(2-pyridyloxy)phenylamino)pyridine.

The invention likewise further preferably provides compounds of the general formula (I), in which
A represents nitrogen or —CX—,
X represents hydrogen, fluorine or chlorine,
$R^1$ represents an optionally substituted phenyl, pyridyl or pyrimidyl, where each ring is optionally substituted by up to 5 substituents independently of one another selected from the group $R^5$,
$R^2$ independently of the others represents fluorine, chlorine, bromine, cyano, nitro, methyl, ethyl, trifluoromethyl, methoxy, methylthio or amino,
m represents 0, 1, 2 or 3,
$R^3$ represents hydrogen, fluorine, chlorine, bromine, cyano, nitro, methyl, ethyl, trifluoromethyl, methoxy, trifluoromethoxy, methylthio or trifluoromethylthio,
and
$R^5$ represents hydrogen, fluorine, chlorine, bromine, cyano, methyl, trifluoromethyl, methoxy or trifluoromethoxy,
except for the compounds listed below:
2-(2-phenoxyphenylamino)pyridine
5-bromo-2-(2-phenoxyphenylamino)pyridine
5-chloro-2-(2-phenoxyphenylamino)pyridine
2-(2-phenoxyphenylamino)pyrimidine
5-bromo-2-(2-phenoxyphenylamino)pyrimidine
5-iodo-2-(2-phenoxyphenylamino)pyrimidine
2-(2-(2-pyridyloxy)phenylamino)pyridine.

The definitions of radicals listed above in general terms or within areas of preference apply both to the end products of the general formula (I) and correspondingly to the starting materials or intermediates required for preparation in each case. These radical definitions can be combined with one another as desired, i.e. including combinations between the given preferred ranges.

Primarily for reasons of higher herbicidal activity, better selectivity and/or better producibility, inventive compounds of the abovementioned general formula (I) or their salts or their use according to the invention are of particular interest in which individual radicals have one of the preferred meanings already specified or specified below, or in particular those in which one or more of the preferred meanings already specified or specified below occur in combination.

With regard to the compounds according to the invention, the terms used above and further below will be elucidated. These are familiar to the person skilled in the art and especially have the definitions elucidated hereinafter:

Unless defined differently, names of chemical groups are generally to be understood such that attachment to the skeleton or the remainder of the molecule is via the structural element of the relevant chemical group mentioned last, i.e. for example in the case of $(C_2$-$C_8)$-alkenyloxy via the oxygen atom and in the case of heteroaryl-$(C_1$-$C_6)$-alkyl or $(C_1$-$C_4)$-alkylthio-$(C_1$-$C_4)$-alkyl in each case via the carbon atom of the alkyl group.

According to the invention, "alkylsulfonyl"—alone or as part of a chemical group—refers to straight-chain or branched alkylsulfonyl, preferably having 1 to 8 or 1 to 6 carbon atoms, for example (but not limited to) $(C_1$-$C_6)$-alkylsulfonyl such as methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

According to the invention, "alkylthio"—alone or as part of a chemical group—refers to straight-chain or branched S-alkyl, preferably having 1 to 8 or 1 to 6 carbon atoms, such as $(C_1-C_{10})$-, $(C_1-C_6)$- or $(C_1-C_4)$-alkylthio, for example (but not limited to) $(C_1-C_6)$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio.

According to the invention, "alkylsulfinyl (alkyl-S(=O)—)", unless defined differently elsewhere, denotes alkyl radicals which are bonded to the skeleton via —S(=O)—, such as $(C_1-C_{10})$-, $(C_1-C_6)$- or $(C_1-C_4)$-alkylsulfinyl, for example (but not limited to) $(C_1-C_6)$-alkylsulfinyl such as methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl.

"Alkoxy" denotes an alkyl radical attached via an oxygen atom, for example (but not limited to) $(C_1-C_6)$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Alkenyloxy denotes an alkenyl radical attached via an oxygen atom, and alkynyloxy denotes an alkynyl radical attached via an oxygen atom, such as $(C_2-C_{10})$-, $(C_2-C_6)$- or $(C_2-C_4)$-alkenoxy and $(C_3-C_{10})$-, $(C_3-C_6)$- or $(C_3-C_4)$-alkynoxy.

According to the invention, "alkylcarbonyl" (alkyl-C(=O)—), unless defined differently elsewhere, represents alkyl radicals bonded to the skeleton via —C(=O)—, such as $(C_1-C_{10})$-, $(C_1-C_6)$- or $(C_1-C_4)$-alkylcarbonyl. Here, the number of the carbon atoms refers to the alkyl radical in the alkylcarbonyl group.

"Alkoxycarbonyl (alkyl-O—C(=O)—)", unless defined differently elsewhere: alkyl radicals bonded to the skeleton via —O—C(=O)—, such as $(C_1-C_{10})$-, $(C_1-C_6)$- or $(C_1-C_4)$-alkoxycarbonyl. Here, the number of the carbon atoms refers to the alkyl radical in the alkoxycarbonyl group. Analogously, "alkenyloxycarbonyl" and "alkynyloxycarbonyl", unless defined differently elsewhere, in accordance with the invention, respectively represent alkenyl and alkynyl radicals bonded to the skeleton via —O—C(=O)—, such as $(C_2-C_{10})$-, $(C_2-C_6)$- or $(C_2-C_4)$-alkenyloxycarbonyl and $(C_3-C_{10})$-, $(C_3-C_6)$- or $(C_3-C_4)$-alkynyloxycarbonyl. Here, the number of the carbon atoms refers to the alkenyl or alkynyl radical in the alkenyloxycarbonyl or alkynyloxycarbonyl group.

The term "aryl" denotes an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

When a base structure is substituted "by one or more radicals" from a list of radicals (=group) or a generically defined group of radicals, this in each case includes simultaneous substitution by a plurality of identical and/or structurally different radicals.

According to the invention, the expression "heteroaryl" refers to heteroaromatic compounds, i.e. fully unsaturated aromatic heterocyclic compounds, preferably 5- to 7-membered rings having 1 to 4, preferably 1 or 2, identical or different heteroatoms, preferably O, S or N. Inventive heteroaryls are, for example, 1H-pyrrol-1-yl; 1H-pyrrol-2-yl; 1H-pyrrol-3-yl; furan-2-yl; furan-3-yl; thien-2-yl; thien-3-yl, 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl, 2H-1,2,3,4-tetrazol-5-yl, 1H-1,2,3,4-tetrazol-5-yl, 1,2,3,4-oxatriazol-5-yl, 1,2,3,4-thiatriazol-5-yl, 1,2,3,5-oxatriazol-4-yl, 1,2,3,5-thiatriazol-4-yl. The heteroaryl groups of the invention may also be substituted by one or more identical or different radicals. If two adjacent carbon atoms are part of a further aromatic ring, the systems are fused heteroaromatic systems, such as benzofused or polyannelated heteroaromatics. Preferred examples are quinolines (e.g. quinolin-2-yl, quinolin-3-yl, quinolin-4-yl, quinolin-5-yl, quinolin-6-yl, quinolin-7-yl, quinolin-8-yl); isoquinolines (e.g. isoquinolin-1-yl, isoquinolin-3-yl, isoquinolin-4-yl, isoquinolin-5-yl, isoquinolin-6-yl, isoquinolin-7-yl, isoquinolin-8-yl); quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazines; pyridopyrimidines; pyridopyridazines; pteridines; pyrimidopyrimidines. Examples of heteroaryl are also 5- or 6-membered benzofused rings from the group of 1H-indol-1-yl, 1H-indol-2-yl, 1H-indol-3-yl, 1H-indol-4-yl, 1H-indol-5-yl, 1H-indol-6-yl, 1H-indol-7-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, 2H-indazol-7-yl, 2H-isoindol-2-yl, 2H-isoindol-1-yl, 2H-isoindol-3-yl, 2H-isoindol-4-yl, 2H-isoindol-5-yl, 2H-isoindol-6-yl; 2H-isoindol-7-yl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,2-benzisoxazol-3-yl, 1,2-benzisoxazol-4-yl, 1,2-benzisoxazol-5-yl, 1,2-benzisoxazol-6-yl, 1,2-benzisoxazol-7-yl, 1,2-benzisothiazol-3-yl, 1,2-benzisothiazol-4-yl, 1,2-benzisothiazol-5-yl, 1,2-benzisothiazol-6-yl, 1,2-benzisothiazol-7-yl.

The term "halogen" denotes, for example, fluorine, chlorine, bromine or iodine. If the term is used for a radical, "halogen" denotes, for example, a fluorine, chlorine, bromine or iodine atom.

According to the invention, "alkyl" means a straight-chain or branched open-chain, saturated hydrocarbon radical which is optionally mono- or polysubstituted, and in the latter case is referred to as "substituted alkyl". Preferred substituents are halogen atoms, alkoxy, haloalkoxy, cyano, alkylthio, haloalkylthio, amino or nitro groups, particular preference being given to methoxy, methyl, fluoroalkyl, cyano, nitro, fluorine, chlorine, bromine or iodine. The prefix "bis" also includes the combination of different alkyl radicals, e.g. methyl(ethyl) or ethyl(methyl).

"Haloalkyl", "-alkenyl" and "-alkynyl" respectively denote alkyl, alkenyl and alkynyl partially or fully substituted by identical or different halogen atoms, for example monohaloalkyl such as $CH_2CH_2Cl$, $CH_2CH_2Br$, $CHClCH_3$, $CH_2Cl$, $CH_2F$; perhaloalkyl such as $CCl_3$, $CClF_2$, $CFCl_2$, $CF_2CClF_2$, $CF_2CClFCF_3$; polyhaloalkyl such as $CH_2CHFCl$, $CF_2CClFH$, $CF_2CBrFH$, $CH_2CF_3$; the term perhaloalkyl also encompasses the term perfluoroalkyl.

"Haloalkoxy" is, for example, $OCF_3$, $OCHF_2$, $OCH_2F$, $OCF_2CF_3$, $OCH_2CF_3$ and $OCH_2CH_2Cl$; this applies correspondingly to haloalkenyl and other halogen-substituted radicals.

The expression "$(C_1-C_4)$-alkyl" mentioned here by way of example is a brief notation for straight-chain or branched alkyl having one to 4 carbon atoms according to the range stated for carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals with a greater number of carbon atoms, i.e. according to the example also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbon radicals such as alkyl, alkenyl and alkynyl radicals, including in composite radicals. Alkyl radicals, including in composite radicals such as alkoxy, haloalkyl, etc., are, for example, methyl, ethyl, n-propyl or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals, where at least one double bond or triple bond is present. Preference is given to radicals having one double bond or triple bond.

The term "alkenyl" also includes, in particular, straight-chain or branched open-chain hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl denotes, for example, vinyl which may optionally be substituted by further alkyl radicals, for example (but not limited thereto) $(C_2-C_6)$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "alkynyl" also includes, in particular, straight-chain or branched open-chain hydrocarbon radicals having more than one triple bond, or else having one or more triple bonds and one or more double bonds, for example 1,3-butatrienyl or 3-penten-1-yn-1-yl. $(C_2-C_6)$-Alkynyl denotes, for example, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

The term "cycloalkyl" refers to a carbocyclic saturated ring system having preferably 3-8 ring carbon atoms, for example cyclopropyl, cyclobutyl, cyclopentyl or cyclohexyl, which optionally has further substitution, preferably by hydrogen, alkyl, alkoxy, cyano, nitro, alkylthio, haloalkylthio, halogen, alkenyl, alkynyl, haloalkyl, amino, alkylamino, bisalkylamino, alkoxycarbonyl, hydroxycarbonyl, arylalkoxycarbonyl, aminocarbonyl, alkylaminocarbonyl, cycloalkylaminocarbonyl. In the case of optionally substituted cycloalkyl, cyclic systems with substituents are included, also including substituents with a double bond on the cycloalkyl radical, for example an alkylidene group such as methylidene. In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl and adamantan-2-yl, but also systems such as 1,1'-bi(cyclopropyl)-1-yl, 1,1'-bi(cyclopropyl)-2-yl, for example. The term "$(C_3-C_7)$-cycloalkyl" is a brief notation for cycloalkyl having three to 7 carbon atoms, corresponding to the range specified for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl.

"Arylalkyl" represents an aryl radical attached via an alkyl group and "heteroarylalkyl" represents a heteroaryl radical attached via an alkyl group.

According to the invention, "haloalkylthio"—on its own or as constituent part of a chemical group—represents straight-chain or branched S-haloalkyl, preferably having 1 to 8, or having 1 to 6 carbon atoms, such as $(C_1-C_8)$-, $(C_1-C_6)$- or $(C_1-C_4)$-haloalkylthio, for example (but not limited thereto) trifluoromethylthio, pentafluoroethylthio, difluoromethyl, 2,2-difluoroeth-1-ylthio, 2,2,2-difluoroeth-1-ylthio, 3,3,3-prop-1-ylthio.

"Halocycloalkyl" denotes cycloalkyl which is partially or fully substituted by identical or different halogen atoms, such as F, Cl and Br, or by haloalkyl, such as trifluoromethyl or difluoromethyl, for example 1-fluorocycloprop-1-yl, 2-fluorocycloprop-1-yl, 2,2-difluorocycloprop-1-yl, 1-fluorocyclobut-1-yl, 1-trifluoromethylcycloprop-1-yl, 2-trifluoromethylcycloprop-1-yl, 1-chlorocycloprop-1-yl, 2-chlorocycloprop-1-yl, 2,2-dichlorocycloprop-1-yl, 3,3-difluorocyclobutyl.

According to the invention, "trialkylsilyl"—on its own or as constituent part of a chemical group—represents straight-chain or branched Si-alkyl, preferably having 1 to 8, or having 1 to 6 carbon atoms, such as tri[$(C_1-C_8)$-, $(C_1-C_6)$- or $(C_1-C_4)$-alkyl]silyl, for example (but not limited thereto) trimethylsilyl, triethylsilyl, tri(n-propyl)silyl, tri(isopropyl)silyl, tri(n-butyl)silyl, tri(1-methylprop-1-yl)silyl, tri(2-methylprop-1-yl)silyl, tri(1,1-dimethyleth-1-yl)silyl, tri(2,2-dimethyleth-1-yl)silyl.

If the compounds can form, through a hydrogen shift, tautomers whose structure is not formally covered by the general formula (I), these tautomers are nevertheless covered by the definition of the compounds of the general formula (I) according to the invention, unless a particular tautomer is under consideration. For example, many carbonyl compounds may be present both in the keto form and in the enol form, both forms being encompassed by the definition of the compound of the general formula (I).

Depending on the nature of the substituents and the manner in which they are attached, the compounds of the general formula (I) may be present as stereoisomers. The possible stereoisomers defined by the specific three-dimensional form thereof, such as enantiomers, diastereomers, Z and E isomers, are all encompassed by the general formula (I). If, for example, one or more alkenyl groups are present, diastereomers (Z and E isomers) may occur. If, for example, one or more asymmetric carbon atoms are present, enantiomers and diastereomers may occur. Stereoisomers can be obtained from the mixtures obtained in the preparation by customary separation methods. The chromatographic separation can be effected either on the analytical scale to find the enantiomeric excess or the diastereomeric excess, or else on the preparative scale to produce test specimens for biological testing. It is likewise possible to selectively prepare stereoisomers by using stereoselective reactions with use of optically active starting materials and/or auxiliaries. The invention thus also relates to all stereoisomers which are embraced by the general formula (I) but are not shown in their specific stereometric form, and to mixtures thereof.

If the compounds are obtained as solids, the purification can also be carried out by recrystallization or digestion. If individual compounds (I) cannot be obtained in a satisfactory manner by the routes described below, they can be prepared by derivatization of other compounds (I).

Suitable isolation methods, purification methods and methods for separating stereoisomers of compounds of the general formula (I) are methods generally known to the person skilled in the art from analogous cases, for example by physical processes such as crystallization, chromatographic methods, in particular column chromatography and HPLC (high pressure liquid chromatography), distillation, optionally under reduced pressure, extraction and other methods, any mixtures that remain can generally be separated by chromatographic separation, for example on chiral solid phases. Suitable for preparative amounts or on an industrial scale are processes such as crystallization, for example of diastereomeric salts which can be obtained from the diastereomer mixtures using optically active acids and, if appropriate, provided that acidic groups are present, using optically active bases.

The present invention also claims processes for preparing the compounds of the general formula (I) according to the invention.

The compounds of the general formula (I) according to the invention can be prepared, inter alia, using known processes. The synthesis routes used and examined proceed from commercially available or easily preparable building blocks. In the schemes which follow, the moieties X, A, $R^1$, $R^2$, $R^3$ and m of the general formula (I) have the meanings defined above, unless illustrative but non-limiting definitions are given.

Compounds according to the invention can be prepared, for example, by the method specified in scheme 1.

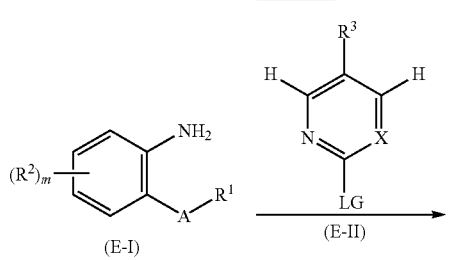

Scheme 1.

-continued

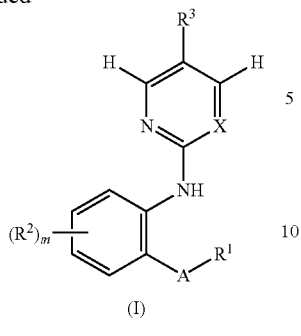

The pyri(mi)dines of the general formula (I) can be prepared by coupling the corresponding anilines (E-I) with the pyri(mi)dines (EII), where LG represents a leaving group, in the presence of, for example, a palladium catalyst. The required base may, for example, be a carbonate salt of an alkali metal (for example sodium or potassium). The reactions are generally conducted in an organic solvent, for example dioxane, dimethyl sulfoxide or dimethylformamide, at temperatures between 0° C. and the boiling point of the solvent.

Anilines of the general formula (E-I) are known from the literature and can be prepared, for example, according to the methods described in Organic Letters, 19(14), 3855-3858; 2017 and similar methods.

Selected detailed synthesis examples for the compounds of the general formula (I) according to the invention are given below. The $^1$H NMR, $^{13}$C-NMR and $^{19}$F-NMR spectroscopy data reported for the chemical examples described in the sections which follow (400 MHz for $^1$H NMR and 150 MHz for $^{13}$C-NMR and 375 MHz for $^{19}$F-NMR, solvent CDCl$_3$, CD$_3$OD or d$_6$-DMSO, internal standard: tetramethylsilane δ=0.00 ppm) were obtained on a Bruker instrument, and the signals listed have the meanings given below: br=broad; s=singlet, d=doublet, t=triplet, dd=doublet of doublets, ddd=doublet of a doublet of doublets, m=multiplet, q=quartet, quint=quintet, sext=sextet, sept=septet, dq=doublet of quartets, dt=doublet of triplets. In the case of diastereomer mixtures, either the significant signals for each of the two diastereomers are reported or the characteristic signal of the main diastereomer is reported. The abbreviations used for chemical groups have, for example, the following meanings: Me=CH$_3$, Et=CH$_2$CH$_3$, t-Hex=C(CH$_3$)$_2$CH(CH$_3$)$_2$, t-Bu=C(CH$_3$)$_3$, n-Bu=unbranched butyl, n-Pr=unbranched propyl, i-Pr=branched propyl, c-Pr=cyclopropyl, c-Hex=cyclohexyl.

SYNTHESIS EXAMPLES

Table Example Number 1-246

Synthesis Step 1: 2-(2-Fluorophenoxy)-3-nitrobenzonitrile

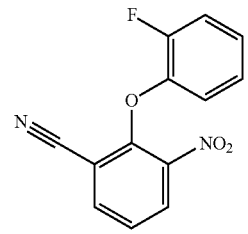 [SMILES: N#Cc1cccc([N+](=O)[O-])c1Oc1ccccc1F]

A solution of 741 mg of 2-fluoro-3-nitrobenzonitrile (4.46 mmol, 1.0 eq), 500 mg of 2-fluorophenol (4.46 mmol, 1.0 eq) and 1.23 g of potassium carbonate (8.92 mmol, 2.0 eq) in 10 ml of DMF was stirred at 100° C. for 2 h. The reaction was then diluted with 100 ml of DCM and washed with water (100 ml×3), dried over sodium sulfate and concentrated under reduced pressure. The yield was 950 mg (87%).

Synthesis Step 2: 3-Amino-2-(2-fluorophenoxy)benzonitrile

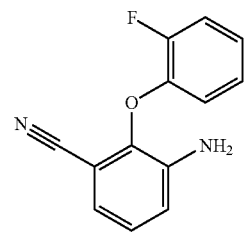 [SMILES: N#Cc1cccc(N)c1Oc1ccccc1F]

A solution of 950 mg of 2-(2-fluorophenoxy)-3-nitrobenzonitrile (3.68 mmol, 1.0 eq) and 2.49 g of SnCl$_2$.2H$_2$O (11.05 mmol, 3.0 eq) in 30 ml of EtOH was stirred at 80° C. for 16 h. The solution was then concentrated under reduced pressure, adjusted to pH=7-8 with 2N aqueous sodium hydroxide solution and extracted with ethyl acetate. The organic phase was dried over sodium sulfate and concentrated under reduced pressure and the residue was purified by column chromatography. The yield, as a yellow solid, was 750 mg (90%).

Synthesis Step 3: 2-(2-Fluorophenoxy)-3-(pyrimidin-2-ylamino)benzonitrile (Tab. Example 1-246)

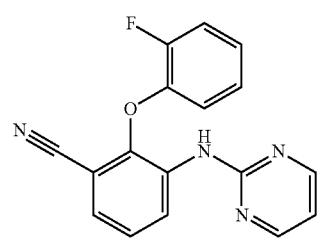 [SMILES: N#Cc1cccc(Nc2ncccn2)c1Oc1ccccc1F]

A solution of 250 mg of 3-amino-2-(2-fluorophenoxy) benzonitrile (1.09 mmol, 1.0 eq), 24.4 mg of Pd(AcO)$_2$ (0.11 mmol, 0.1 eq), 136.9 mg of BINAP (0.22 mmol, 0.2 eq), 244 mg of t-BuOK (2.18 mmol, 2 eq) and 125 mg of 2-chloropyrimidine (1.09 mmol, 1.0 eq) in 8 ml of toluene was stirred under argon at 100° C. for 12 h. The solvent was concentrated under reduced pressure and the residue was purified by column chromatography. The yield, as a yellow solid, was 65 mg.

Table Example Number 2-141

Synthesis Step 1: Methyl 4-(5-chloropyrimidin-2-ylamino)-3-fluorobenzoate

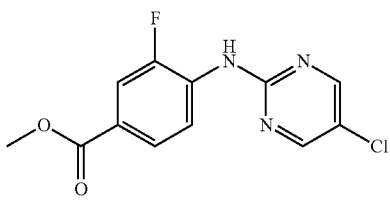 [SMILES: COC(=O)c1ccc(Nc2ncc(Cl)cn2)c(F)c1]

A solution of 2 g of methyl 4-amino-3-fluorobenzoate (11.8 mmol), 541 mg of Pd$_2$dba$_3$ (0.59 mmol, 0.05 eq), 341 mg of Xantphos (0.59 mmol, 0.05 eq), 5.78 g of Cs$_2$CO$_3$ (17.7 mmol, 1.5 eq) and 1.94 g of 2,5-dichloropyrimidine (13 mmol, 1.1 eq) in 25 ml of dioxane was stirred under argon at reflux for 3 h. The solvent was concentrated under reduced pressure and the residue was purified by column chromatography. The yield was 2.9 g (87%).

Synthesis Step 2: 4-(5-Chloropyrimidin-2-ylamino)-3-fluorobenzoic Acid

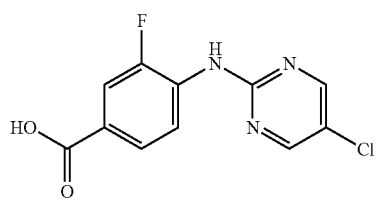 [SMILES: O=C(O)c1ccc(Nc2ncc(Cl)cn2)c(F)c1]

6.5 ml of 2N aqueous sodium hydroxide solution (12.9 mmol, 1.3 eq) were added to a solution of 2.8 g of methyl 4-(5-chloropyrimidin-2-ylamino)-3-fluorobenzoate (9.9 mmol) in 30 ml of methanol, and the mixture was heated at 50° C. for 10 h. The mixture was then diluted with water and washed with ethyl acetate. The aqueous solution was acidified with hydrochloric acid and the product was filtered off with suction. Yield 1.8 g (68%).

Synthesis Step 3: Ethyl (4-(5-chloropyrimidin-2-ylamino)-3-fluorophenyl)carbamate

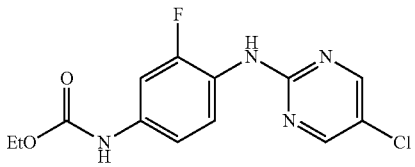 [SMILES: CCOC(=O)Nc1ccc(Nc2ncc(Cl)cn2)c(F)c1]

A solution of 1.8 g of 4-(5-chloropyrimidin-2-ylamino)-3-fluorobenzoic acid (6.73 mmol), 1.13 ml of triethylamine (8.1 mmol, 1.2 eq) and 1.74 ml of diphenylphosphoryl azide (8.1 mmol, 1.2 eq) in 45 ml of ethanol and 45 ml of dioxane was heated under reflux. Once the reaction had ended, the mixture was concentrated under reduced pressure and 2N hydrochloric acid and ethyl acetate were added. The organic phase was washed with brine, dried over sodium sulfate and concentrated and the residue was purified by column chromatography. Yield 1.5 g (72%, impure).

Synthesis Step 4: Ethyl (4-(5-chloropyrimidin-2-ylamino)-5-fluoro-2-nitrophenyl)carbamate

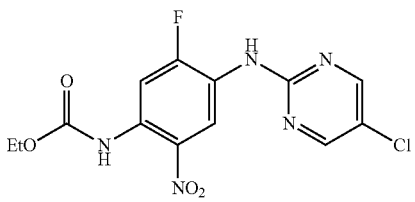 [SMILES: CCOC(=O)Nc1cc(F)c(Nc2ncc(Cl)cn2)cc1[N+](=O)[O-]]

A solution, prepared with cooling from 365 mg of nitric acid (60% strength, 3.8 mmol) and 1.74 ml of acetic anhydride, was, with cooling, added to a solution of 1.3 g of ethyl (4-(5-chloropyrimidin-2-ylamino)-3-fluorophenyl)carbamate (4.18 mmol) in 5 ml of acetic acid. After 1 h of stirring at room temperature, the mixture was made basic with sodium bicarbonate solution and extracted with ethyl acetate. The organic phase was washed with brine, dried over sodium sulfate and concentrated and the residue was purified by column chromatography. Yield 550 mg (40%).

Synthesis Step 5: Ethyl (4-(5-chloropyrimidin-2-ylamino)-5-(4-fluorophenoxy)-2-nitrophenyl)carbamate (Table Example Number 2-141)

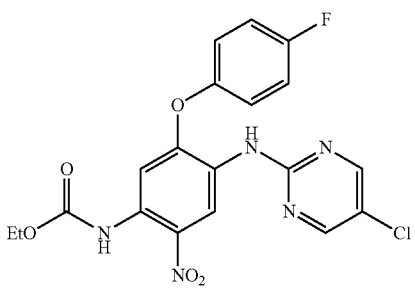 [SMILES: CCOC(=O)Nc1cc(Oc2ccc(F)cc2)c(Nc2ncc(Cl)cn2)cc1[N+](=O)[O-]]

A solution of 410 mg of ethyl (4-(5-chloropyrimidin-2-ylamino)-5-fluoro-2-nitrophenyl)carbamate (1.15 mmol), 155 mg of 4-fluorophenol (1.38 mmol, 1.2 eq) and 239 mg of potassium carbonate (1.73 mmol, 1.5 eq) in 10 ml of DMF was stirred at room temperature for 3 h. After addition of water, the product was filtered off with suction. Yield 440 mg (84%).

Table Example Number 2-130

4-(5-Chloropyrimidin-2-ylamino)-5-(4-fluorophenoxy)-2-nitroaniline

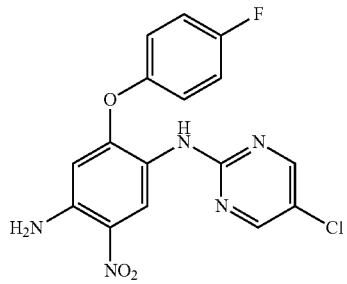 [SMILES: Nc1cc(Oc2ccc(F)cc2)c(Nc2ncc(Cl)cn2)cc1[N+](=O)[O-]]

0.7 ml of 2N aqueous sodium hydroxide solution was added to a solution of 160 mg of ethyl (4-(5-chloropyrimidin-2-ylamino)-5-(4-fluorophenoxy)-2-nitrophenyl)carbamate (0.36 mmol) in 3 ml of ethanol. After the reaction had ended, water was added, the mixture was extracted with DCM, the extract was concentrated and the residue was purified by column chromatography. Yield 35 mg (26%).

Table Example Number 2-101

2-Chloro-4-(5-chloropyrimidin-2-ylamino)-3-(4-fluorophenoxy)-6-nitroaniline

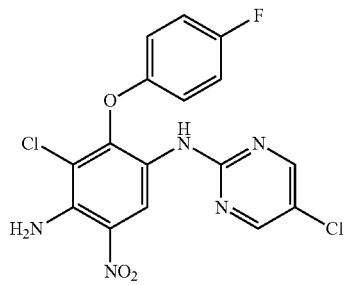 [SMILES: Nc1c([N+](=O)[O-])cc(Nc2ncc(Cl)cn2)c(Oc2ccc(F)cc2)c1Cl]

51 mg of NCS (0.38 mmol, 1 eq) were added to a solution of 145 mg of 4-(5-chloropyrimidin-2-ylamino)-5-(4-fluorophenoxy)-2-nitroaniline
(0.38 mmol) in 2 ml of DMF. After 2 d at room temperature, the mixture was diluted with ethyl acetate and washed with water and brine, dried over sodium sulfate and concentrated, and the residue was purified by column chromatography. Yield 25 mg (16%).

In analogy to the preparation examples cited above and recited at the appropriate point,
the compounds of the general formula specified hereinafter and shown in Table 1 are obtained.

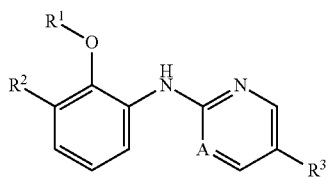

TABLE 1

| Example number | $R^2$ | $R^3$ | A | $R^1$ |
|---|---|---|---|---|
| 1-1 | F | H | CH | phenyl |
| 1-2 | F | H | CH | 2-fluorophenyl |
| 1-3 | F | H | CH | 3-fluorophenyl |
| 1-4 | F | H | CH | 4-fluorophenyl |
| 1-5 | F | H | CH | 3-chlorophenyl |
| 1-6 | F | H | CH | 4-chlorophenyl |
| 1-7 | F | H | CH | 2,4-difluorophenyl |
| 1-8 | F | H | CH | 2,5-difluorophenyl |
| 1-9 | F | H | CH | 3,4-difluorophenyl |
| 1-10 | F | H | CH | 3,5-difluorophenyl |
| 1-11 | F | H | CH | 2-chloro-4-fluorophenyl |
| 1-12 | F | H | CH | 4-methylphenyl |
| 1-13 | F | H | CH | 4-ethylphenyl |
| 1-14 | F | H | CH | 3-(trifluoromethyl)-phenyl |
| 1-15 | F | H | CH | 4-(trifluoromethyl)-phenyl |
| 1-16 | F | H | CH | 4-cyanophenyl |
| 1-17 | F | H | CH | 3-methoxyphenyl |
| 1-18 | F | H | CH | 4-methylthiophenyl |
| 1-19 | F | F | CH | phenyl |
| 1-20 | F | F | CH | 2-fluorophenyl |
| 1-21 | F | F | CH | 3-fluorophenyl |
| 1-22 | F | F | CH | 4-fluorophenyl |
| 1-23 | F | F | CH | 3-chlorophenyl |
| 1-24 | F | F | CH | 4-chlorophenyl |
| 1-25 | F | F | CH | 2,4-difluorophenyl |
| 1-26 | F | F | CH | 2,5-difluorophenyl |
| 1-27 | F | F | CH | 3,4-difluorophenyl |
| 1-28 | F | F | CH | 3,5-difluorophenyl |
| 1-29 | F | F | CH | 2-chloro-4-fluorophenyl |
| 1-30 | F | F | CH | 4-methylphenyl |
| 1-31 | F | F | CH | 4-ethylphenyl |
| 1-32 | F | F | CH | 3-(trifluoromethyl)-phenyl |
| 1-33 | F | F | CH | 4-(trifluoromethyl)-phenyl |
| 1-34 | F | F | CH | 4-cyanophenyl |
| 1-35 | F | F | CH | 3-methoxyphenyl |
| 1-36 | F | F | CH | 4-methylthiophenyl |
| 1-37 | F | Cl | CH | phenyl |
| 1-38 | F | Cl | CH | 2-fluorophenyl |
| 1-39 | F | Cl | CH | 3-fluorophenyl |
| 1-40 | F | Cl | CH | 4-fluorophenyl |
| 1-41 | F | Cl | CH | 3-chlorophenyl |
| 1-42 | F | Cl | CH | 4-chlorophenyl |
| 1-43 | F | Cl | CH | 2,4-difluorophenyl |
| 1-44 | F | Cl | CH | 2,5-difluorophenyl |
| 1-45 | F | Cl | CH | 3,4-difluorophenyl |
| 1-46 | F | Cl | CH | 3,5-difluorophenyl |
| 1-47 | F | Cl | CH | 2-chloro-4-fluorophenyl |
| 1-48 | F | Cl | CH | 3-(trifluoromethyl)-phenyl |
| 1-49 | F | Cl | CH | 4-(trifluoromethyl)-phenyl |
| 1-50 | F | Cl | CH | 3-methoxyphenyl |
| 1-51 | F | Cl | CH | 4-cyanophenyl |
| 1-52 | F | Cl | CH | 4-methylphenyl |
| 1-53 | F | Cl | CH | 4-ethylphenyl |
| 1-54 | F | Cl | CH | 4-methylthiophenyl |
| 1-55 | F | Cl | CF | 4-fluorophenyl |
| 1-56 | F | Cl | CF | 3,4-difluorophenyl |
| 1-57 | F | Cl | CCl | 4-fluorophenyl |
| 1-58 | F | Cl | CCl | 3,4-difluorophenyl |
| 1-59 | F | Br | CH | 4-fluorophenyl |
| 1-60 | F | Br | CH | 3,4-difluorophenyl |
| 1-61 | F | CN | CH | 4-fluorophenyl |
| 1-62 | F | CN | CH | 3,4-difluorophenyl |
| 1-63 | F | $NO_2$ | CH | 4-fluorophenyl |
| 1-64 | F | $NO_2$ | CH | 3,4-difluorophenyl |

TABLE 1-continued

| Example number | R² | R³ | A | R¹ |
|---|---|---|---|---|
| 1-65 | F | Me | CH | 4-fluorophenyl |
| 1-66 | F | Me | CH | 3,4-difluorophenyl |
| 1-67 | F | Et | CH | 4-fluorophenyl |
| 1-68 | F | Et | CH | 3,4-difluorophenyl |
| 1-69 | F | MeO | CH | 4-fluorophenyl |
| 1-70 | F | MeO | CH | 3,4-difluorophenyl |
| 1-71 | F | MeS | CH | 4-fluorophenyl |
| 1-72 | F | MeS | CH | 3,4-difluorophenyl |
| 1-73 | Cl | F | CH | 4-fluorophenyl |
| 1-74 | Cl | F | CH | 3,4-difluorophenyl |
| 1-75 | Cl | Cl | CH | 4-fluorophenyl |
| 1-76 | Cl | Cl | CH | 3,4-difluorophenyl |
| 1-77 | Me | F | CH | 4-fluorophenyl |
| 1-78 | Me | F | CH | 3,4-difluorophenyl |
| 1-79 | Me | Cl | CH | 4-fluorophenyl |
| 1-80 | Me | Cl | CH | 3,4-difluorophenyl |
| 1-81 | Et | F | CH | 4-fluorophenyl |
| 1-82 | Et | F | CH | 3,4-difluorophenyl |
| 1-83 | Et | Cl | CH | 4-fluorophenyl |
| 1-84 | Et | Cl | CH | 3,4-difluorophenyl |
| 1-85 | CN | H | CH | phenyl |
| 1-86 | CN | H | CH | 2-fluorophenyl |
| 1-87 | CN | H | CH | 3-fluorophenyl |
| 1-88 | CN | H | CH | 4-fluorophenyl |
| 1-89 | CN | H | CH | 3-chlorophenyl |
| 1-90 | CN | H | CH | 4-chlorophenyl |
| 1-91 | CN | H | CH | 2,4-difluorophenyl |
| 1-92 | CN | H | CH | 2,5-difluorophenyl |
| 1-93 | CN | H | CH | 3,4-difluorophenyl |
| 1-94 | CN | H | CH | 3,5-difluorophenyl |
| 1-95 | CN | H | CH | 2-chloro-4-fluorophenyl |
| 1-96 | CN | H | CH | 4-methylphenyl |
| 1-97 | CN | H | CH | 4-ethylphenyl |
| 1-98 | CN | H | CH | 3-(trifluoromethyl)-phenyl |
| 1-99 | CN | H | CH | 4-(trifluoromethyl)-phenyl |
| 1-100 | CN | H | CH | 4-cyanophenyl |
| 1-101 | CN | H | CH | 3-methoxyphenyl |
| 1-102 | CN | H | CH | 4-methylthiophenyl |
| 1-103 | CN | F | CH | phenyl |
| 1-104 | CN | F | CH | 2-fluorophenyl |
| 1-105 | CN | F | CH | 3-fluorophenyl |
| 1-106 | CN | F | CH | 4-fluorophenyl |
| 1-107 | CN | F | CH | 3-chlorophenyl |
| 1-108 | CN | F | CH | 4-chlorophenyl |
| 1-109 | CN | F | CH | 2,4-difluorophenyl |
| 1-110 | CN | F | CH | 2,5-difluorophenyl |
| 1-111 | CN | F | CH | 3,4-difluorophenyl |
| 1-112 | CN | F | CH | 3,5-difluorophenyl |
| 1-113 | CN | F | CH | 2-chloro-4-fluorophenyl |
| 1-114 | CN | F | CH | 4-methylphenyl |
| 1-115 | CN | F | CH | 4-ethylphenyl |
| 1-116 | CN | F | CH | 3-(trifluoromethyl)-phenyl |
| 1-117 | CN | F | CH | 4-(trifluoromethyl)-phenyl |
| 1-118 | CN | F | CH | 4-cyanophenyl |
| 1-119 | CN | F | CH | 3-methoxyphenyl |
| 1-120 | CN | F | CH | 4-methylthiophenyl |
| 1-121 | CN | Cl | CH | phenyl |
| 1-122 | CN | Cl | CH | 2-fluorophenyl |
| 1-123 | CN | Cl | CH | 3-fluorophenyl |
| 1-124 | CN | Cl | CH | 4-fluorophenyl |
| 1-125 | CN | Cl | CH | 3-chlorophenyl |
| 1-126 | CN | Cl | CH | 4-chlorophenyl |
| 1-127 | CN | Cl | CH | 2,4-difluorophenyl |
| 1-128 | CN | Cl | CH | 2,5-difluorophenyl |
| 1-129 | CN | Cl | CH | 3,4-difluorophenyl |
| 1-130 | CN | Cl | CH | 3,5-difluorophenyl |
| 1-131 | CN | Cl | CH | 2-chloro-4-fluorophenyl |
| 1-132 | CN | Cl | CH | 4-methylphenyl |
| 1-133 | CN | Cl | CH | 4-ethylphenyl |
| 1-134 | CN | Cl | CH | 3-(trifluoromethyp-phenyl |
| 1-135 | CN | Cl | CH | 4-(trifluoromethyp-phenyl |
| 1-136 | CN | Cl | CH | 4-cyanophenyl |
| 1-137 | CN | Cl | CH | 3-methoxyphenyl |
| 1-138 | CN | Cl | CH | 4-methylthiophenyl |
| 1-139 | CN | Cl | CF | 4-fluorophenyl |
| 1-140 | CN | Cl | CF | 3,4-difluorophenyl |
| 1-141 | CN | Cl | CCl | 4-fluorophenyl |
| 1-142 | CN | Cl | CCl | 3,4-difluorophenyl |
| 1-143 | CN | Br | CH | 4-fluorophenyl |
| 1-144 | CN | Br | CH | 3,4-difluorophenyl |
| 1-145 | CN | CN | CH | 4-fluorophenyl |
| 1-146 | CN | CN | CH | 3,4-difluorophenyl |
| 1-147 | CN | NO₂ | CH | 4-fluorophenyl |
| 1-148 | CN | NO₂ | CH | 3,4-difluorophenyl |
| 1-149 | CN | Me | CH | 4-fluorophenyl |
| 1-150 | CN | Me | CH | 3,4-difluorophenyl |
| 1-151 | CN | Et | CH | 4-fluorophenyl |
| 1-152 | CN | Et | CH | 3,4-difluorophenyl |
| 1-153 | CN | MeO | CH | 4-fluorophenyl |
| 1-154 | CN | MeO | CH | 3,4-difluorophenyl |
| 1-155 | CN | MeS | CH | 4-fluorophenyl |
| 1-156 | CN | MeS | CH | 3,4-difluorophenyl |
| 1-157 | MeO | F | CH | 4-fluorophenyl |
| 1-158 | MeO | F | CH | 3,4-difluorophenyl |
| 1-159 | MeO | Cl | CH | 4-fluorophenyl |
| 1-160 | MeO | Cl | CH | 3,4-difluorophenyl |
| 1-161 | MeS | F | CH | 4-fluorophenyl |
| 1-162 | MeS | F | CH | 3,4-difluorophenyl |
| 1-163 | MeS | Cl | CH | 4-fluorophenyl |
| 1-164 | MeS | Cl | CH | 3,4-difluorophenyl |
| 1-165 | F | H | N | phenyl |
| 1-166 | F | H | N | 2-fluorophenyl |
| 1-167 | F | H | N | 3-fluorophenyl |
| 1-168 | F | H | N | 4-fluorophenyl |
| 1-169 | F | H | N | 3-chlorophenyl |
| 1-170 | F | H | N | 4-chlorophenyl |
| 1-171 | F | H | N | 2,4-difluorophenyl |
| 1-172 | F | H | N | 2,5-difluorophenyl |
| 1-173 | F | H | N | 3,4-difluorophenyl |
| 1-174 | F | H | N | 3,5-difluorophenyl |
| 1-175 | F | H | N | 4-methylphenyl |
| 1-176 | F | H | N | 4-ethylphenyl |
| 1-177 | F | H | N | 2-chloro-4-fluorophenyl |
| 1-178 | F | H | N | 3-(trifluoromethyl)-phenyl |
| 1-179 | F | H | N | 4-(trifluoromethyl)-phenyl |
| 1-180 | F | H | N | 4-cyanophenyl |
| 1-181 | F | H | N | 3-methoxyphenyl |
| 1-182 | F | H | N | 4-methylthiophenyl |
| 1-183 | F | F | N | phenyl |
| 1-184 | F | F | N | 2-fluorophenyl |
| 1-185 | F | F | N | 3-fluorophenyl |
| 1-186 | F | F | N | 4-fluorophenyl |
| 1-187 | F | F | N | 3-chlorophenyl |
| 1-188 | F | F | N | 4-chlorophenyl |
| 1-189 | F | F | N | 2,4-difluorophenyl |
| 1-190 | F | F | N | 2,5-difluorophenyl |
| 1-191 | F | F | N | 3,4-difluorophenyl |
| 1-192 | F | F | N | 3,5-difluorophenyl |
| 1-193 | F | F | N | 2-chloro-4-fluorophenyl |
| 1-194 | F | F | N | 4-methylphenyl |
| 1-195 | F | F | N | 4-ethylphenyl |
| 1-196 | F | F | N | 3-(trifluoromethyl)-phenyl |
| 1-197 | F | F | N | 4-(trifluoromethyl)-phenyl |
| 1-198 | F | F | N | 4-cyanophenyl |
| 1-199 | F | F | N | 3-methoxyphenyl |
| 1-200 | F | F | N | 4-methylthiophenyl |
| 1-201 | F | Cl | N | phenyl |
| 1-202 | F | Cl | N | 2-fluorophenyl |
| 1-203 | F | Cl | N | 3-fluorophenyl |
| 1-204 | F | Cl | N | 4-fluorophenyl |
| 1-205 | F | Cl | N | 3-chlorophenyl |
| 1-206 | F | Cl | N | 4-chlorophenyl |
| 1-207 | F | Cl | N | 2,4-difluorophenyl |
| 1-208 | F | Cl | N | 2,5-difluorophenyl |
| 1-209 | F | Cl | N | 3,4-difluorophenyl |
| 1-210 | F | Cl | N | 3,5-difluorophenyl |
| 1-211 | F | Cl | N | 2-chloro-4-fluorophenyl |
| 1-212 | F | Cl | N | 4-methylphenyl |
| 1-213 | F | Cl | N | 4-ethylphenyl |
| 1-214 | F | Cl | N | 3-(trifluoromethyl)-phenyl |
| 1-215 | F | Cl | N | 4-(trifluoromethyl)-phenyl |
| 1-216 | F | Cl | N | 4-cyanophenyl |
| 1-217 | F | Cl | N | 3-methoxyphenyl |
| 1-218 | F | Cl | N | 4-methylthiophenyl |

TABLE 1-continued

| Example number | $R^2$ | $R^3$ | A | $R^1$ |
|---|---|---|---|---|
| 1-219 | F | Br | N | 4-fluorophenyl |
| 1-220 | F | Br | N | 3,4-difluorophenyl |
| 1-221 | F | CN | N | 4-fluorophenyl |
| 1-222 | F | CN | N | 3,4-difluorophenyl |
| 1-223 | F | $NO_2$ | N | 4-fluorophenyl |
| 1-224 | F | $NO_2$ | N | 3,4-difluorophenyl |
| 1-225 | F | Me | N | 4-fluorophenyl |
| 1-226 | F | Me | N | 3,4-difluorophenyl |
| 1-227 | F | Et | N | 4-fluorophenyl |
| 1-228 | F | Et | N | 3,4-difluorophenyl |
| 1-229 | F | MeO | N | 4-fluorophenyl |
| 1-230 | F | MeO | N | 3,4-difluorophenyl |
| 1-231 | F | MeS | N | 4-fluorophenyl |
| 1-232 | F | MeS | N | 3,4-difluorophenyl |
| 1-233 | Cl | F | N | 4-fluorophenyl |
| 1-234 | Cl | F | N | 3,4-difluorophenyl |
| 1-235 | Cl | Cl | N | 4-fluorophenyl |
| 1-236 | Cl | Cl | N | 3,4-difluorophenyl |
| 1-237 | Me | F | N | 4-fluorophenyl |
| 1-238 | Me | F | N | 3,4-difluorophenyl |
| 1-239 | Me | Cl | N | 4-fluorophenyl |
| 1-240 | Me | Cl | N | 3,4-difluorophenyl |
| 1-241 | Et | F | N | 4-fluorophenyl |
| 1-242 | Et | F | N | 3,4-difluorophenyl |
| 1-243 | Et | Cl | N | 4-fluorophenyl |
| 1-244 | Et | Cl | N | 3,4-difluorophenyl |
| 1-245 | CN | H | N | phenyl |
| 1-246 | CN | H | N | 2-fluorophenyl |
| 1-247 | CN | H | N | 3-fluorophenyl |
| 1-248 | CN | H | N | 4-fluorophenyl |
| 1-249 | CN | H | N | 3-chlorophenyl |
| 1-250 | CN | H | N | 4-chlorophenyl |
| 1-251 | CN | H | N | 2,4-difluorophenyl |
| 1-252 | CN | H | N | 2,5-difluorophenyl |
| 1-253 | CN | H | N | 3,4-difluorophenyl |
| 1-254 | CN | H | N | 3,5-difluorophenyl |
| 1-255 | CN | H | N | 2-chloro-4-fluorophenyl |
| 1-256 | CN | H | N | 4-chloro-2-fluorophenyl |
| 1-257 | CN | H | N | 4-methylphenyl |
| 1-258 | CN | H | N | 4-ethylphenyl |
| 1-259 | CN | H | N | 3-(trifluoromethyl)-phenyl |
| 1-260 | CN | H | N | 4-(trifluoromethyl)-phenyl |
| 1-261 | CN | H | N | 4-cyanophenyl |
| 1-262 | CN | H | N | 3-methoxyphenyl |
| 1-263 | CN | H | N | 4-methylthiophenyl |
| 1-264 | CN | F | N | phenyl |
| 1-265 | CN | F | N | 2-fluorophenyl |
| 1-266 | CN | F | N | 3-fluorophenyl |
| 1-267 | CN | F | N | 4-fluorophenyl |
| 1-268 | CN | F | N | 3-chlorophenyl |
| 1-269 | CN | F | N | 4-chlorophenyl |
| 1-270 | CN | F | N | 2,4-difluorophenyl |
| 1-271 | CN | F | N | 2,5-difluorophenyl |
| 1-272 | CN | F | N | 3,4-difluorophenyl |
| 1-273 | CN | F | N | 3,5-difluorophenyl |
| 1-274 | CN | F | N | 2-chloro-4-fluorophenyl |
| 1-275 | CN | F | N | 4-chloro-2-fluorophenyl |
| 1-276 | CN | F | N | 4-methylphenyl |
| 1-277 | CN | F | N | 4-ethylphenyl |
| 1-278 | CN | F | N | 3-(trifluoromethyl)-phenyl |
| 1-279 | CN | F | N | 4-(trifluoromethyl)-phenyl |
| 1-280 | CN | F | N | 4-cyanophenyl |
| 1-281 | CN | F | N | 3-methoxyphenyl |
| 1-282 | CN | F | N | 4-methylthiophenyl |
| 1-283 | CN | Cl | N | phenyl |
| 1-284 | CN | Cl | N | 2-fluorophenyl |
| 1-285 | CN | Cl | N | 3-fluorophenyl |
| 1-286 | CN | Cl | N | 4-fluorophenyl |
| 1-287 | CN | Cl | N | 3-chlorophenyl |
| 1-288 | CN | Cl | N | 4-chlorophenyl |
| 1-289 | CN | Cl | N | 2,4-difluorophenyl |
| 1-290 | CN | Cl | N | 2,5-difluorophenyl |
| 1-291 | CN | Cl | N | 3,4-difluorophenyl |
| 1-292 | CN | Cl | N | 3,5-difluorophenyl |
| 1-293 | CN | Cl | N | 2-chloro-4-fluorophenyl |
| 1-294 | CN | Cl | N | 4-chloro-2-fluorophenyl |
| 1-295 | CN | Cl | N | 4-methylphenyl |
| 1-296 | CN | Cl | N | 4-ethylphenyl |
| 1-297 | CN | Cl | N | 3-(trifluoromethyl)-phenyl |
| 1-298 | CN | Cl | N | 4-(trifluoromethyl)-phenyl |
| 1-299 | CN | Cl | N | 4-cyanophenyl |
| 1-300 | CN | Cl | N | 3-methoxyphenyl |
| 1-301 | CN | Cl | N | 4-methylthiophenyl |
| 1-302 | CN | Br | N | 4-fluorophenyl |
| 1-303 | CN | Br | N | 3,4-difluorophenyl |
| 1-304 | CN | CN | N | 4-fluorophenyl |
| 1-305 | CN | CN | N | 3,4-difluorophenyl |
| 1-306 | CN | $NO_2$ | N | 4-fluorophenyl |
| 1-307 | CN | $NO_2$ | N | 3,4-difluorophenyl |
| 1-308 | CN | Me | N | 4-fluorophenyl |
| 1-309 | CN | Me | N | 3,4-difluorophenyl |
| 1-310 | CN | Et | N | 4-fluorophenyl |
| 1-311 | CN | Et | N | 3,4-difluorophenyl |
| 1-312 | CN | MeO | N | 4-fluorophenyl |
| 1-313 | CN | MeO | N | 3,4-difluorophenyl |
| 1-314 | CN | $CHF_2O$ | N | 4-fluorophenyl |
| 1-315 | CN | $CHF_2O$ | N | 3,4-difluorophenyl |
| 1-316 | CN | $CF_3O$ | N | 4-fluorophenyl |
| 1-317 | CN | $CF_3O$ | N | 3,4-difluorophenyl |
| 1-318 | CN | MeS | N | 4-fluorophenyl |
| 1-319 | CN | MeS | N | 3,4-difluorophenyl |
| 1-320 | CN | $CF_3S$ | N | 4-fluorophenyl |
| 1-321 | CN | $CF_3S$ | N | 3,4-difluorophenyl |
| 1-322 | MeO | F | N | 4-fluorophenyl |
| 1-323 | MeO | F | N | 3,4-difluorophenyl |
| 1-324 | MeO | Cl | N | 4-fluorophenyl |
| 1-325 | MeO | Cl | N | 3,4-difluorophenyl |
| 1-326 | MeS | F | N | 4-fluorophenyl |
| 1-327 | MeS | F | N | 3,4-difluorophenyl |
| 1-328 | MeS | Cl | N | 4-fluorophenyl |
| 1-329 | MeS | Cl | N | 3,4-difluorophenyl |
| 1-330 | CN | $CHF_2O$ | CH | 4-fluorophenyl |
| 1-331 | CN | $CHF_2O$ | CH | 3,4-difluorophenyl |
| 1-332 | CN | $CF_3O$ | CH | 4-fluorophenyl |
| 1-333 | CN | $CF_3O$ | CH | 3,4-difluorophenyl |
| 1-334 | CN | $CF_3S$ | CH | 4-fluorophenyl |
| 1-335 | CN | $CF_3S$ | CH | 3,4-difluorophenyl |
| 1-336 | H | Cl | N | phenyl |
| 1-337 | H | Cl | N | 4-fluorophenyl |
| 1-338 | H | Cl | N | 3,4-difluorophenyl |
| 1-339 | H | Cl | N | 4-cyanophenyl |
| 1-340 | Cl | Cl | N | phenyl |
| 1-341 | Cl | Cl | N | 4-chlorophenyl |
| 1-342 | CN | OiPr | CH | 4-fluorophenyl |
| 1-343 | CN | OiPr | CH | 3,4-difluorophenyl |
| 1-344 | CN | OiPr | N | 4-fluorophenyl |
| 1-345 | CN | OiPr | N | 3,4-difluorophenyl |
| 1-346 | H | Cl | CH | 4-fluorophenyl |
| 1-347 | H | Cl | CH | 3,4-difluorophenyl |
| 1-348 | NO2 | Cl | CH | 4-fluorophenyl |
| 1-349 | NO2 | Cl | CH | 3,4-difluorophenyl |
| 1-350 | NO2 | Cl | N | 4-fluorophenyl |
| 1-351 | NO2 | Cl | N | 3,4-difluorophenyl |
| 1-352 | NH2 | Cl | CH | 4-fluorophenyl |
| 1-353 | NH2 | Cl | CH | 3,4-difluorophenyl |
| 1-354 | NH2 | Cl | N | 4-fluorophenyl |
| 1-355 | NH2 | Cl | N | 3,4-difluorophenyl |
| 1-356 | Br | Cl | CH | 4-fluorophenyl |
| 1-357 | Br | Cl | CH | 3,4-difluorophenyl |
| 1-358 | Br | Cl | N | 4-fluorophenyl |
| 1-359 | Br | Cl | N | 3,4-difluorophenyl |
| 1-360 | CN | EtO | CH | 4-fluorophenyl |
| 1-361 | CN | EtO | CH | 3,4-difluorophenyl |
| 1-362 | CN | EtO | N | 4-fluorophenyl |
| 1-363 | CN | EtO | N | 3,4-difluorophenyl |
| 1-364 | CN | Cl | N | 4-cyano-3-fluorophenyl |
| 1-365 | NHMe | Cl | N | 4-fluorophenyl |
| 1-366 | $NMe_2$ | Cl | N | 4-fluorophenyl |
| 1-367 | NHC(O)H | Cl | N | 4-fluorophenyl |
| 1-368 | NHAc | Cl | N | 4-fluorophenyl |
| 1-369 | NMeAc | Cl | N | 4-fluorophenyl |
| 1-370 | I | Cl | CH | 4-fluorophenyl |
| 1-371 | I | Cl | CH | 3,4-difluorophenyl |
| 1-372 | I | Cl | N | 4-fluorophenyl |

TABLE 1-continued

| Example number | R² | R³ | A | R¹ |
|---|---|---|---|---|
| 1-373 | I | Cl | N | 3,4-difluorophenyl |
| 1-374 | CN | F | N | 2,3,4-trifluorophenyl |
| 1-375 | CN | F | N | 2,4,5-trifluorophenyl |
| 1-376 | SEt | Cl | N | 4-fluorophenyl |

In analogy to the preparation examples cited above and recited at the appropriate point, the compounds of the general formula specified hereinafter and shown in Table 2 are obtained.

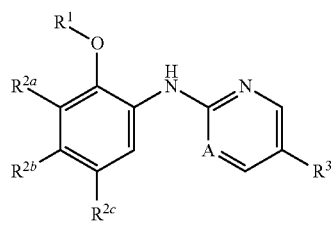

TABLE 2

| Example number | R²ᵃ | R²ᵇ | R²ᶜ | R³ | A | R¹ |
|---|---|---|---|---|---|---|
| 2-1 | F | NH₂ | H | F | CH | 4-fluorophenyl |
| 2-2 | F | NH₂ | H | F | CH | 3,4-difluorophenyl |
| 2-3 | F | NH₂ | Cl | F | CH | 4-fluorophenyl |
| 2-4 | F | NH₂ | Cl | F | CH | 3,4-difluorophenyl |
| 2-5 | F | NH₂ | Br | F | CH | 4-fluorophenyl |
| 2-6 | F | NH₂ | Br | F | CH | 3,4-difluorophenyl |
| 2-7 | F | NH₂ | NO₂ | F | CH | 4-fluorophenyl |
| 2-8 | F | NH₂ | NO₂ | F | CH | 3,4-difluorophenyl |
| 2-9 | F | NHCOOEt | H | F | CH | 4-fluorophenyl |
| 2-10 | F | NHCOOEt | H | F | CH | 3,4-difluorophenyl |
| 2-11 | F | NH₂ | H | Cl | CH | 4-fluorophenyl |
| 2-12 | F | NH₂ | H | Cl | CH | 3,4-difluorophenyl |
| 2-13 | F | NH₂ | Cl | Cl | CH | 4-fluorophenyl |
| 2-14 | F | NH₂ | Cl | Cl | CH | 3,4-difluorophenyl |
| 2-15 | F | NH₂ | Br | Cl | CH | 4-fluorophenyl |
| 2-16 | F | NH₂ | Br | Cl | CH | 3,4-difluorophenyl |
| 2-17 | F | NH₂ | NO₂ | Cl | CH | 4-fluorophenyl |
| 2-18 | F | NH₂ | NO₂ | Cl | CH | 3,4-difluorophenyl |
| 2-19 | F | NHCOOEt | H | Cl | CH | 4-fluorophenyl |
| 2-20 | F | NHCOOEt | H | Cl | CH | 3,4-difluorophenyl |
| 2-21 | Cl | NH₂ | H | F | CH | 4-fluorophenyl |
| 2-22 | Cl | NH₂ | H | F | CH | 3,4-difluorophenyl |
| 2-23 | Cl | NH₂ | Cl | F | CH | 4-fluorophenyl |
| 2-24 | Cl | NH₂ | Cl | F | CH | 3,4-difluorophenyl |
| 2-25 | Cl | NH₂ | Br | F | CH | 4-fluorophenyl |
| 2-26 | Cl | NH₂ | Br | F | CH | 3,4-difluorophenyl |
| 2-27 | Cl | NH₂ | NO₂ | F | CH | 4-fluorophenyl |
| 2-28 | Cl | NH₂ | NO₂ | F | CH | 3,4-difluorophenyl |
| 2-29 | Cl | NHCOOEt | H | F | CH | 4-fluorophenyl |
| 2-30 | Cl | NHCOOEt | H | F | CH | 3,4-difluorophenyl |
| 2-31 | Cl | NH₂ | H | Cl | CH | 4-fluorophenyl |
| 2-32 | Cl | NH₂ | H | Cl | CH | 3,4-difluorophenyl |
| 2-33 | Cl | NH₂ | Cl | Cl | CH | 4-fluorophenyl |
| 2-34 | Cl | NH₂ | Cl | Cl | CH | 3,4-difluorophenyl |
| 2-35 | Cl | NH₂ | Br | Cl | CH | 4-fluorophenyl |
| 2-36 | Cl | NH₂ | Br | Cl | CH | 3,4-difluorophenyl |
| 2-37 | Cl | NH₂ | NO₂ | Cl | CH | 4-fluorophenyl |
| 2-38 | Cl | NH₂ | NO₂ | Cl | CH | 3,4-difluorophenyl |
| 2-39 | Cl | COOH | H | Cl | CH | 4-fluorophenyl |
| 2-40 | Cl | COOH | H | Cl | CH | 3,4-difluorophenyl |
| 2-41 | Cl | COOMe | H | Cl | CH | 4-fluorophenyl |
| 2-42 | Cl | COOMe | H | Cl | CH | 3,4-difluorophenyl |
| 2-43 | Cl | NHCOOEt | H | Cl | CH | 4-fluorophenyl |
| 2-44 | Cl | NHCOOEt | H | Cl | CH | 3,4-difluorophenyl |
| 2-45 | CN | NH₂ | H | F | CH | 4-fluorophenyl |
| 2-46 | CN | NH₂ | H | F | CH | 3,4-difluorophenyl |
| 2-47 | CN | NH₂ | Cl | F | CH | 4-fluorophenyl |
| 2-48 | CN | NH₂ | Cl | F | CH | 3,4-difluorophenyl |
| 2-49 | CN | NH₂ | Br | F | CH | 4-fluorophenyl |
| 2-50 | CN | NH₂ | Br | F | CH | 3,4-difluorophenyl |
| 2-51 | CN | NH₂ | NO₂ | F | CH | 4-fluorophenyl |
| 2-52 | CN | NH₂ | NO₂ | F | CH | 3,4-difluorophenyl |
| 2-53 | CN | NHCOOEt | H | F | CH | 4-fluorophenyl |
| 2-54 | CN | NHCOOEt | H | F | CH | 3,4-difluorophenyl |
| 2-55 | CN | NH₂ | H | Cl | CH | 4-fluorophenyl |
| 2-56 | CN | NH₂ | H | Cl | CH | 3,4-difluorophenyl |
| 2-57 | CN | NH₂ | Cl | Cl | CH | 4-fluorophenyl |
| 2-58 | CN | NH₂ | Cl | Cl | CH | 3,4-difluorophenyl |
| 2-59 | CN | NH₂ | Br | Cl | CH | 4-fluorophenyl |
| 2-60 | CN | NH₂ | Br | Cl | CH | 3,4-difluorophenyl |
| 2-61 | CN | NH₂ | NO₂ | Cl | CH | 4-fluorophenyl |
| 2-62 | CN | NH₂ | NO₂ | Cl | CH | 3,4-difluorophenyl |
| 2-63 | CN | NHCOOEt | H | Cl | CH | 4-fluorophenyl |
| 2-64 | CN | NHCOOEt | H | Cl | CH | 3,4-difluorophenyl |
| 2-65 | F | NH₂ | H | F | N | 4-fluorophenyl |
| 2-66 | F | NH₂ | H | F | N | 3,4-difluorophenyl |
| 2-67 | F | NH₂ | Cl | F | N | 4-fluorophenyl |
| 2-68 | F | NH₂ | Cl | F | N | 3,4-difluorophenyl |
| 2-69 | F | NH₂ | Br | F | N | 4-fluorophenyl |
| 2-70 | F | NH₂ | Br | F | N | 3,4-difluorophenyl |
| 2-71 | F | NH₂ | NO₂ | F | N | 4-fluorophenyl |
| 2-72 | F | NH₂ | NO₂ | F | N | 3,4-difluorophenyl |
| 2-73 | F | NHCOOEt | H | F | N | 4-fluorophenyl |
| 2-74 | F | NHCOOEt | H | F | N | 3,4-difluorophenyl |
| 2-75 | F | NH₂ | H | Cl | N | 4-fluorophenyl |
| 2-76 | F | NH₂ | H | Cl | N | 3,4-difluorophenyl |
| 2-77 | F | NH₂ | Cl | Cl | N | 4-fluorophenyl |
| 2-78 | F | NH₂ | Cl | Cl | N | 3,4-difluorophenyl |
| 2-79 | F | NH₂ | Br | Cl | N | 4-fluorophenyl |
| 2-80 | F | NH₂ | Br | Cl | N | 3,4-difluorophenyl |
| 2-81 | F | NH₂ | NO₂ | Cl | N | 4-fluorophenyl |
| 2-82 | F | NH₂ | NO₂ | Cl | N | 3,4-difluorophenyl |
| 2-83 | F | NHCOOEt | H | Cl | N | 4-fluorophenyl |
| 2-84 | F | NHCOOEt | H | Cl | N | 3,4-difluorophenyl |
| 2-85 | Cl | NH₂ | H | F | N | 4-fluorophenyl |
| 2-86 | Cl | NH₂ | H | F | N | 3,4-difluorophenyl |
| 2-87 | Cl | NH₂ | Cl | F | N | 4-fluorophenyl |
| 2-88 | Cl | NH₂ | Cl | F | N | 3,4-difluorophenyl |
| 2-89 | Cl | NH₂ | Br | F | N | 4-fluorophenyl |
| 2-90 | Cl | NH₂ | Br | F | N | 3,4-difluorophenyl |
| 2-91 | Cl | NH₂ | NO₂ | F | N | 4-fluorophenyl |
| 2-92 | Cl | NH₂ | NO₂ | F | N | 3,4-difluorophenyl |
| 2-93 | Cl | NHCOOEt | H | F | N | 4-fluorophenyl |
| 2-94 | Cl | NHCOOEt | H | F | N | 3,4-difluorophenyl |
| 2-95 | Cl | NH₂ | H | Cl | N | 4-fluorophenyl |
| 2-96 | Cl | NH₂ | H | Cl | N | 3,4-difluorophenyl |
| 2-97 | Cl | NH₂ | Cl | Cl | N | 4-fluorophenyl |
| 2-98 | Cl | NH₂ | Cl | Cl | N | 3,4-difluorophenyl |
| 2-99 | Cl | NH₂ | Br | Cl | N | 4-fluorophenyl |
| 2-100 | Cl | NH₂ | Br | Cl | N | 3,4-difluorophenyl |
| 2-101 | Cl | NH₂ | NO₂ | Cl | N | 4-fluorophenyl |
| 2-102 | Cl | NH₂ | NO₂ | Cl | N | 3,4-difluorophenyl |
| 2-103 | Cl | COOH | H | Cl | N | 4-fluorophenyl |
| 2-104 | Cl | COOH | H | Cl | N | 3,4-difluorophenyl |
| 2-105 | Cl | COOMe | H | Cl | N | 4-fluorophenyl |
| 2-106 | Cl | COOMe | H | Cl | N | 3,4-difluorophenyl |
| 2-107 | Cl | NHCOOEt | H | Cl | N | 4-fluorophenyl |
| 2-108 | Cl | NHCOOEt | H | Cl | N | 3,4-difluorophenyl |
| 2-109 | CN | NH₂ | H | F | N | 4-fluorophenyl |
| 2-110 | CN | NH₂ | H | F | N | 3,4-difluorophenyl |
| 2-111 | CN | NH₂ | Cl | F | N | 4-fluorophenyl |
| 2-112 | CN | NH₂ | Cl | F | N | 3,4-difluorophenyl |
| 2-113 | CN | NH₂ | Br | F | N | 4-fluorophenyl |
| 2-114 | CN | NH₂ | Br | F | N | 3,4-difluorophenyl |
| 2-115 | CN | NH₂ | NO₂ | F | N | 4-fluorophenyl |
| 2-116 | CN | NH₂ | NO₂ | F | N | 3,4-difluorophenyl |
| 2-117 | CN | NHCOOEt | H | F | N | 4-fluorophenyl |
| 2-118 | CN | NHCOOEt | H | F | N | 3,4-difluorophenyl |
| 2-119 | CN | NH₂ | H | Cl | N | 4-fluorophenyl |
| 2-120 | CN | NH₂ | H | Cl | N | 3,4-difluorophenyl |
| 2-121 | CN | NH₂ | Cl | Cl | N | 4-fluorophenyl |
| 2-122 | CN | NH₂ | Cl | Cl | N | 3,4-difluorophenyl |

TABLE 2-continued

| Example number | $R^{2a}$ | $R^{2b}$ | $R^{2c}$ | $R^3$ | A | $R^1$ |
|---|---|---|---|---|---|---|
| 2-123 | CN | NH$_2$ | Br | Cl | N | 4-fluorophenyl |
| 2-124 | CN | NH$_2$ | Br | Cl | N | 3,4-difluorophenyl |
| 2-125 | CN | NH$_2$ | NO$_2$ | Cl | N | 4-fluorophenyl |
| 2-126 | CN | NH$_2$ | NO$_2$ | Cl | N | 3,4-difluorophenyl |
| 2-127 | CN | NHCOOEt | H | Cl | N | 4-fluorophenyl |
| 2-128 | CN | NHCOOEt | H | Cl | N | 3,4-difluorophenyl |
| 2-129 | H | H | NO$_2$ | Cl | N | 4-fluorophenyl |
| 2-130 | H | NH$_2$ | NO$_2$ | Cl | N | 4-fluorophenyl |
| 2-131 | H | NH$_2$ | H | Cl | N | 4-fluorophenyl |
| 2-132 | H | NHCOOEt | H | Cl | N | 4-fluorophenyl |
| 2-133 | H | COOH | H | Cl | N | 4-fluorophenyl |
| 2-134 | H | COOMe | H | Cl | N | 4-fluorophenyl |
| 2-135 | H | NH$_2$ | H | F | N | 4-fluorophenyl |
| 2-136 | H | NHCOOEt | H | F | N | 4-fluorophenyl |
| 2-137 | H | COOH | H | F | N | 4-fluorophenyl |
| 2-138 | H | COOMe | H | F | N | 4-fluorophenyl |
| 2-139 | Br | Br | H | Cl | N | 4-fluorophenyl |
| 2-140 | H | NH$_2$ | Br | Cl | N | 4-fluorophenyl |
| 2-141 | H | NHCOOEt | NO$_2$ | Cl | N | 4-fluorophenyl |

In analogy to the preparation examples cited above and recited at the appropriate point, the compounds of the general formula specified hereinafter and shown in Table 3 are obtained.

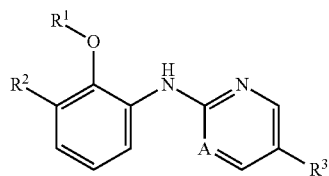

TABLE 3

| Example number | $R^2$ | $R^3$ | A | $R^1$ |
|---|---|---|---|---|
| 3-1 | H | F | CH | pyridin-2-yl |
| 3-2 | H | F | CH | 5-fluoropyridin-2-yl |
| 3-3 | H | F | CH | 5-chloropyridin-2-yl |
| 3-4 | H | Cl | CH | pyridin-2-yl |
| 3-5 | H | Cl | CH | 5-fluoropyridin-2-yl |
| 3-6 | H | Cl | CH | 5-chloropyridin-2-yl |
| 3-7 | F | F | CH | pyridin-2-yl |
| 3-8 | F | F | CH | 5-fluoropyridin-2-yl |
| 3-9 | F | F | CH | 5-chloropyridin-2-yl |
| 3-10 | F | Cl | CH | pyridin-2-yl |
| 3-11 | F | Cl | CH | 5-fluoropyridin-2-yl |
| 3-12 | F | Cl | CH | 5-chloropyridin-2-yl |
| 3-13 | Cl | F | CH | pyridin-2-yl |
| 3-14 | Cl | F | CH | 5-fluoropyridin-2-yl |
| 3-15 | Cl | F | CH | 5-chloropyridin-2-yl |
| 3-16 | Cl | Cl | CH | pyridin-2-yl |
| 3-17 | Cl | Cl | CH | 5-fluoropyridin-2-yl |
| 3-18 | Cl | Cl | CH | 5-chloropyridin-2-yl |
| 3-19 | CN | F | CH | pyridin-2-yl |
| 3-20 | CN | F | CH | 5-fluoropyridin-2-yl |
| 3-21 | CN | F | CH | 5-chloropyridin-2-yl |
| 3-22 | CN | Cl | CH | pyridin-2-yl |
| 3-23 | CN | Cl | CH | 5-fluoropyridin-2-yl |
| 3-24 | CN | Cl | CH | 5-chloropyridin-2-yl |
| 3-25 | H | F | N | pyridin-2-yl |
| 3-26 | H | F | N | 5-fluoropyridin-2-yl |
| 3-27 | H | F | N | 5-chloropyridin-2-yl |
| 3-28 | H | Cl | N | pyridin-2-yl |
| 3-29 | H | Cl | N | 5-fluoropyridin-2-yl |
| 3-30 | H | Cl | N | 5-chloropyridin-2-yl |
| 3-31 | F | F | N | pyridin-2-yl |
| 3-32 | F | F | N | 5-fluoropyridin-2-yl |
| 3-33 | F | F | N | 5-chloropyridin-2-yl |
| 3-34 | F | Cl | N | pyridin-2-yl |
| 3-35 | F | Cl | N | 5-fluoropyridin-2-yl |
| 3-36 | F | Cl | N | 5-chloropyridin-2-yl |
| 3-37 | Cl | F | N | pyridin-2-yl |
| 3-38 | Cl | F | N | 5-fluoropyridin-2-yl |
| 3-39 | Cl | F | N | 5-chloropyridin-2-yl |
| 3-40 | Cl | Cl | N | pyridin-2-yl |
| 3-41 | Cl | Cl | N | 5-fluoropyridin-2-yl |
| 3-42 | Cl | Cl | N | 5-chloropyridin-2-yl |
| 3-43 | CN | F | N | pyridin-2-yl |
| 3-44 | CN | F | N | 5-fluoropyridin-2-yl |
| 3-45 | CN | F | N | 5-chloropyridin-2-yl |
| 3-46 | CN | Cl | N | pyridin-2-yl |
| 3-47 | CN | Cl | N | 5-fluoropyridin-2-yl |
| 3-48 | CN | Cl | N | 5-chloropyridin-2-yl |
| 3-49 | H | Cl | N | pyridin-3-yl |
| 3-50 | H | Cl | N | 2-fluoropyridin-5-yl |
| 3-51 | H | Cl | N | 2-chloropyridin-5-yl |
| 3-52 | H | Cl | N | 2-trifluoromethylpyridin-5-yl |
| 3-53 | CN | F | N | 2-fluoropyridin-5-yl |
| 3-54 | CN | F | N | 2-chloropyridin-5-yl |
| 3-55 | CN | Cl | N | 2-fluoropyridin-5-yl |
| 3-56 | CN | Cl | N | 2-chloropyridin-5-yl |

The NMR data of disclosed examples are stated in classic form (δ values, number of hydrogen atoms, multiplet splitting).

NMR Data of the End Products (Classic Form)

1-40: $^1$H-NMR (400.0 MHz, d$_6$-DMSO):
δ = 8.83 (s, 1H); 8.12 (dd, 1H); 8.03 (m, 1H); 7.63 (dd, 1H); 7.22 (dt, 1H); 7.13 (m, 2H); 7.01 (dd, 1H); 6.97 (m, 1H); 6.68 (m, 2H) 1-75: $^1$H-NMR (400.0 MHz, d$_6$-DMSO):
δ = 8.77 (s, 1H); 8.14 (dd, 1H); 8.12 (m, 1H); 7.62 (dd, 1H); 7.26 (t, 1H); 7.20 (dd, 1H); 7.11 (m, 2H); 6.95 (dd, 1H); 6.79 (m, 2H) 1-79: $^1$H-NMR (400.0 MHz, d$_6$-DMSO):
δ = 8.47 (s, 1H); 8.07 (dd, 1H); 7.93 (d, 1H); 7.56 (dd, 1H); 7.13 (t, 1H); 7.08 (m, 2H); 6.96 (m, 1H); 6.87 (dd, 1H); 6.74 (m, 2H); 2.06 (s, 3H)
1-88: $^1$H-NMR (600.0 MHz, d$_6$-DMSO):
δ = 8.71 (s, 1H); 8.61 (dd, 1H); 8.13 (dd, 1H); 7.56 (m, 1H); 7.46 (dd, 1H); 7.39 (t, 1H); 7.15 (m, 2H); 6.94 (d, 1H); 6.87 (m, 2H); 6.81 (t, 1H)
1-106: $^1$H-NMR (600.0 MHz, d$_6$-DMSO):
δ = 8.81 (s, 1H); 8.52 (dd, 1H); 8.1 (d, 1H); 7.55 (ddd, 1H); 7.46 (dd, 1H); 7.39 (t, 1H); 7.14 (m, 2H); 6.99 (dd, 1H); 6.86 (m, 2H)
1-111: $^1$H-NMR (400.0 MHz, d$_6$-DMSO):
δ = 8.81 (s, 1H); 8.48 (dd, 1H); 8.21 (d, 1H); 7.55 (ddd, 1H); 7.46 (dd, 1H); 7.43-7.31 (m, 2H); 7.04 (m, 1H); 6.97 (dd, 1H); 6.67 (m, 1H)
1-124: $^1$H-NMR (600.0 MHz, d$_6$-DMSO):
δ = 8.94 (s, 1H); 8.47 (dd, 1H); 8.14 (d, 1H); 7.64 (dd, 1H); 7.52 (dd, 1H); 7.41 (t, 1H); 7.14 (m, 2H); 6.95 (d, 1H); 6.85 (m, 2H)
1-129: $^1$H-NMR (400.0 MHz, d$_6$-DMSO):
δ = 8.82 (s, 1H); 8.48 (dd, 1H); 8.13 (d, 1H); 7.66 (dd, 1H); 7.54 (dd, 1H); 7.44-7.30 (m, 2H); 7.03 (m, 1H); 6.92 (d, 1H); 6.60 (m, 1H)
1-139: $^1$H-NMR (600.0 MHz, d$_6$-DMSO):
δ = 8.64 (s, 1H); 7.97 (d, 1H); 7.93 (dd, 1H); 7.68 (dd, 1H); 7.44 (t, 1H); 7.38 (d, 1H); 7.08 (m, 2H); 6.72 (m, 2H)
1-143: $^1$H-NMR (600.0 MHz, d$_6$-DMSO):
δ = 8.94 (s, 1H); 8.46 (d, 1H); 8.20 (d, 1H); 7.73 (dd, 1H); 7.51 (dd, 1H); 7.41 (t, 1H); 7.14 (m, 2H); 6.90 (d, 1H); 6.85 (m, 2H)
1-144: $^1$H-NMR (400.0 MHz, d$_6$-DMSO):
δ = 8.95 (s, 1H); 8.44 (dd, 1H); 8.21 (d, 1H); 7.75 (dd, 1H); 7.55 (dd, 1H); 7.47-7.32 (m, 2H); 7.04 (m, 1H); 6.89 (d, 1H); 6.61 (m, 1H)

1-145: $^1$H-NMR (600.0 MHz, d$_6$-DMSO):
δ = 9.46 (s, 1H); 8.51 (d, 1H); 8.29 (dd, 1H); 7.88 (dd, 1H); 7.67 (dd, 1H); 7.46 (t, 1H); 7.12 (m, 2H); 6.88 (d, 1H); 6.82 (m, 2H)
1-146: $^1$H-NMR (400.0 MHz, d$_6$-DMSO):
δ = 10.98 (s, 1H); 8.68 (d, 1H); 8.14 (d, 1H); 8.04 (d, 1H); 7.83 (dd, 1H); 7.57 (t, 1H); 7.28-7.19 (m, 2H); 6.96-6.86 (m, 1H); 6.54 (m, 1H)
1-147: $^1$H-NMR (600.0 MHz, d$_6$-DMSO):
δ = 9.83 (s, 1H); 8.95 (d, 1H); 8.27 (dd, 1H); 8.25 (dd, 1H); 7.73 (dd, 1H); 7.49 (t, 1H); 7.11 (m, 2H); 6.87 (d, 1H); 6.83 (m, 2H)
1-149: $^1$H-NMR (600.0 MHz, d$_6$-DMSO):
δ = 8.62 (dd, 1H); 8.58 (s, 1H); 7.98 (s, 1H); 7.42-7.36 (m, 3H); 7.15 (m, 2H); 6.90-6.86 (m, 3H); 2.17 (s, 3H)
1-153: $^1$H-NMR (600.0 MHz, d$_6$-DMSO):
δ = 8.58 (dd, 1H); 8.53 (s, 1H); 7.98 (d, 1H); 7.37-7.31 (m, 2H); 7.30 (dd, 1H); 7.15 (m, 2H); 6.98 (d, 1H); 6.88 (m, 2H); 3.75 (s, 3H)
1-155: $^1$H-NMR (600.0 MHz, d$_6$-DMSO):
δ = 8.81 (s, 1H); 8.55 (dd, 1H); 8.10 (d, 1H); 7.60 (dd, 1H); 7.47 (dd, 1H); 7.39 (t, 1H); 7.14 (m, 2H); 6.93 (d, 1H); 6.86 (m, 2H); 2.42 (s, 3H)
1-204: $^1$H-NMR (600.0 MHz, d$_6$-DMSO):
δ = 9.21 (s, 1H); 8.44 (s, 2H); 7.66 (m, 1H); 7.28 (m, 1H); 7.15 (m, 1H); 7.10 (m, 1H); 6.83 (m, 2H)
1-235: $^1$H-NMR (600.0 MHz, d$_6$-DMSO):
δ = 9.12 (s, 1H); 8.45 (s, 2H); 7.82 (dd, 1H); 7.37 (d, 1H); 7.31 (t, 1H); 7.08 (m, 2H); 6.73 (m, 2H)
1-239: $^1$H-NMR (600.0 MHz, d$_6$-DMSO):
δ = 8.78 (s, 1H); 8.42 (s, 2H); 7.70 (dd, 1H); 7.18 (t, 1H); 7.09 (d, 1H); 7.07 (m, 2H); 6.72 (m, 2H); 2.09 (s, 3H)
1-246: $^1$H-NMR (400.0 MHz, d$_6$-DMSO):
δ = 9.10 (s, 1H); 8.42 (s, 2H); 8.21 (d, 1H); 7.74 (d, 1H); 7.47 (t, 1H); 7.27 (m, 1H); 7.08-6.99 ( m, 2H); 6.86 (m, 1H); 6.65 (m, 1H)
1-247: $^1$H-NMR (400.0 MHz, d$_6$-DMSO):
δ = 9.05 (s, 1H); 8.40 (d, 2H); 8.25 (d, 1H); 7.69 (d, 1H); 7.47 (t, 1H); 7.30 (m, 1H); 6.91-6.85 (m, 2H); 6.68 (m, 1H); 6.61 (m, 1H)
1-248: $^1$H-NMR (400.0 MHz, MeOD):
δ = 8.64 (dd, 1H); 8.43 (d, 2H); 7.49-7.41 (m, 2H); 7.03 (m, 2H); 6.92-6.87 (m, 3H)
1-249: $^1$H-NMR (400.0 MHz, d$_6$-DMSO):
δ = 9.11 (s, 1H); 8.40 (d, 2H); 8.23 (d, 1H); 7.68 (d, 1H); 7.49 (t, 1H); 7.30 (m, 1H); 7.10 (m, 1H); 6.86 (m, 2H); 6.75 dd, 1H)
1-250: $^1$H-NMR (400.0 MHz, d$_6$-DMSO):
δ = 9.04 (s, 1H); 8.40 (d, 2H); 8.26 (d, 1H); 7.68 (d, 1H); 7.47 (t, 1H); 7.33 (m, 2H); 6.86 (m, 1H); 6.81 (d, 2H)
1-251: $^1$H-NMR (400.0 MHz, d$_6$-DMSO):
δ = 9.17 (s, 1H); 8.40 (d, 2H); 8.17 (d, 1H); 7.68 (d, 1H); 7.47 (t, 1H); 7.37 (m, 1H); 6.92 (m, 1H); 6.86 (m, 1H); 6.74 (m, 1H)
1-252: $^1$H-NMR (400.0 MHz, d$_6$-DMSO):
δ = 9.24 (s, 1H); 8.39 (d, 2H); 8.12 (d, 1H); 7.71 (d, 1H); 7.46 (t, 1H); 7.31 (m, 1H); 6.92 (m, 1H); 6.85 (m, 1H); 6.54 (m, 1H)
1-253: $^1$H-NMR (400.0 MHz, CDCl$_3$):
δ = 9.01 (dd, 1H); 8.48 (d, 2H); 7.52 (s, 1H); 7.41-7.28 (m, 2H); 7.12 (m, 1H); 6.87 (m, 1H); 6.81 (m, 1H); 6.70 (m, 1H)
1-254: $^1$H-NMR (400.0 MHz, d$_6$-DMSO):
δ = 9.16 (s, 1H); 8.40 (d, 2H); 8.20 (d, 1H); 7.69 (d, 1H); 7.50 (t, 1H); 6.92 (m, 1H); 6.85 (m, 1H); 6.55 (m, 2H)
1-255: $^1$H-NMR (400.0 MHz, d$_6$-DMSO):
δ = 9.06 (s, 1H); 8.40 (d, 2H); 8.18 (d, 1H); 7.68 (d, 1H); 7.54-7.46 (m, 2H); 7.06 (m, 1H); 6.86 (m, 1H); 6.65 (dd, 1H)
1-256: $^1$H-NMR (400.0 MHz, d$_6$-DMSO):
δ = 9.24 (s, 1H); 8.40 (d, 2H); 8.19 (d, 1H); 7.70 (d, 1H); 7.53 (d, 1H); 7.46 (t, 1H); 7.10 (m, 1H); 6.86 (m, 1H); 6.69 (m, 1H)
1-259: $^1$H-NMR (400.0 MHz, CDCl$_3$):
δ = 9.00 (dd, 1H); 8.48 (d, 2H); 7.52 (s, 1H); 7.48-7.34 (m, 4H); 7.20 (s, 1H); 7.12 (dd, 1H); 6.86 (m, 1H)
1-260: $^1$H-NMR (400.0 MHz, d$_6$-DMSO):
δ = 9.17 (s, 1H); 8.39 (d, 2H); 8.28 (d, 1H); 7.68 (d, 1H); 7.64 (d, 2H); 7.51 (t, 1H); 6.98 (d, 2H); 6.86 (m, 1H)
1-261: $^1$H-NMR (300.0 MHz, d$_6$-DMSO):
δ = 9.17 (s, 1H); 8.34 (d, 2H); 8.22 (d, 1H); 7.76 (d, 2H); 7.68 (d, 1H); 7.49 (t, 1H); 6.93 (d, 2H); 6.83 (m, 1H)
1-262: $^1$H-NMR (400.0 MHz, d$_6$-DMSO):
δ = 8.87 (s, 1H); 8.42 (d, 2H); 8.29 (d, 1H); 7.65 (d, 1H); 7.44 (t, 1H); 7.15 (m, 1H); 6.86 (m, 1H); 6.61 (m, 1H); 6.38 (s, 1H); 6.31 (d, 1H); 3.34 (s, 3H)
1-265: $^1$H-NMR (400.0 MHz, d$_6$-DMSO):
δ = 9.29 (s, 1H); 8.49 (s, 2H); 8.10 (d, 1H); 7.68 (d, 1H); 7.48 (t, 1H); 7.26 (m, 1H); 7.10-7.00 (m, 2H); 6.64 (m, 1H)
1-266: $^1$H-NMR (400.0 MHz, d$_6$-DMSO):
δ = 9.24 (s, 1H); 8.49 (s, 2H); 8.16 (d, 1H); 7.70 (d, 1H); 7.46 (t, 1H); 7.31 (m, 1H); 6.89 (m, H); 6.67 (m, 1H); 6.60 (m, 1H)
1-267: $^1$H-NMR (600.0 MHz, d$_6$-DMSO):
δ = 9.15 (s, 1H); 8.48 (s, 2H); 8.14 (dd, 1H); 7.65 (dd, 1H); 7.45 (t, 1H); 7.10 (m, 2H); 6.79 (m, 2H)
1-268: $^1$H-NMR (400.0 MHz, d$_6$-DMSO):
δ = 9.28 (s, 1H); 8.49 (s, 2H); 8.14 (d, 1H); 7.74 (d, 1H); 7.49 (t, 1H); 7.30 (m, 1H); 7.10 (m, 1H); 6.84 (m, 1H); 6.74 dd, 1H)
1-269: $^1$H-NMR (400.0 MHz, d$_6$-DMSO):
δ = 9.23 (s, 1H); 8.49 (s, 2H); 8.15 (d, 1H); 7.69 (d, 1H); 7.45 (t, 1H); 7.32 (m, 2H); 6.79 (d, 2H)
1-270: $^1$H-NMR (400.0 MHz, d$_6$-DMSO):
δ = 9.33 (s, 1H); 8.50 (s, 2H); 8.07 (d, 1H); 7.68 (d, 1H); 7.48 (t, 1H); 7.36 (m, 1H); 6.92 (m, 1H); 6.74 (m, 1H)
1-271: $^1$H-NMR (400.0 MHz, d$_6$-DMSO):
δ = 9.39 (s, 1H); 8.49 (s, 2H); 8.06 (d, 1H); 7.73 (d, 1H); 7.48 (t, 1H); 7.31 (m, 1H); 6.90 (m, 1H); 6.55 (m, 1H)
1-272: $^1$H-NMR (600.0 MHz, d$_6$-DMSO):
δ = 9.25 (s, 1H); 8.49 (s, 2H); 8.11 (d, 1H); 7.68 (d, 1H); 7.47 (t, 1H); 7.33 (m, 1H); 6.96 (m, 1H); 6.58 (m, 1H)
1-273: $^1$H-NMR (600.0 MHz, d$_6$-DMSO):
δ = 9.33 (s, 1H); 8.50 (s, 2H); 8.11 (d, 1H); 7.70 (d, 1H); 7.49 (t, 1H); 6.94 (m, 1H); 6.54 (m, 2H)
1-274: $^1$H-NMR (400.0 MHz, d$_6$-DMSO):
δ = 9.25 (s, 1H); 8.50 (s, 2H); 8.06 (d, 1H); 7.68 (d, 1H); 7.54-7.46 (m, 2H); 7.06 (m, 1H); 6.63 (dd, 1H)
1-275: $^1$H-NMR (400.0 MHz, d$_6$-DMSO):
δ = 9.39 (s, 1H); 8.51 (s, 2H); 8.09 (d, 1H); 7.71 (d, 1H); 7.53 (m, 1H); 7.46 (t, 1H); 7.11 (m, 1H); 6.69 (m, 1H)
1-278: $^1$H-NMR (400.0 MHz, CDCl$_3$):
δ = 8.90 (dd, 1H); 8.35 (s, 2H); 7.51-7.34 (m,5H); 7.19 (s, 1H); 7.12 (m, 1H)
1-279: $^1$H-NMR (400.0 MHz, d$_6$-DMSO):
δ = 9.34 (s, 1H); 8.49 (s, 2H); 8.18 (d, 1H); 7.68 (d, 1H); 7.64 (d, 2H); 7.51 (t, 1H); 6.96 (d, 2H)
1-280: $^1$H-NMR (300.0 MHz, d$_6$-DMSO):
δ = 9.34 (s, 1H); 8.45 (s, 2H); 8.12 (d, 1H); 7.76 (d, 1H); 7.68 (d, 2H); 7.47 (t, 1H); 6.92 (d, 2H)
1-281: $^1$H-NMR (400.0 MHz, d$_6$-DMSO):
δ = 9.08 (s, 1H); 8.50 (s, 2H); 8.17 (d, 1H); 7.66 (d, 1H); 7.45 (t, 1H); 7.14 (m, 1H); 6.62 (m, 1H); 6.35 (s, 1H); 6.28 (d, 1H); 3.34 (s, 3H)
1-284: $^1$H-NMR (400.0 MHz, d$_6$-DMSO):
δ = 9.46 (s, 1H); 8.46 (s, 2H); 8.03 (d, 1H); 7.72 (d, 1H); 7.48 (t, 1H); 7.30 (m, 1H); 7.10-7.00 ( m, 2H); 6.65 (m, 1H)
1-285: $^1$H-NMR (400.0 MHz, d$_6$-DMSO):
δ = 9.43 (s, 1H); 8.47 (s, 2H); 8.08 (d, 1H); 7.70 (d, 1H); 7.49 (t, 1H); 7.29 (m, 1H); 6.89 (m, H); 6.66 (m, 1H); 6.59 (m, 1H)
1-286: $^1$H-NMR (600.0 MHz, d$_6$-DMSO):
δ = 9.35 (s, 1H); 8.45 (s, 2H); 8.08 (dd, 1H); 7.69 (dd, 1H); 7.45 (t, 1H); 7.10 (m, 2H); 6.79 (m, 2H)
1-287: $^1$H-NMR (400.0 MHz, d$_6$-DMSO):
δ = 9.47 (s, 1H); 8.46 (s, 2H); 8.07 (d, 1H); 7.74 (d, 1H); 7.49 (t, 1H); 7.32 (m, 1H); 7.10 (m, 1H); 6.83 (s, 1H); 6.75 d, 1H)
1-288: $^1$H-NMR (400.0 MHz, d$_6$-DMSO):
δ = 9.43 (s, 1H); 8.47 (s, 2H); 8.09 (d, 1H); 7.71 (d, 1H); 7.45 (t, 1H);

-continued 1-289: ¹H-NMR (400.0 MHz, d₆-DMSO):
δ = 9.51 (s, 1H); 8.47 (s, 2H); 8.02 (d, 1H); 7.72 (d, 1H); 7.48 (t, 1H);
7.35 (m, 1H); 6.93 (m, 1H); 6.74 (m, 1H)
1-290: ¹H-NMR (400.0 MHz, d₆-DMSO):
δ = 9.56 (s, 1H); 8.47 (s, 2H); 8.01 (d, 1H); 7.75 (d, 1H); 7.48 (t, 1H);
7.31 (m, 1H); 6.93 (m, 1H); 6.55 (m, 1H)
1-291: ¹H-NMR (600.0 MHz, d₆-DMSO):
δ = 9.43 (s, 1H); 8.46 (s, 2H); 8.06 (dd, 2H); 7.72 (dd, 1H); 7.48 (t, 1H); 7.33 (m, 1H); 6.95 (m, 1H); 6.58 (m, 1H)
1-292: ¹H-NMR (400.0 MHz, d₆-DMSO):
δ = 9.51 (s, 1H); 8.47 (s, 2H); 8.06 (d, 1H); 7.74 (d, 1H); 7.49 (t, 1H);
6.94 (m, 1H); 6.54 (m, 2H)
1-293: ¹H-NMR (400.0 MHz, d₆-DMSO):
δ = 9.43 (s, 1H); 8.47 (s, 2H); 8.01 (d, 1H); 7.74 (d, 1H); 7.54-7.46 (m, 2H); 7.06 (m, 1H); 6.63 (dd, 1H)
1-294: ¹H-NMR (400.0 MHz, d₆-DMSO):
δ = 9.55 (s, 1H); 8.47 (s, 2H); 8.03 (d, 1H); 7.75 (d, 1H); 7.53 (m, 1H); 7.46 (t, 1H); 7.11 (m, 1H); 6.70 (m, 1H)
1-297: ¹H-NMR (400.0 MHz, CDCl₃):
δ = 8.89 (dd, 1H); 8.40 (s, 2H); 7.52-7.35 (m,5H)? 7.19 (s, 1H); 7.11 (m, 1H)
1-298: ¹H-NMR (400.0 MHz, d₆-DMSO):
δ = 9.51 (s, 1H); 8.46 (s, 2H); 8.11 (d, 1H); 7.67 (d, 1H); 7.64 (d, 2H); 7.50 (t, 1H); 6.96 (d, 2H)
1-299: ¹H-NMR (300.0 MHz, d₆-DMSO):
δ = 9.50 (s, 1H); 8.42 (s, 2H); 8.07 (d, 1H); 7.74-7.66 (m, 3H); 7.47 (t, 1H); 6.91 (d, 2H)
1-300: ¹H-NMR (400.0 MHz, d₆-DMSO):
δ = 9.30 (s, 1H); 8.47 (s, 2H); 8.08 (d, 1H); 7.70 (d, 1H); 7.45 (t, 1H); 7.13 (m, 1H); 6.62 (m, 1H); 6.33 (s, 1H); 6.28 (d, 1H); 3.34 (s, 3H)
1-304: ¹H-NMR (600.0 MHz, d₆-DMSO):
δ = 10.11 (s, 1H); 8.76 (s, 2H); 8.92 (dd, 1H); 7.80 (dd, 1H); 7.48 (t, 1H); 7.08 (m, 2H); 6.77 (m, 2H)
1-305: ¹H-NMR (400.0 MHz, d₆-DMSO):
δ = 10.14 (s, 1H); 8.76 (s, 2H); 7.92 (dd, 1H); 7.82 (dd, 1H); 7.48 (t, 1H); 7.30 (m, 1H); 6.94 (m, 1H); 6.56 (m, 1H)
1-306: ¹H-NMR (600.0 MHz, d₆-DMSO):
δ = 10.50 (s, 1H); 9.12 (s, 1H); 7.94 (dd, 1H); 7.86 (dd, 1H); 7.51 (t, 1H); 7.09 (m, 2H); 6.79 (m, 2H)
1-308: ¹H-NMR (600.0 MHz, d₆-DMSO):
δ = 8.73 (s, 1H); 8.35 (dd, 1H); 8.28 (s, 2H); 7.59 (dd, 1H); 7.44 (t, 1H); 7.12 (m, 2H); 6.84 (m, 2H); 2.12 (s, 3H)
1-310: ¹H-NMR (600.0 MHz, d₆-DMSO):
δ = 8.76 (s, 1H); 8.35 (dd, 1H); 8.31 (s, 2H); 7.59 (dd, 1H); 7.44 (t, 1H); 7.11 (m, 2H); 6.83 (m, 2H); 2.49 (q, 2H); 1.14 (s, 3H)
1-312: ¹H-NMR (600.0 MHz, d₆-DMSO):
δ = 8.66 (s, 1H); 8.35 (dd, 1H); 8.25 (s, 2H); 7.55 (dd, 1H); 7.43 (t, 1H); 7.12 (m, 2H); 6.83 (m, 2H); 3.80 (s, 3H)
1-314: ¹H-NMR (600.0 MHz, d₆-DMSO):
δ = 9.26 (s, 1H); 8.37 (s, 2H); 8.13 (dd, 1H); 7.67 (dd, 1H); 7.45 (t, 1H); 7.12 (t, 1H); 7.09 (m, 2H); 6.79 (m, 2H)
1-318: ¹H-NMR (600.0 MHz, d₆-DMSO):
δ = 9.17 (s, 1H); 8.42 (s, 2H); 8.17 (dd, 1H); 7.66 (dd, 1H); 7.45 (t, 1H); 7.10 (m, 2H); 6.80 (m, 2H); 2.42 (s, 3H)
1-324: ¹H-NMR (600.0 MHz, d₆-DMSO):
δ = 8.78 (s, 1H); 8.42 (s, 2H); 7.49 (dd, 1H); 7.22 (t, 1H); 7.05 (m, 2H); 6.95 (dd, 1H); 6.73 (m, 2H); 3.71 (s, 3H)
1-328: ¹H-NMR (400.0 MHz, d₆-DMSO):
δ = 8.89 (s, 1H); 8.42 (s, 2H); 7.62 (dd, 1H); 7.28 (t, 1H); 7.12 (dd, 1H); 7.04 (m, 2H); 6.69 (m, 2H); 2.39 (s, 3H)
1-330: ¹H-NMR (600.0 MHz, d₆-DMSO):
δ = 8.88 (s, 1H); 8.52 (dd, 1H); 8.04 (d, 1H); 7.51 (dd, 1H); 7.48 (dd, 1H); 7.40 (t, 1H); 7.14 (m, 2H); 7.10 (t, 1H); 6.99 (d, 1H); 6.86 (m, 2H)
1-332: ¹H-NMR (600.0 MHz, d₆-DMSO):
δ = 9.03 (s, 1H); 8.46 (dd, 1H); 8.18 (d, 1H); 7.65 (dd, 1H); 7.54 (dd, 1H); 7.42 (t, 1H); 7.13 (m, 2H); 6.99 (d, 1H); 6.84 (m, 2H)
1-334: ¹H-NMR (600.0 MHz, d₆-DMSO):
δ = 9.28 (s, 1H); 8.36 (dd, 1H); 8.32 (d, 1H); 7.81 (dd, 1H); 7.62 (dd, 1H); 7.45 (t, 1H); 7.11 (m, 2H); 6.93 (d, 1H); 6.82 (m, 2H)
1-336: ¹H-NMR (600.0 MHz, d₆-DMSO):
δ = 8.91 (s, 1H); 8.44 (s, 2H); 7.80 (dd, 1H); 7.33 (m, 2H);
7.17-7.07 (m, 3H); 6.95-6.92 (m, 3H)
1-337: ¹H-NMR (400.0 MHz, d₆-DMSO):
δ = 8.99 (s, 1H); 8.44 (s, 2H); 7.77 (m, 1H); 7.19-7.10 (m, 3H); 6.99 (m, 2H); 6.90 (m, 1H)
1-339: ¹H-NMR (600.0 MHz, d₆-DMSO):
δ = 9.16 (s, 1H); 8.39 (s, 2H); 7.77-7.75 (m, 3H); 7.27 (m, 1H); 7.22 (m, 1H); 7.14 dd, 1H). 6.99 (dd, 2H)
1-340: ¹H-NMR (600.0 MHz, d₆-DMSO):
δ = 9.03 (s, 1H); 8.45 (s, 2H); 7.84 (dd, 1H); 7.36 (dd, 1H); 7.31 (t, 1H). 7.25 (dd, 2H); 6.99 (t, 1H); 6.72 (d, 2H)
1-341: ¹H-NMR (600.0 MHz, d₆-DMSO):
δ = 9.18 (s, 1H); 8.45 (s, 2H); 7.81 (dd, 1H); 7.38 (dd, 1H); 7.33-7.29 (m, 3H); 6.99 (t, 1H); 6.73 (ddd, 2H)
1-342: ¹H-NMR (600.0 MHz, d₆-DMSO):
δ = 8.58 (dd, 1H); 8.52 (s, 1H); 7.86 (d, 1H); 7.37-7.35 (m, 2H); 7.29 (dd, 1H); 7.15 (m, 2H); 6.95 (d, 1H); 6.88 (m, 2H); 4.45 (m, 1H); 1.24 (d, 6H)
1-344: ¹H-NMR (600.0 MHz, d₆-DMSO):
δ = 8.66 (s, 1H); 8.35 (dd, 1H); 8.22 (s, 2H); 7.56 (dd, 1H); 7.43 (t, 1H). 7.12 (m, 2H). 6.83 (m, 2H). 4.45 (m, 1H); 1.25 (d,6H)
1-350: ¹H-NMR (600.0 MHz, d₆-DMSO):
δ = 9.36 (s, 1H); 8.47 (d, 2H); 8.10 (dd, 1H); 7.83 (dd, 1H); 7.50 (t, 1H); 7.07 (m, 2H); 6.75 (m, 2H)
1-354: ¹H-NMR (600.0 MHz, d₆-DMSO):
δ = 8.53 (s, 1H); 8.39 (s, 2H); 7.06-7.03 (m, 3H); 6.94 (t, 1H); 6.77 (m, 2H); 6.59 (dd, 1H); 4.93 (s, 2H)
1-358: ¹H-NMR (600.0 MHz, d₆-DMSO):
δ = 9.10 (s, 1H); 8.45 (s, 2H); 7.83 (dd, 1H); 7.51 (dd, 1H); 7.24 (t, 1H); 7.08 (m, 2H); 6.70 (m, 2H)
1-360: ¹H-NMR (600.0 MHz, d₆-DMSO):
δ = 8.58 (dd, 1H); 8.52 (s, 1H); 7.88 (d, 1H); 7.37-7.34 (m, 2H); 7.29 (dd, 1H); 7.15 (m, 2H); 6.97 (d, 1H); 6.88 (m, 2H); 4.01 (q, 2H); 1.30 (t, 3H)
1-362: ¹H-NMR (600.0 MHz, d₆-DMSO):
δ = 8.64 (s, 1H); 8.35 (dd, 1H); 8.23 (s, 2H); 7.56 (dd, 1H); 7.43 (t, 1H); 7.12 (m, 2H); 6.83 (m, 2H); 4.06 (q, 2H); 1.31 (t, 3H)
1-364: ¹H-NMR (600.0 MHz, d₆-DMSO):
δ = 10.98 (s, 1H); 8.64 (s, 2H); 7.83 (t, 1H); 7.70 (d, 1H); 7.67 (d, 1H); 7.56 (d, 1H); 7.14 (dd, 1H); 7.07 (t, 1H)
1-365: ¹H-NMR (600.0 MHz, d₆-DMSO):
δ = 8.57 (s, 1H); 8.39 (s, 2H); 7.08-7.02 (m, 4H); 6.73 (m, 2H); 6.47 (d, 2H); 5.23 (q, 1H); 2.68 (d, 3H)
1-366: ¹H-NMR (600.0 MHz, d₆-DMSO):
δ = 8.64 (s, 1H); 8.41 (s, 2H); 7.70 (d, 1H); 7.47 (dd, 1H); 7.15 (t, 1H); 7.03 (m, 2H); 6.81 (dd, 1H); 6.7 (m, 2H); 2.68 (s, 6H)
1-367: ¹H-NMR (600.0 MHz, d₆-DMSO):
δ = 9.87 (s, 1H); 9.82 (d, 1H); 8.91 (s, 1H); 8.40 (s, 2H); 8.05 (d, 1H); 7.46 (d, 1H); 7.22 (t, 1H); 7.04 (m, 2H); 6.70 (m, 2H)
1-368: ¹H-NMR (600.0 MHz, d₆-DMSO):
δ = 9.44 (s, 1H); 8.95 (s, 1H); 8.40 (s, 2H); 7.70 (d, 1H); 7.48 (d, 1H); 7.21 (t, 1H); 7.04 (m, 2H); 6.72 (m, 2H); 1.90 (s, 3H)
1-369: ¹H-NMR (600.0 MHz, d₆-DMSO):
δ = 9.11 (s, 1H); 8.46 (s, 2H); 7.87 (d, 1H); 7.33 (t, 1H); 7.22 (dd, 1H); 7.06 (m, 2H); 6.72 (m, 2H); 2.84 (s, 3H); 1.71 (s, 3H)
1-372: ¹H-NMR (600.0 MHz, d₆-DMSO):
δ = 9.02 (s, 1H); 8.43 (s, 2H); 7.84 (dd, 1H); 7.68 (dd, 1H); 7.08 (t, 1H); 7.07 (m, 2H); 6.70 (m, 2H)
1-374: ¹H-NMR (600.0 MHz, d₆-DMSO):
δ = 9.41 (s, 1H); 8.51 (s, 2H); 8.11 (dd, 1H); 7.70 (dd, 1H); 7.48 (t, 1H); 7.17 (m, 1H); 6.56 (m, 1H)
1-375: ¹H-NMR (600.0 MHz, d₆-DMSO):
δ = 9.35 (s, 1H); 8.49 (s, 2H); 8.04 (dd, 1H); 7.70 (dd, 1H); 7.68 (m, 1H); 7.46 (t, 1H). 6.95 (m, 1H)
1-376: ¹H-NMR (600.0 MHz, d₆-DMSO):
δ = 8.87 (s, 1H); 8.42 (s, 2H); 7.63 (dd, 1H); 7.28 (t, 1H); 7.18 (dd, 1H); 7.03 (m, 2H); 6.69 (m, 2H); 2.93 (q, 2H); 1.20 (t, 3H)
2-101: ¹H-NMR (400.0 MHz, d₆-DMSO):
δ = 9.08 (s, 1H); 8.39 (s, 2H); 8.27 (s, 1H); 7.43 (s, 2H); 7.07 (m, 2H); 6.76 (m, 2H)
2-103: ¹H-NMR (400.0 MHz, d₆-DMSO):
δ = 13.29 (brs, 1H); 9.26 (s, 1H); 8.56 (s, 2H); 8.11 (d, 1H);

-continued 7.80 (d, 1H); 7.11 (m, 2H); 6.78 (m, 2H)
2-105: $^1$H-NMR (600.0 MHz, d$_6$-DMSO):
δ = 9.32 (s, 1H); 8.57 (s, 2H); 8.18 (d, 1H); 7.82 (d, 1H); 7.12 (m, 2H); 6.77 (m, 2H); 3.85 (s, 3H)
2-130: $^1$H-NMR (600.0 MHz, d$_6$-DMSO):
δ = 9.02 (s, 1H); 8.47 (s, 2H); 8.21 (s, 1H); 7.40 (s, 2H); 7.31 (m, 2H); 7.21 (m, 2H); 6.24 (s, 1H)
2-131: $^1$H-NMR (400.0 MHz, d$_6$-DMSO):
δ = 8.63 (s, 1H); 8.29 (s, 2H); 7.14 (m, 2H); 7.08 (d, 1H); 6.96 (m, 2H); 6.32 (dd, 1H); 6.08 (d, 1H); 5.12 (s, 2H)
2-132: $^1$H-NMR (600.0 MHz, d$_6$-DMSO):
δ = 9.62 (s, 1H); 8.91 (s, 1H); 8.38 (s, 2H); 7.49 (d, 1H); 7.19-7.13 (m, 4H); 6.98 (m, 2H); 4.06 (q, 2H); 1.20 (t, 3H)
2-133: $^1$H-NMR (600.0 MHz, d$_6$-DMSO):
δ = 12.88 (brs, 1H); 9.18 (s, 1H); 8.58 (s, 2H); 8.16 (d, 1H); 7.71 (dd, 1H); 7.30 (d, 1H); 7.25 (m, 2H); 7.13 (m, 2H)
2-134: $^1$H-NMR (600.0 MHz, d$_6$-DMSO):
δ = 9.23 (s, 1H); 8.60 (s, 2H); 8.22 (d, 1H); 7.76 (dd, 1H); 7.32 (d, 1H); 7.26 (m, 2H); 7.12 (m, 2H); 3.78 (s, 3H)
2-135: $^1$H-NMR (600.0 MHz, d$_6$-DMSO):
δ = 8.37 (s, 1H); 8.31 (s, 2H); 7.14-7.11 (m, 3H); 6.94 (m, 2H); 6.31 (dd, 1H); 6.08 (d, 1H); 5.07 (s, 2H)
2-136: $^1$H-NMR (600.0 MHz, d$_6$-DMSO):
δ = 9.59 (s, 1H); 8.67 (s, 1H); 8.41 (s, 2H); 7.57 (d, 1H); 7.19-7.14 (m, 4H); 6.98 (m, 2H); 4.06 (q, 2H); 1.20 (t, 3H)
2-137: $^1$H-NMR (600.0 MHz, d$_6$-DMSO):
δ = 8.98 (s, 1H); 8.62 (s, 2H); 8.27 (d, 1H); 7.72 (dd, 1H); 7.30 (d, 1H); 7.25 (m, 2H); 7.13 (m, 2H)
2-138: $^1$H-NMR (400.0 MHz, d$_6$-DMSO):
δ = 9.04 (s, 1H); 8.63 (d, 2H); 8.32 (d, 1H); 7.75 (dd, 1H); 7.32 (d, 1H); 7.26 (m, 2H); 7.13 (m, 2H); 3.78 (s, 3H)
2-139: $^1$H-NMR (400.0 MHz, d$_6$-DMSO):
δ = 9.19 (s, 1H); 8.48 (d, 2H); 7.86 dd, 1H); 7.70 (d, 1H); 7.09 (m, 2H); 6.73 (m, 2H)
2-140: $^1$H-NMR (600.0 MHz, d$_6$-DMSO):
δ = 8.55 (s, 1H); 8.38 (s, 2H); 7.55 (s, 1H); 7.16 (m, 2H); 6.99 (m, 2H); 6.34 (s, 1H)
2-141: $^1$H-NMR (600.0 MHz, d$_6$-DMSO):
δ = 9.72 (s, 1H); 9.33 (s, 1H); 8.56 (s, 2H); 8.56 (s, 1H); 7.32 (m, 2H); 7.28 (s, 1H); 7.23 (m, 2H); 4.07 (q, 2H); 1.18 (t, 3H)
3-49: $^1$H-NMR (600.0 MHz, d$_6$-DMSO):
δ = 9.15 (s, 1H); 8.41 (s, 2H); 8.29-8.27 (m, 2H); 7.75 (dd, 1H); 7.34 (dd, 1H); 7.29 (m, 1H); 7.23-7.16 (m, 2H); 7.02 (m, 1H)
3-53: $^1$H-NMR (600.0 MHz, d$_6$-DMSO):
δ = 9.39 (s, 1H); 8.48 (s, 2H); 8.11 (dd, 1H); 7.78 (m, 1H); 7.69 (d, 1H); 7.48 (t, 1H); 7.42 (m, 1H); 7.11 (dd, 1H)
3-54: $^1$H-NMR (400.0 MHz, d$_6$-DMSO):
δ = 9.44 (s, 1H); 8.49 (d, 2H); 8.13 (dd, 1H); 8.01 (d, 1H); 7.70 (dd, 1H); 7.48 (t, 1H); 7.40 (dd, 1H); 7.28 (dd, 1H)
3-55: $^1$H-NMR (600.0 MHz, d$_6$-DMSO):
δ = 9.56 (s, 1H); 8.46 (s, 2H); 8.06 (dd, 1H); 7.78 (m, 1H); 7.72 (d, 1H); 7.48 (t, 1H); 7.42 (m, 1H); 7.10 (dd, 1H)
3-56: $^1$H-NMR (600.0 MHz, d$_6$-DMSO):
δ = 9.59 (s, 1H); 8.46 (s, 2H); 8.08 (dd, 1H); 8.01 (d, 1H); 7.74 (dd, 1H); 7.49 (t, 1H); 7.41 (d, 1H); 7.28 (dd, 1H)

The present invention further provides for the use of one or more compounds of the general formula (I) and/or salts thereof, as defined above, preferably in one of the embodiments identified as preferred or particularly preferred, in particular one or more compounds of the formulae 1-1 to 1-376, 2-1 to 2-141, 3-1 to 3-56 and/or salts thereof, in each case as defined above, as herbicide and/or plant growth regulator, preferably in crops of useful plants and/or ornamentals.

The present invention further provides a method for controlling harmful plants and/or for regulating the growth of plants, characterized in that an effective amount
of one or more compounds of the general formula (I) and/or salts thereof, as defined above, preferably in one of the embodiments identified as preferred or particularly preferred, in particular one or more compounds of the formulae 1-1 to 1-376, 2-1 to 2-141, 3-1 to 3-56 and/or salts thereof, in each case as defined above, or
of a composition according to the invention, as defined below,
is applied to the (harmful) plants, seeds of (harmful) plants, the soil in which or on which the (harmful) plants grow or the area under cultivation.

The present invention also provides a method for controlling unwanted plants, preferably in crops of useful plants, characterized in that an effective amount
of one or more compounds of the general formula (I) and/or salts thereof, as defined above, preferably in one of the embodiments identified as preferred or particularly preferred, in particular one or more compounds of the formulae 1-1 to 1-376, 2-1 to 2-141, 3-1 to 3-56 and/or salts thereof, in each case as defined above, or
of a composition according to the invention, as defined below,
is applied to unwanted plants (for example harmful plants such as mono- or dicotyledonous weeds or unwanted crop plants), the seed of the unwanted plants (i.e. plant seeds, for example grains, seeds or vegetative propagation organs such as tubers or shoot parts with buds), the soil in which or on which the unwanted plants grow (for example the soil of crop land or non-crop land) or the area under cultivation (i.e. the area on which the unwanted plants will grow).

The present invention also further provides methods for controlling for regulating the growth of plants, preferably of useful plants, characterized in that an effective amount
of one or more compounds of the general formula (I) and/or salts thereof, as defined above, preferably in one of the embodiments identified as preferred or particularly preferred, in particular one or more compounds of the formulae 1-1 to 1-376, 2-1 to 2-141, 3-1 to 3-56 and/or salts thereof, in each case as defined above, or
of a composition according to the invention, as defined below,
is applied to the plant, the seed of the plant (i.e. plant seed, for example grains, seeds or vegetative propagation organs such as tubers or shoot parts with buds), the soil in which or on which the plants grow (for example the soil of crop land or non-crop land) or the area under cultivation (i.e. the area on which the plants will grow).

In this context, the compounds according to the invention or the compositions according to the invention can be applied for example by pre-sowing (if appropriate also by incorporation into the soil), pre-emergence and/or post-emergence processes. Specific examples of some representatives of the monocotyledonous and dicotyledonous weed flora which can be controlled by the compounds according to the invention are as follows, though there is no intention to restrict the enumeration to particular species.

In a method according to the invention for controlling harmful plants or for regulating the growth of plants, one or more compounds of the general formula (I) and/or salts thereof are preferably employed for controlling harmful plants or for regulating growth in crops of useful plants or ornamental plants, where in a preferred embodiment the useful plants or ornamental plants are transgenic plants.

The compounds of the general formula (I) according to the invention and/or their salts are suitable for controlling the following genera of monocotyledonous and dicotyledonous harmful plants:

Monocotyledonous harmful plants of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fim-

*bristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Dicotyledonous harmful plants of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

When the compounds of the general formula (I) according to the invention are applied to the soil surface before germination of the harmful plants (weed grasses and/or broad-leaved weeds) (pre-emergence method), either the seedlings of the weed grasses or broad-leaved weeds are prevented completely from emerging or they grow until they have reached the cotyledon stage, but then stop growing and eventually, after three to four weeks have elapsed, die completely.

If the active compounds of the general formula (I) are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a sustained manner.

Although the compounds of the general formula (I) according to the invention display outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, are damaged only to an insignificant extent, or not at all, depending on the structure of the respective compound according to the invention and its application rate. For these reasons, the present compounds are very suitable for selective control of unwanted plant growth in plant crops such as agriculturally useful plants or ornamental plants.

In addition, the compounds of the general formula (I) according to the invention (depending on their particular structure and the application rate deployed) have outstanding growth-regulating properties in crop plants. They intervene in the plants' own metabolism with regulatory effect, and can thus be used for the controlled influencing of plant constituents and to facilitate harvesting, for example by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since, for example, this can reduce or completely prevent lodging.

By virtue of their herbicidal and plant growth regulatory properties, the active compounds of the general formula (I) can also be used to control harmful plants in crops of genetically modified plants or plants modified by conventional mutagenesis. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material.

It is preferred with a view to transgenic crops to use the compounds of the general formula (I) according to the invention and/or their salts in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables.

It is preferable to employ the compounds of the general formula (I) according to the invention also as herbicides in crops of useful plants which are resistant, or have been made resistant by recombinant means, to the phytotoxic effects of the herbicides.

By virtue of their herbicidal and plant growth regulatory properties, the compounds of the general formula (I) according to the invention can also be used to control harmful plants in crops of genetically modified plants which are known or are yet to be developed. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material. Further special properties may be tolerance or resistance to abiotic stressors, for example heat, cold, drought, salinity and ultraviolet radiation.

Preference is given to the use of the compounds of the general formula (I) according to the invention or salts thereof in economically important transgenic crops of useful plants and ornamentals, for example of cereals such as wheat, barley, rye, oats, triticale, millet, rice, cassava and corn, or else crops of sugar beet, cotton, soybean, oilseed rape, potatoes, tomatoes, peas and other vegetables.

It is preferable to employ the compounds of the general formula (I) as herbicides in crops of useful plants which are resistant, or have been made resistant by recombinant means, to the phytotoxic effects of the herbicides.

Conventional ways of producing novel plants which have modified properties in comparison to existing plants consist, for example, in traditional cultivation methods and the generation of mutants. Alternatively, novel plants with altered properties can be generated with the aid of recombinant methods.

A large number of molecular-biological techniques by means of which novel transgenic plants with modified properties can be generated are known to the person skilled in the art. For such genetic manipulations, nucleic acid molecules which allow mutagenesis or sequence alteration by recombination of DNA sequences can be introduced into plasmids. With the aid of standard methods, it is possible, for example, to undertake base exchanges, remove part sequences or add natural or synthetic sequences. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

It is preferable to employ the compounds of the general formula (I) according to the invention in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, glyphosates, glufosinates or benzoylisoxazoles and analogous active compounds.

When the compounds of the general formula (I) according to the invention are employed in transgenic crops, not only do the effects toward harmful plants observed in other crops occur, but frequently also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the general formula (I) according to the invention and/or their salts as herbicides for controlling harmful plants in crops of useful plants or ornamentals, optionally in transgenic crop plants.

Preference is given to the use of compounds of the general formula (I) in cereals, here preferably corn, wheat, barley, rye, oats, millet or rice, by the pre- or post-emergence method.

Preference is also given to the use of compounds of the general formula (I) in soybean by the pre-emergence or post-emergence method.

The use of inventive compounds of the formula (I) for the control of harmful plants or for growth regulation of plants also includes the case in which a compound of the general formula (I) or its salt is not formed from a precursor substance ("prodrug") until after application on the plant, in the plant or in the soil.

The invention also provides the use of one or more compounds of the general formula (I) or salts thereof or of a composition according to the invention (as defined below) (in a method) for controlling harmful plants or for regulating the growth of plants which comprises applying an effective amount of one or more compounds of the general formula (I) or salts thereof onto the plants (harmful plants, if appropriate together with the useful plants), plant seeds, the soil in which or on which the plants grow or the area under cultivation.

The invention also provides a herbicidal and/or plant growth-regulating composition, characterized in that the composition comprises
(a) one or more compounds of the general formula (I) and/or salts thereof, as defined above, preferably in one of the embodiments identified as preferred or particularly preferred, in particular one or more compounds of the formulae
1-1 to 1-376, 2-1 to 2-141, 3-1 to 3-56 and/or salts thereof, in each case as defined above, and
(b) one or more further substances selected from groups (i) and/or (ii):
(i) one or more further agrochemically active substances, preferably selected from the group consisting of insecticides, acaricides, nematicides, further herbicides (i.e. those not conforming to the general formula (I) defined above), fungicides, safeners, fertilizers and/or further growth regulators,
(ii) one or more formulation auxiliaries customary in crop protection.

Here, the further agrochemically active substances of component (i) of a composition according to the invention are preferably selected from the group of substances mentioned in "The Pesticide Manual", 16th edition, The British Crop Protection Council and the Royal Soc. of Chemistry, 2012.

A herbicidal or plant growth-regulating composition according to the invention comprises preferably one, two, three or more formulation auxiliaries (ii) customary in crop protection selected from the group consisting of surfactants, emulsifiers, dispersants, film-formers, thickeners, inorganic salts, dusting agents, carriers solid at 25° C. and 1013 mbar, preferably adsorptive granulated inert materials, wetting agents, antioxidants, stabilizers, buffer substances, antifoam agents, water, organic solvents, preferably organic solvents miscible with water in any ratio at 25° C. and 1013 mbar.

The compounds of the general formula (I) according to the invention can be used in the form of wettable powders, emulsifiable concentrates, sprayable solutions, dusting products or granules in the customary formulations. The invention therefore also provides herbicidal and plant growth-regulating compositions which comprise compounds of the general formula (I) and/or salts thereof.

The compounds of the general formula (I) according to the invention and/or salts thereof can be formulated in various ways according to which biological and/or physicochemical parameters are specified. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types and the formulation assistants, such as inert materials, surfactants, solvents and further additives, are known to the person skilled in the art and are described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Technology], volume 7, C. Hanser Verlag Munich, 4th Ed. 1986.

Wettable powders are preparations which can be dispersed uniformly in water and, in addition to the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidal active compounds are finely ground, for example in customary apparatuses such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonate salts, for example calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely distributed solids, for example talc, natural clays, such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as have, for example, already been listed above for the other formulation types.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or else mineral oils. Suitable active compounds can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray-Drying Handbook" 3rd Ed. 1979, G. Goodwin Ltd., London; J. E. Browning, "Agglomeration", Chemical and Engineering 1967, pages 147 ff; "Perry's Chemical Engineer's Handbook", 5th Ed., McGraw Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations, preferably herbicidal or plant growth-regulating compositions, of the present invention preferably comprise a total amount of from 0.1 to 99% by weight, preferably 0.5 to 95% by weight, particularly preferably 1 to 90% by weight, especially preferably 2 to 80% by weight, of active compounds of the general formula (I) and their salts.

In wettable powders, the active compound concentration is, for example, about 10% to 90% by weight, the remainder to 100% by weight consisting of customary formulation constituents. In emulsifiable concentrates, the active compound concentration may be about 1% to 90% and preferably 5% to 80% by weight. Formulations in the form of dusts comprise 1% to 30% by weight of active compound, preferably usually 5% to 20% by weight of active compound; sprayable solutions contain about 0.05% to 80% by weight, preferably 2% to 50% by weight of active compound. In the case of water-dispersible granules, the active compound content depends partially on whether the active compound is in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described inter alia in "Chemistry and Technology of Agrochemical Formulations", ed. D. A. Knowles, Kluwer Academic Publishers (1998).

The compounds of the general formula (I) according to the invention or salts thereof can be used as such or in the form of their preparations (formulations) in a combination with other pesticidally active substances, for example insecticides, acaricides, nematicides, herbicides, fungicides, safeners, fertilizers and/or growth regulators, for example in the form of a finished formulation or of a tank mix. The combination formulations can be prepared on the basis of the abovementioned formulations, while taking account of the physical properties and stabilities of the active compounds to be combined.

Active compounds which can be employed in combination with the compounds of the general formula (I) according to the invention in mixture formulations or in a tank mix are, for example, known active compounds based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as described, for example, in Weed Research 26 (1986) 441-445 or "The Pesticide Manual", 16th edition, The British Crop Protection Council and the Royal Soc. of Chemistry, 2012 and literature cited therein.

Of particular interest is the selective control of harmful plants in crops of useful plants and ornamentals. Although the compounds of the general formula (I) according to the invention have already demonstrated very good to adequate selectivity in a large number of crops, in principle, in some crops and in particular also in the case of mixtures with other, less selective herbicides, phytotoxicities on the crop plants may occur. In this connection, combinations of compounds (I) according to the invention that are of particular interest are those which comprise the compounds of the general formula (I) or their combinations with other herbicides or pesticides and safeners. The safeners, which are used in an antidotically effective amount, reduce the phytotoxic side effects of the herbicides/pesticides employed, for example in economically important crops, such as cereals (wheat, barley, rye, corn, rice, millet), sugarbeet, sugarcane, oilseed rape, cotton and soybeans, preferably cereals.

The weight ratios of herbicide (mixture) to safener depend generally on the herbicide application rate and the efficacy of the safener in question and may vary within wide limits, for example in the range from 200:1 to 1:200, preferably 100:1 to 1:100, in particular 20:1 to 1:20. Analogously to the compounds of the general formula (I) or mixtures thereof, the safeners can be formulated with further herbicides/pesticides and be provided and employed as a finished formulation or tank mix with the herbicides.

For application, the herbicide or herbicide/safener formulations present in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The application rate of the compounds of the general formula (I) and/or their salts is affected to a certain extent by external conditions such as temperature, humidity, etc. Here, the application rate may vary within wide limits. For the application as a herbicide for controlling harmful plants, the total amount of compounds of the general formula (I) and their salts is preferably in the range from 0.001 to 10.0 kg/ha, with preference in the range from 0.005 to 5 kg/ha, more preferably in the range from 0.01 to 1.5 kg/ha, particularly preferably in the range from 0.05 to 1 kg/ha. This applies both to the pre-emergence and the post-emergence application.

When the compounds of the general formula (I) according to the invention and/or their salts are used as plant growth regulator, for example as culm stabilizer for crop plants like those mentioned above, preferably cereal plants, such as wheat, barley, rye, triticale, millet, rice or corn, the total application rate is preferably in the range of from 0.001 to 2 kg/ha, preferably in the range of from 0.005 to 1 kg/ha, in particular in the range of from 10 to 500 g/ha, very particularly preferably in the range from 20 to 250 g/ha. This applies both to the pre-emergence and the post-emergence application.

The application as culm stabilizer may take place at various stages of the growth of the plants. Preferred is, for example, the application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

Active compounds which can be employed in combination with the compounds of the general formula (I) according to the invention in compositions according to the invention (for example in mixed formulations or in the tank mix) are, for example, known active compounds which are based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II or protoporphyrinogen oxidase, as are described in, for example, Weed Research 26 (1986) 441-445 or "The Pesticide Manual", 16th edition, The British Crop Protection Council and the Royal Soc. of Chemistry, 2012 and the literature cited therein. Known herbicides or plant growth regulators which can be combined with the compounds of the invention are, for example, the following, where said active compounds are designated either with their "common name" in accordance with the International Organization for Standardization (ISO) or with the chemical name or with the code number. They always encompass all the use forms, for example acids, salts, esters and also all isomeric forms such as stereoisomers and optical isomers, even if they are not mentioned explicitly.

Examples of such herbicidal mixing partners are:
acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammonium sulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyrimorate, cyclosulfamuron, cycloxydim, cyhalofop, cyhalofop-butyl, cyprazine, 2,4-D, 2,4-D-butotyl, -butyl, -dimethylammonium, -diolamine, -ethyl, 2-ethylhexyl, -isobutyl, -isooctyl, -isopropylammonium, -potassium, -triisopropanolammonium and -trolamine, 2,4-DB, 2,4-DB-butyl, -dimethylammonium, isooctyl, -potassium and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-9600, F-5231, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl)O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl) ethyl (2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium, and -butotyl, mecoprop-P, mecoprop-P-butotyl, -dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazasulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinate, monolinuron, monosulfuron, monosulfuron-ester, MT-5950, i.e. N-[3-chloro-4-(1-methylethyl)phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorophenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trifluoroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy]benzyl}aniline, and the following compounds:

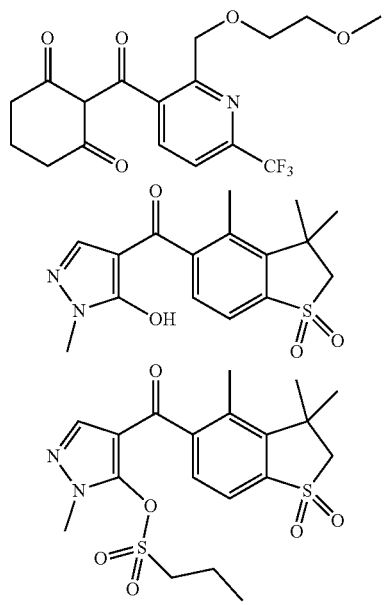

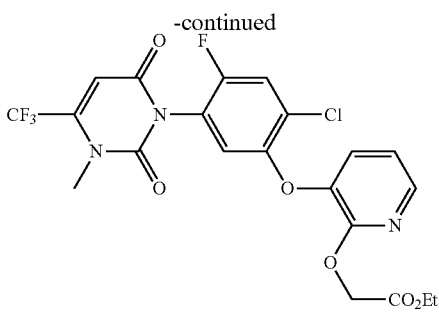

Examples of plant growth regulators as possible mixing partners are:

acibenzolar, acibenzolar-S-methyl, 5-aminolevulinic acid, ancymidol, 6-benzylaminopurine, brassinolide, catechol, chlormequat chloride, cloprop, cyclanilide, 3-(cycloprop-1-enyl)propionic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indole-3-acetic acid (IAA), 4-indol-3-ylbutyric acid, isoprothiolane, probenazole, jasmonic acid, jasmonic acid methyl ester, maleic hydrazide, mepiquat chloride, 1-methylcyclopropene, 2-(1-naphthyl)acetamide, 1-naphthylacetic acid, 2-naphthyloxyacetic acid, nitrophenolate mixture, 4-oxo-4[(2-phenylethyl)amino]butyric acid, paclobutrazole, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Useful combination partners for the compounds of the general formula (I) according to the invention also include, for example, the following safeners:

S1) Compounds from the group of heterocyclic carboxylic acid derivatives:

S1$^a$) Compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

S1$^b$) Derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333131 and EP-A-269806;

S1$^c$) Derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described, for example, in EP-A-268554;

S1$^d$) Compounds of the triazolecarboxylic acid type (S1$^d$), preferably compounds such as fenchlorazole(-ethyl ester), i.e. ethyl 1-(2,4-dichlorophenyl)-5-trichloromethyl-1H-1,2,4-triazole-3-carboxylate (S1-7), and related compounds, as described in EP-A-174562 and EP-A-346620;

S1$^e$) Compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazolinecarboxylic acid (S1-10) or ethyl 5,5-diphenyl-2-isoxazoline-3-carboxylate (51-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13) as described in patent application WO-A-95/07897.

S2) Compounds from the group of the 8-quinolinoxy derivatives (S2):

S2$^a$) Compounds of the 8-quinolinoxyacetic acid type (S2$^a$), preferably 1-methylhexyl (5-chloro-8-quinolinoxy)acetate ("cloquintocet-mexyl") (52-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86750, EP-A-94349 and EP-A-191736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

S2$^b$) Compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Active compounds of the dichloroacetamide type (S3), which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4.5]decane) from Nitrokemia or Monsanto (S3-7), "TI-35" (1-dichloroacetylazepane) from TRI-Chemical RT (S3-8), "diclonon" (dicyclonon) or "BAS145138" or "LAB145138" (S3-9)

((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10), and the (R) isomer thereof (S3-11).

S4) Compounds from the class of the acylsulfonamides (S4):

S4$^a$) N-Acylsulfonamides of the formula (S4$^a$) and salts thereof, as described in WO-A-97/45016,

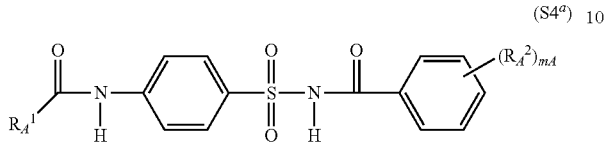
(S4$^a$)

in which
$R_A^1$ represents $(C_1-C_6)$-alkyl, $(C_3-C_6)$-cycloalkyl, where the 2 latter radicals are substituted by $v_A$ substituents from the group of halogen, $(C_1-C_4)$-alkoxy, $(C_1-C_6)$-haloalkoxy and $(C_1-C_4)$-alkylthio and, in the case of cyclic radicals, also by $(C_1-C_4)$-alkyl and $(C_1-C_4)$-haloalkyl;
$R_A^2$ represents halogen, $(C_1-C_4)$-alkyl, $(C_1-C_4)$-alkoxy, $CF_3$;
$m_A$ represents 1 or 2;
$v_A$ represents 0, 1, 2 or 3;

S4$^b$) Compounds of the 4-(benzoylsulfamoyl)benzamide type of the formula (S4$^b$) and salts thereof, as described in WO-A-99/16744,

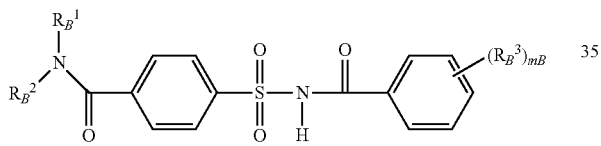
(S4$^b$)

in which
$R_B^1$, $R_B^2$ independently of one another represent hydrogen, $(C_1-C_6)$-alkyl, $(C_3-C_6)$-cycloalkyl, $(C_3-C_6)$-alkenyl, $(C_3-C_6)$-alkynyl,
$R_B^3$ represents halogen, $(C_1-C_4)$-alkyl, $(C_1-C_4)$-haloalkyl or $(C_1-C_4)$-alkoxy and
$m_B$ represents 1 or 2,
e.g. those in which
$R_B^1$=cyclopropyl, $R_B^2$=hydrogen and $(R_B^3)$=2-OMe ("cyprosulfamide", S4-1),
$R_B^1$=cyclopropyl, $R_B^2$=hydrogen and $(R_B^3)$=5-Cl-2-OMe (S4-2),
$R_B^1$=ethyl, $R_B^2$=hydrogen and $(R_B^3)$=2-OMe (S4-3),
$R_B^1$=isopropyl, $R_B^2$=hydrogen and $(R_B^3)$=5-Cl-2-OMe (S4-4) and
$R_B^1$=isopropyl, $R_B^2$=hydrogen and $(R_B^3)$=2-OMe (S4-5);

S4$^c$) Compounds from the class of the benzoylsulfamoylphenylureas of the formula (S4$^c$), as described in EP-A-365484,

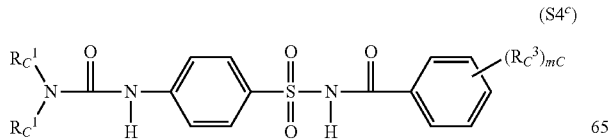
(S4$^c$)

in which
$R_C^1$, $R_C^2$ independently of one another represent hydrogen, $(C_1-C_8)$-alkyl, $(C_3-C_8)$-cycloalkyl, $(C_3-C_6)$-alkenyl, $(C_3-C_6)$-alkynyl,
$R_C^3$ represents halogen, $(C_1-C_4)$-alkyl, $(C_1-C_4)$-alkoxy, $CF_3$ and
$m_C$ represents 1 or 2;
for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea;

S4$^d$) Compounds of the N-phenylsulfonylterephthalamide type of the formula (S4$^d$) and salts thereof, which are known, for example, from CN 101838227,

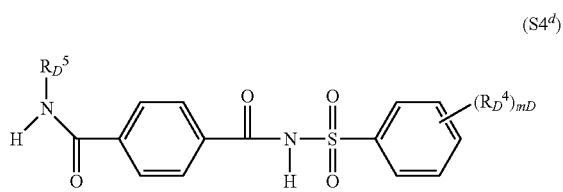
(S4$^d$)

in which
$R_D^4$ is halogen, $(C_1-C_4)$-alkyl, $(C_1-C_4)$-alkoxy, $CF_3$;
$m_D$ is 1 or 2;
$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl.

S5) Active compounds from the class of the hydroxyaromatics and the aromatic-aliphatic carboxylic acid derivatives (S5), for example
ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example
1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds from the class of the diphenylmethoxyacetic acid derivatives (S7), e.g. methyl diphenylmethoxyacetate (CAS Reg. No. 41858-19-9) (S7-1), ethyl diphenylmethoxyacetate or diphenylmethoxyacetic acid, as described in WO-A-98/38856.

S8) Compounds of the formula (S8), as described in WO-A-98/27049,

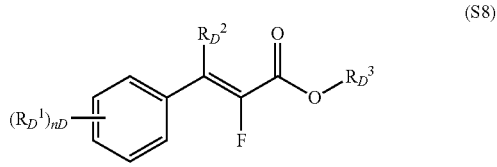
(S8)

in which the symbols and indices are defined as follows:
$R_D^1$ represents halogen, $(C_1-C_4)$-alkyl, $(C_1-C_4)$-haloalkyl, $(C_1-C_4)$-alkoxy, $(C_1-C_4)$-haloalkoxy,
$R_D^2$ represents hydrogen or $(C_1-C_4)$-alkyl,
$R_D^3$ represents hydrogen, $(C_1-C_8)$-alkyl, $(C_2-C_4)$-alkenyl, $(C_2-C_4)$-alkynyl or aryl, where each of the abovementioned carbon-containing radicals is unsubstituted or substituted by one or more, preferably up to three identical or different radicals from the group consisting of halogen and alkoxy; or salts thereof,
$n_D$ represents an integer from 0 to 2.

S9) Active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No. 95855-00-8), as described in WO-A-1999/000020.

S10) Compounds of the formulae (S10$^a$) or (S10$^b$) as described in WO-A-2007/023719 and WO-A-2007/023764

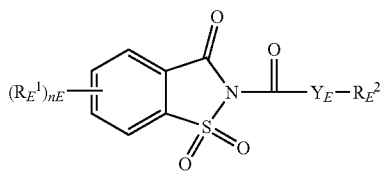

(S10$^a$)

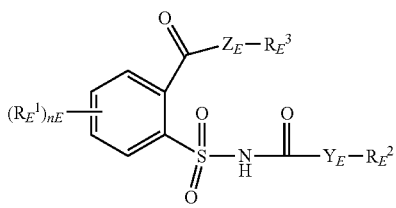

(S10$^b$)

in which
$R_E^1$ represents halogen, $(C_1-C_4)$-alkyl, methoxy, nitro, cyano, $CF_3$, $OCF_3$,
$Y_E$, $Z_E$ independently of one another represent O or S,
$n_E$ represents an integer from 0 to 4,
$R_E^2$ represents $(C_1-C_{16})$-alkyl, $(C_2-C_6)$-alkenyl, $(C_3-C_6)$-cycloalkyl, aryl, benzyl, halobenzyl,
$R_E^3$ represents hydrogen or $(C_1-C_6)$-alkyl.

S11) Active compounds of the oxyimino compounds type (S11), which are known as seed-dressing agents, for example
"oxabetrinil" ((Z)-1,3-dioxolan-2-ylmethoxyimino(phenyl)acetonitrile) (S11-1), which is known as a seed-dressing safener for millet/sorghum against metolachlor damage,
"fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against metolachlor damage, and
"cyometrinil" or "CGA-43089" ((Z)-cyanomethoxyimino(phenyl)acetonitrile) (S11-3), which is known as a seed-dressing safener for millet/sorghum against metolachlor damage.

S12) Active compounds from the class of the isothiochromanones (S12), for example methyl [(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):
"naphthalic anhydride" (1,8-naphthalenedicarboxylic anhydride) (S13-1), which is known as a seed-dressing safener for corn against thiocarbamate herbicide damage,
"fenclorim" (4,6-dichloro-2-phenylpyrimidine) (S13-2), which is known as a safener for pretilachlor in sown rice,
"flurazole" (benzyl 2-chloro-4-trifluoromethyl-1,3-thiazole-5-carboxylate) (S13-3), which is known as a seed-dressing safener for millet/sorghum against alachlor and metolachlor damage,
"CL 304415" (CAS Reg. No. 31541-57-8) (4-carboxy-3,4-dihydro-2H-1-benzopyran-4-acetic acid) (S13-4) from American Cyanamid, which is known as a safener for corn against damage by imidazolinones,
"MG 191" (CAS Reg. No. 96420-72-3) (2-dichloromethyl-2-methyl-1,3-dioxolane) (S13-5) from Nitrokemia, which is known as a safener for corn,
"MG 838" (CAS Reg. No. 133993-74-5) (2-propenyl 1-oxa-4-azaspiro[4.5]decane-4-carbodithioate) (S13-6) from Nitrokemia
"disulfoton" (O,O-diethyl S-2-ethylthioethyl phosphorodithioate) (S13-7),
"dietholate" (O,O-diethyl O-phenyl phosphorothioate) (S13-8),
"mephenate" (4-chlorophenyl methylcarbamate) (S13-9).

S14) Active compounds which, in addition to herbicidal action against harmful plants, also have safener action on crop plants such as rice, for example
"dimepiperate" or "MY-93" (S-1-methyl 1-phenylethylpiperidine-1-carbothioate), which is known as a safener for rice against damage by the herbicide molinate,
"daimuron" or "SK 23" (1-(1-methyl-1-phenylethyl)-3-p-tolylurea), which is known as a safener for rice against damage by the herbicide imazosulfuron,
"cumyluron"="JC-940" (3-(2-chlorophenylmethyl)-1-(1-methyl-1-phenylethyl)urea, see JP-A-60087270), which is known as a safener for rice against damage by some herbicides,
"methoxyphenone" or "NK 049" (3,3'-dimethyl-4-methoxybenzophenone), which is known as a safener for rice against damage by some herbicides,
"CSB" (1-bromo-4-(chloromethylsulfonyl)benzene) from Kumiai, (CAS Reg. No. 54091-06-4), which is known as a safener against damage by some herbicides in rice.

S15) Compounds of the formula (S15) or tautomers thereof

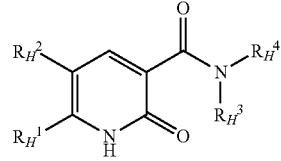

(S15)

as described in WO-A-2008/131861 and WO-A-2008/131860
in which
$R_H^1$ is a $(C_1-C_6)$-haloalkyl radical and
$R_H^2$ is hydrogen or halogen and $R_H^3$, $R_H^4$ independently of one another are hydrogen, $(C_1-C_{16})$-alkyl, $(C_2-C_{16})$-alkenyl or $(C_2-C_{16})$-alkynyl, where each of the 3 last-mentioned radicals is unsubstituted or substituted by one or more radicals from the group of halogen, hydroxy, cyano, $(C_1-C_4)$-alkoxy, $(C_1-C_4)$-haloalkoxy, $(C_1-C_4)$-alkylthio, $(C_1-C_4)$-alkylamino, di$[(C_1-C_4)$-alkyl]amino, $[(C_1-C_4)$-alkoxy]carbonyl, $[(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, $(C_3-C_6)$-cycloalkyl fused on one side of the ring to a 4- to 6-membered saturated or unsaturated carbocyclic ring, or $(C_4-C_6)$-cycloalkenyl fused on one side of the ring to a 4- to 6-membered saturated or unsaturated carbocyclic ring, where each of the 4 latter radicals is unsubstituted or substituted by one or more radicals from the group of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di$[(C_1-C_4)$-alkyl]amino, $[(C_1-C_4)$-alkoxy]carbonyl, $[(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $R_H^3$ is $(C_1-C_4)$-alkoxy, $(C_2-C_4)$-alkenyloxy-, $(C_2-C_6)$-alkynyloxy or $(C_2-C_4)$-haloalkoxy and $R_H^4$ is hydrogen or $(C_1-C_4)$-alkyl or $R_H^3$ and $R_H^4$ together with the directly attached nitrogen atom represent a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor-ethyl).

Preferred safeners in combination with the compounds of the general formula (I) according to the invention and/or salts thereof, in particular with the compounds of the formulae (I-1) to (I-229) and/or salts thereof, are: cloquintocet-mexyl, cyprosulfamide, fenchlorazole ethyl ester, isoxadifen-ethyl, mefenpyr-diethyl, fenclorim, cumyluron, S4-1 and S4-5, and particularly preferred safeners are: cloquintocet-mexyl, cyprosulfamide, isoxadifen-ethyl and mefenpyr-diethyl.

Biological Examples

In the examples and tables below, the following abbreviations are used:
Undesired Plants/Weeds:
ABUTH: *Abutilon theophrasti*
AGSTE: *Agrostis tenuis*
AMARE *Amaranthus retroflexus*
ECHCG: *Echinochloa crus-galli*
LOLRI: *Lolium rigidum*
MATIN: *Matricaria inodora*
POAAN: *Poa annua*
SETVI: *Setaria viridis*
STEME: *Stellaria media*

A. Herbicidal Early Post-Emergence Action

Seeds of monocotyledonous and dicotyledonous weed plants were placed in 96-well microtiter plates in quartz sand and grown in a climatized chamber under controlled growth conditions. 5 to 7 days after sowing, the test plants were treated at the cotyledon stage. The compounds according to the invention, formulated in the form of emulsion concentrates (EC), were applied with a water application rate of the equivalent of 2200 liters per hectare. After the test plants had been left to stand in the climatized chamber for 9 to 12 days under optimum growth conditions, the effect of the preparations was scored visually in comparison to untreated controls.

Here, for example, 100% activity=the plants have died, 0% activity=like untreated control plants.

Tables A1 to A2 below show the effects of selected compounds of the general formula (I) according to Table 1 above on various harmful plants and an application rate corresponding to 1900 g/ha, which were obtained by the experimental procedure mentioned above.

TABLE A1

| Example number | Dosage [g/ha] | AGSTE |
|---|---|---|
| 1-40 | 1900 | 80 |
| 1-75 | 1900 | 100 |
| 1-79 | 1900 | 80 |
| 1-88 | 1900 | 100 |
| 1-106 | 1900 | 100 |
| 1-111 | 1900 | 100 |
| 1-124 | 1900 | 100 |
| 1-129 | 1900 | 100 |
| 1-139 | 1900 | 100 |
| 1-143 | 1900 | 80 |
| 1-144 | 1900 | 100 |
| 1-146 | 1900 | 80 |
| 1-149 | 1900 | 100 |
| 1-204 | 1900 | 100 |
| 1-235 | 1900 | 100 |
| 1-239 | 1900 | 80 |
| 1-246 | 1900 | 80 |
| 1-247 | 1900 | 80 |
| 1-248 | 1900 | 100 |
| 1-250 | 1900 | 80 |
| 1-251 | 1900 | 80 |
| 1-253 | 1900 | 100 |
| 1-255 | 1900 | 80 |
| 1-256 | 1900 | 80 |
| 1-260 | 1900 | 100 |
| 1-261 | 1900 | 80 |
| 1-265 | 1900 | 80 |
| 1-266 | 1900 | 80 |
| 1-267 | 1900 | 100 |
| 1-268 | 1900 | 100 |
| 1-269 | 1900 | 80 |
| 1-270 | 1900 | 80 |
| 1-271 | 1900 | 80 |

TABLE A1-continued

| Example number | Dosage [g/ha] | AGSTE |
|---|---|---|
| 1-272 | 1900 | 100 |
| 1-273 | 1900 | 80 |
| 1-274 | 1900 | 80 |
| 1-275 | 1900 | 80 |
| 1-278 | 1900 | 100 |
| 1-279 | 1900 | 80 |
| 1-280 | 1900 | 100 |
| 1-281 | 1900 | 100 |
| 1-284 | 1900 | 100 |
| 1-286 | 1900 | 100 |
| 1-287 | 1900 | 80 |
| 1-288 | 1900 | 80 |
| 1-289 | 1900 | 80 |
| 1-290 | 1900 | 80 |
| 1-291 | 1900 | 100 |
| 1-292 | 1900 | 100 |
| 1-293 | 1900 | 80 |
| 1-294 | 1900 | 80 |
| 1-297 | 1900 | 100 |
| 1-298 | 1900 | 80 |
| 1-299 | 1900 | 80 |
| 1-300 | 1900 | 80 |
| 1-304 | 1900 | 100 |
| 1-305 | 1900 | 100 |
| 1-306 | 1900 | 100 |
| 1-308 | 1900 | 100 |
| 1-310 | 1900 | 80 |
| 1-312 | 1900 | 100 |
| 1-314 | 1900 | 100 |
| 1-324 | 1900 | 100 |
| 1-328 | 1900 | 80 |
| 1-336 | 1900 | 100 |
| 1-337 | 1900 | 100 |
| 1-339 | 1900 | 100 |
| 1-340 | 1900 | 80 |
| 1-341 | 1900 | 100 |
| 1-350 | 1900 | 80 |
| 1-358 | 1900 | 100 |
| 1-365 | 1900 | 100 |
| 1-366 | 1900 | 100 |
| 1-369 | 1900 | 80 |
| 1-372 | 1900 | 100 |
| 1-374 | 1900 | 100 |
| 1-375 | 1900 | 100 |
| 1-376 | 1900 | 80 |
| 2-101 | 1900 | 100 |
| 2-136 | 1900 | 80 |
| 2-139 | 1900 | 80 |
| 3-49 | 1900 | 80 |
| 3-53 | 1900 | 100 |
| 3-54 | 1900 | 100 |
| 3-55 | 1900 | 100 |
| 3-56 | 1900 | 100 |

TABLE A2

| Example number | Dosage [g/ha] | POAAN |
|---|---|---|
| 1-40 | 1900 | 80 |
| 1-75 | 1900 | 80 |
| 1-79 | 1900 | 100 |
| 1-88 | 1900 | 80 |
| 1-106 | 1900 | 100 |
| 1-111 | 1900 | 100 |
| 1-124 | 1900 | 100 |
| 1-139 | 1900 | 80 |
| 1-144 | 1900 | 100 |
| 1-145 | 1900 | 80 |
| 1-204 | 1900 | 100 |
| 1-235 | 1900 | 100 |
| 1-239 | 1900 | 100 |
| 1-248 | 1900 | 100 |
| 1-250 | 1900 | 80 |
| 1-251 | 1900 | 80 |
| 1-253 | 1900 | 100 |
| 1-255 | 1900 | 80 |
| 1-256 | 1900 | 80 |
| 1-260 | 1900 | 100 |
| 1-261 | 1900 | 80 |
| 1-266 | 1900 | 100 |
| 1-267 | 1900 | 100 |
| 1-268 | 1900 | 80 |
| 1-269 | 1900 | 100 |
| 1-270 | 1900 | 80 |
| 1-271 | 1900 | 80 |
| 1-272 | 1900 | 100 |
| 1-274 | 1900 | 100 |
| 1-275 | 1900 | 100 |
| 1-278 | 1900 | 100 |
| 1-279 | 1900 | 100 |
| 1-280 | 1900 | 100 |
| 1-284 | 1900 | 100 |
| 1-286 | 1900 | 100 |
| 1-288 | 1900 | 80 |
| 1-289 | 1900 | 80 |
| 1-291 | 1900 | 100 |
| 1-292 | 1900 | 80 |
| 1-293 | 1900 | 80 |
| 1-294 | 1900 | 100 |
| 1-297 | 1900 | 80 |
| 1-298 | 1900 | 80 |
| 1-299 | 1900 | 100 |
| 1-304 | 1900 | 100 |
| 1-305 | 1900 | 100 |
| 1-306 | 1900 | 80 |
| 1-308 | 1900 | 100 |
| 1-312 | 1900 | 100 |
| 1-314 | 1900 | 80 |
| 1-324 | 1900 | 80 |
| 1-328 | 1900 | 80 |
| 1-336 | 1900 | 100 |
| 1-337 | 1900 | 100 |
| 1-339 | 1900 | 100 |
| 1-340 | 1900 | 100 |
| 1-341 | 1900 | 100 |
| 1-350 | 1900 | 100 |
| 1-358 | 1900 | 100 |
| 1-366 | 1900 | 80 |
| 1-369 | 1900 | 80 |
| 1-372 | 1900 | 100 |
| 1-374 | 1900 | 100 |
| 1-375 | 1900 | 100 |
| 1-376 | 1900 | 80 |
| 2-101 | 1900 | 80 |
| 3-53 | 1900 | 100 |
| 3-54 | 1900 | 100 |
| 3-55 | 1900 | 100 |
| 3-56 | 1900 | 100 |

The test results show that compounds of the general formula (I) according to the invention, in the case of early post-emergence treatment, have good herbicidal activity against selected harmful plants such as *Agrostis tenuis* and *Poa annua*, at a respective application rate of 1900 g of active substance per hectare.

B. Herbicidal Post-Emergence Action

Seeds of mono- and dicotyledonous weed plants were placed in plastic pots in sandy loam soil (doubly sown with in each case one species of mono- or dicotyledonous weed plants per pot), covered with soil and cultivated in a greenhouse under controlled growth conditions. 2 to 3 weeks after sowing, the test plants were treated at the one-leaf stage. The compounds of the invention, formulated in the form of wettable powders (WP) or as emulsion concentrates (EC), were applied onto the green parts of the plants as aqueous suspension or emulsion with addition of 0.5% additive at a water application rate of 600 liters per hectare (converted). After the test plants had been kept in the greenhouse under optimum growth conditions for about 3 weeks, the activity of the preparations was rated visually in comparison to untreated controls.

For example, 100% activity=the plants have died, 0% activity=like untreated control plants.

Tables B1-B8 below show the effects of selected compounds of the general formula (I) according to Table 1 above on various harmful plants and an application rate corresponding to 1280 g/ha, which were obtained by the experimental procedure mentioned above.

TABLE B1

| Example number | Dosage [g/ha] | ECHCG |
|---|---|---|
| 1-204 | 1280 | 100 |
| 1-235 | 1280 | 100 |
| 1-248 | 1280 | 100 |
| 1-253 | 1280 | 100 |
| 1-266 | 1280 | 100 |
| 1-267 | 1280 | 100 |
| 1-269 | 1280 | 90 |
| 1-270 | 1280 | 90 |
| 1-272 | 1280 | 100 |
| 1-275 | 1280 | 90 |
| 1-278 | 1280 | 90 |
| 1-286 | 1280 | 100 |
| 1-288 | 1280 | 100 |
| 1-289 | 1280 | 100 |
| 1-291 | 1280 | 100 |
| 1-308 | 1280 | 100 |
| 1-337 | 1280 | 90 |
| 1-374 | 1280 | 100 |
| 3-53 | 1280 | 100 |
| 3-53 | 1280 | 100 |
| 3-56 | 1280 | 100 |

TABLE B2

| Example number | Dosage [g/ha] | LOLRI |
|---|---|---|
| 1-204 | 1280 | 90 |
| 1-267 | 1280 | 90 |
| 1-272 | 1280 | 100 |
| 1-286 | 1280 | 90 |
| 3-53 | 1280 | 90 |
| 3-55 | 1280 | 90 |

TABLE B3

| Example number | Dosage [g/ha] | POAAN |
|---|---|---|
| 1-139 | 1280 | 100 |
| 1-204 | 1280 | 100 |
| 1-235 | 1280 | 100 |
| 1-239 | 1280 | 100 |
| 1-248 | 1280 | 100 |
| 1-267 | 1280 | 100 |
| 1-269 | 1280 | 90 |
| 1-272 | 1280 | 100 |
| 1-279 | 1280 | 100 |
| 1-286 | 1280 | 100 |
| 1-288 | 1280 | 100 |
| 1-291 | 1280 | 100 |
| 1-294 | 1280 | 100 |
| 1-298 | 1280 | 90 |
| 1-308 | 1280 | 100 |
| 1-350 | 1280 | 100 |
| 1-369 | 1280 | 100 |
| 1-372 | 1280 | 100 |
| 1-374 | 1280 | 100 |
| 1-375 | 1280 | 100 |
| 3-53 | 1280 | 100 |
| 3-54 | 1280 | 100 |
| 3-55 | 1280 | 100 |
| 3-56 | 1280 | 100 |

TABLE B4

| Example number | Dosage [g/ha] | SETVI |
|---|---|---|
| 1-204 | 1280 | 100 |
| 1-253 | 1280 | 90 |
| 1-269 | 1280 | 90 |
| 1-270 | 1280 | 90 |
| 1-272 | 1280 | 100 |
| 1-275 | 1280 | 90 |
| 1-286 | 1280 | 100 |
| 1-288 | 1280 | 90 |
| 1-289 | 1280 | 90 |
| 1-291 | 1280 | 100 |
| 1-298 | 1280 | 90 |
| 1-299 | 1280 | 90 |
| 1-308 | 1280 | 100 |
| 3-53 | 1280 | 90 |
| 3-54 | 1280 | 90 |
| 3-55 | 1280 | 90 |
| 3-56 | 1280 | 100 |

TABLE B5

| Example number | Dosage [g/ha] | ABUTH |
|---|---|---|
| 1-111 | 1280 | 90 |
| 1-204 | 1280 | 100 |
| 1-235 | 1280 | 100 |
| 1-248 | 1280 | 100 |
| 1-253 | 1280 | 100 |
| 1-266 | 1280 | 100 |
| 1-267 | 1280 | 100 |
| 1-269 | 1280 | 90 |
| 1-270 | 1280 | 90 |
| 1-272 | 1280 | 100 |
| 1-275 | 1280 | 90 |
| 1-278 | 1280 | 90 |
| 1-286 | 1280 | 100 |
| 1-288 | 1280 | 90 |
| 1-289 | 1280 | 90 |
| 1-291 | 1280 | 100 |
| 1-293 | 1280 | 90 |
| 1-298 | 1280 | 90 |
| 1-308 | 1280 | 100 |
| 1-312 | 1280 | 100 |
| 1-314 | 1280 | 90 |
| 1-337 | 1280 | 90 |
| 1-340 | 1280 | 90 |
| 1-374 | 1280 | 100 |
| 1-375 | 1280 | 90 |
| 3-49 | 1280 | 90 |
| 3-53 | 1280 | 100 |
| 3-54 | 1280 | 100 |
| 3-55 | 1280 | 100 |
| 3-56 | 1280 | 100 |

TABLE B6

| Example number | Dosage [g/ha] | AMARE |
|---|---|---|
| 1-106 | 1280 | 100 |
| 1-111 | 1280 | 100 |
| 1-124 | 1280 | 100 |
| 1-129 | 1280 | 100 |
| 1-149 | 1280 | 100 |
| 1-235 | 1280 | 100 |
| 1-239 | 1280 | 100 |
| 1-246 | 1280 | 100 |
| 1-247 | 1280 | 100 |
| 1-248 | 1280 | 100 |
| 1-250 | 1280 | 100 |
| 1-251 | 1280 | 100 |
| 1-253 | 1280 | 100 |
| 1-254 | 1280 | 100 |
| 1-255 | 1280 | 100 |
| 1-256 | 1280 | 100 |
| 1-260 | 1280 | 100 |
| 1-261 | 1280 | 100 |
| 1-265 | 1280 | 100 |
| 1-266 | 1280 | 100 |
| 1-267 | 1280 | 100 |
| 1-268 | 1280 | 90 |
| 1-269 | 1280 | 100 |
| 1-270 | 1280 | 100 |
| 1-271 | 1280 | 100 |
| 1-272 | 1280 | 100 |
| 1-273 | 1280 | 100 |
| 1-274 | 1280 | 100 |
| 1-275 | 1280 | 100 |
| 1-278 | 1280 | 100 |
| 1-279 | 1280 | 100 |
| 1-280 | 1280 | 100 |
| 1-284 | 1280 | 100 |
| 1-285 | 1280 | 100 |
| 1-286 | 1280 | 100 |
| 1-287 | 1280 | 100 |
| 1-288 | 1280 | 100 |
| 1-289 | 1280 | 100 |
| 1-290 | 1280 | 100 |
| 1-291 | 1280 | 100 |
| 1-292 | 1280 | 100 |
| 1-293 | 1280 | 100 |
| 1-294 | 1280 | 100 |
| 1-297 | 1280 | 100 |
| 1-298 | 1280 | 100 |
| 1-299 | 1280 | 100 |
| 1-300 | 1280 | 100 |
| 1-304 | 1280 | 100 |
| 1-305 | 1280 | 100 |
| 1-308 | 1280 | 100 |
| 1-312 | 1280 | 100 |
| 1-314 | 1280 | 100 |
| 1-337 | 1280 | 90 |
| 1-339 | 1280 | 100 |
| 1-340 | 1280 | 100 |
| 1-341 | 1280 | 100 |
| 1-342 | 1280 | 100 |
| 1-350 | 1280 | 100 |
| 1-369 | 1280 | 100 |
| 1-374 | 1280 | 100 |
| 1-375 | 1280 | 100 |
| 3-49 | 1280 | 100 |
| 3-53 | 1280 | 100 |
| 3-54 | 1280 | 100 |
| 3-55 | 1280 | 100 |
| 3-56 | 1280 | 100 |

TABLE B7

| Example number | Dosage [g/ha] | MATIN |
|---|---|---|
| 1-139 | 1280 | 100 |
| 1-235 | 1280 | 80 |
| 1-272 | 1280 | 100 |
| 1-306 | 1280 | 100 |
| 1-310 | 1280 | 100 |
| 1-336 | 1280 | 100 |
| 1-374 | 1280 | 100 |
| 3-53 | 1280 | 90 |
| 3-55 | 1280 | 90 |

TABLE B8

| Example number | Dosage [g/ha] | STEME |
|---|---|---|
| 1-88 | 1280 | 100 |
| 1-106 | 1280 | 90 |
| 1-111 | 1280 | 90 |
| 1-204 | 1280 | 100 |
| 1-235 | 1280 | 100 |
| 1-239 | 1280 | 100 |
| 1-248 | 1280 | 100 |
| 1-250 | 1280 | 90 |
| 1-253 | 1280 | 100 |
| 1-255 | 1280 | 100 |
| 1-260 | 1280 | 90 |
| 1-266 | 1280 | 100 |
| 1-267 | 1280 | 100 |
| 1-269 | 1280 | 100 |
| 1-270 | 1280 | 100 |
| 1-272 | 1280 | 100 |
| 1-274 | 1280 | 90 |
| 1-275 | 1280 | 100 |
| 1-278 | 1280 | 100 |
| 1-279 | 1280 | 100 |
| 1-280 | 1280 | 100 |
| 1-286 | 1280 | 100 |
| 1-289 | 1280 | 100 |
| 1-291 | 1280 | 100 |
| 1-294 | 1280 | 100 |
| 1-298 | 1280 | 100 |
| 1-299 | 1280 | 100 |
| 1-305 | 1280 | 100 |
| 1-306 | 1280 | 100 |
| 1-308 | 1280 | 100 |
| 1-310 | 1280 | 90 |
| 1-312 | 1280 | 100 |
| 1-314 | 1280 | 100 |
| 1-336 | 1280 | 100 |
| 1-339 | 1280 | 100 |
| 1-340 | 1280 | 100 |
| 1-372 | 1280 | 90 |
| 1-374 | 1280 | 100 |
| 1-375 | 1280 | 100 |
| 3-53 | 1280 | 100 |
| 3-54 | 1280 | 90 |
| 3-55 | 1280 | 100 |
| 3-56 | 1280 | 100 |

The test results show that compounds of the general formula (I) according to the invention, in the case of post-emergence treatment, have good herbicidal activity against selected harmful plants such as *Echinochloa crusgalli, Poa annua, Abutilon theophrasti, Amaranthus retroflexus, Lolium rigidum, Setaria viridis, Stellaria media* and *Matricaria inodora* at a respective application rate of 1280 g of active substance per hectare.

C. Herbicidal Pre-Emergence Action

Seeds of mono- and dicotyledonous weed plants were placed in plastic pots in sandy loam soil (doubly sown with one species each of mono- or dicotyledonous weed plants per pot) and covered with soil. The compounds of the invention, formulated in the form of wettable powders (WP)

or as emulsion concentrates (EC), were then applied onto the surface of the covering soil as aqueous suspension or emulsion with addition of 0.5% additive at a water application rate of 600 liters per hectare (converted). After the treatment, the pots were placed in a greenhouse and kept under good growth conditions for the test plants. After about 3 weeks, the effect of the preparations was scored visually in comparison with untreated controls as percentages.

For example, 100% activity=the plants have died, 0% activity=like untreated control plants.

Tables C1-C8 below show the effects of selected compounds of the general formula (I) according to Table 1 above on various harmful plants and an application rate corresponding to 1280 g/ha, which were obtained by the experimental procedure mentioned above.

TABLE C1

| Example number | Dosage [g/ha] | ECHCG |
|---|---|---|
| 1-204 | 1280 | 100 |
| 1-235 | 1280 | 90 |
| 1-247 | 1280 | 90 |
| 1-248 | 1280 | 100 |
| 1-253 | 1280 | 100 |
| 1-260 | 1280 | 90 |
| 1-261 | 1280 | 100 |
| 1-266 | 1280 | 90 |
| 1-267 | 1280 | 100 |
| 1-269 | 1280 | 90 |
| 1-270 | 1280 | 100 |
| 1-272 | 1280 | 100 |
| 1-275 | 1280 | 90 |
| 1-280 | 1280 | 100 |
| 1-285 | 1280 | 90 |
| 1-288 | 1280 | 90 |
| 1-291 | 1280 | 90 |
| 1-294 | 1280 | 90 |
| 1-308 | 1280 | 90 |
| 1-374 | 1280 | 100 |
| 1-375 | 1280 | 100 |
| 3-53 | 1280 | 100 |
| 3-54 | 1280 | 100 |
| 3-55 | 1280 | 100 |
| 3-56 | 1280 | 100 |

TABLE C2

| Example number | Dosage [g/ha] | LOLRI |
|---|---|---|
| 1-248 | 1280 | 100 |
| 1-253 | 1280 | 100 |
| 1-267 | 1280 | 100 |
| 1-269 | 1280 | 90 |
| 1-272 | 1280 | 100 |
| 1-278 | 1280 | 100 |
| 1-279 | 1280 | 90 |
| 1-286 | 1280 | 90 |
| 1-291 | 1280 | 100 |
| 1-299 | 1280 | 90 |
| 1-375 | 1280 | 90 |
| 3-53 | 1280 | 100 |
| 3-54 | 1280 | 100 |
| 3-55 | 1280 | 100 |

TABLE C3

| Example number | Dosage [g/ha] | POAAN |
|---|---|---|
| 1-79 | 1280 | 100 |
| 1-106 | 1280 | 100 |
| 1-204 | 1280 | 100 |
| 1-235 | 1280 | 100 |
| 1-239 | 1280 | 100 |
| 1-247 | 1280 | 100 |
| 1-248 | 1280 | 100 |
| 1-250 | 1280 | 100 |
| 1-253 | 1280 | 100 |
| 1-254 | 1280 | 90 |
| 1-256 | 1280 | 100 |
| 1-260 | 1280 | 90 |
| 1-261 | 1280 | 100 |
| 1-265 | 1280 | 100 |
| 1-266 | 1280 | 100 |
| 1-267 | 1280 | 100 |
| 1-269 | 1280 | 100 |
| 1-270 | 1280 | 100 |
| 1-271 | 1280 | 90 |
| 1-272 | 1280 | 100 |
| 1-274 | 1280 | 90 |
| 1-275 | 1280 | 100 |
| 1-278 | 1280 | 100 |
| 1-279 | 1280 | 100 |
| 1-280 | 1280 | 100 |
| 1-285 | 1280 | 100 |
| 1-286 | 1280 | 100 |
| 1-287 | 1280 | 100 |
| 1-288 | 1280 | 100 |
| 1-289 | 1280 | 100 |
| 1-290 | 1280 | 90 |
| 1-291 | 1280 | 100 |
| 1-294 | 1280 | 100 |
| 1-298 | 1280 | 100 |
| 1-299 | 1280 | 100 |
| 1-304 | 1280 | 100 |
| 1-305 | 1280 | 100 |
| 1-308 | 1280 | 100 |
| 1-312 | 1280 | 100 |
| 1-337 | 1280 | 100 |
| 1-340 | 1280 | 100 |
| 1-350 | 1280 | 100 |
| 1-374 | 1280 | 100 |
| 1-375 | 1280 | 100 |
| 3-53 | 1280 | 100 |
| 3-54 | 1280 | 100 |
| 3-55 | 1280 | 100 |
| 3-56 | 1280 | 100 |

TABLE C4

| Example number | Dosage [g/ha] | SETVI |
|---|---|---|
| 1-88 | 1280 | 90 |
| 1-111 | 1280 | 90 |
| 1-129 | 1280 | 90 |
| 1-204 | 1280 | 100 |
| 1-235 | 1280 | 100 |
| 1-246 | 1280 | 100 |
| 1-247 | 1280 | 100 |
| 1-248 | 1280 | 100 |
| 1-250 | 1280 | 90 |
| 1-251 | 1280 | 90 |
| 1-253 | 1280 | 100 |
| 1-254 | 1280 | 100 |
| 1-256 | 1280 | 90 |
| 1-260 | 1280 | 100 |
| 1-261 | 1280 | 100 |
| 1-265 | 1280 | 90 |
| 1-266 | 1280 | 100 |
| 1-267 | 1280 | 100 |
| 1-269 | 1280 | 100 |
| 1-270 | 1280 | 100 |

TABLE C4-continued

| Example number | Dosage [g/ha] | SETVI |
|---|---|---|
| 1-271 | 1280 | 90 |
| 1-272 | 1280 | 100 |
| 1-273 | 1280 | 90 |
| 1-275 | 1280 | 100 |
| 1-278 | 1280 | 100 |
| 1-279 | 1280 | 100 |
| 1-280 | 1280 | 100 |
| 1-284 | 1280 | 100 |
| 1-285 | 1280 | 100 |
| 1-286 | 1280 | 100 |
| 1-287 | 1280 | 100 |
| 1-288 | 1280 | 100 |
| 1-289 | 1280 | 100 |
| 1-291 | 1280 | 100 |
| 1-292 | 1280 | 90 |
| 1-293 | 1280 | 100 |
| 1-294 | 1280 | 100 |
| 1-297 | 1280 | 100 |
| 1-298 | 1280 | 100 |
| 1-299 | 1280 | 100 |
| 1-304 | 1280 | 100 |
| 1-305 | 1280 | 90 |
| 1-306 | 1280 | 100 |
| 1-308 | 1280 | 100 |
| 1-312 | 1280 | 90 |
| 1-314 | 1280 | 100 |
| 1-340 | 1280 | 100 |
| 1-342 | 1280 | 100 |
| 1-369 | 1280 | 100 |
| 1-372 | 1280 | 100 |
| 1-374 | 1280 | 100 |
| 1-375 | 1280 | 100 |
| 3-53 | 1280 | 100 |
| 3-54 | 1280 | 100 |
| 3-55 | 1280 | 100 |
| 3-56 | 1280 | 100 |

TABLE C5

| Example number | Dosage [g/ha] | ABUTH |
|---|---|---|
| 1-248 | 1280 | 100 |
| 1-261 | 1280 | 100 |
| 1-267 | 1280 | 100 |
| 1-268 | 1280 | 90 |
| 1-269 | 1280 | 90 |
| 1-272 | 1280 | 100 |
| 1-280 | 1280 | 100 |
| 1-286 | 1280 | 90 |
| 1-294 | 1280 | 90 |
| 1-308 | 1280 | 100 |
| 1-375 | 1280 | 100 |
| 3-53 | 1280 | 100 |
| 3-54 | 1280 | 100 |
| 3-55 | 1280 | 100 |
| 3-56 | 1280 | 100 |

TABLE C6

| Example number | Dosage [g/ha] | AMARE |
|---|---|---|
| 1-88 | 1280 | 100 |
| 1-106 | 1280 | 100 |
| 1-111 | 1280 | 100 |
| 1-145 | 1280 | 90 |
| 1-149 | 1280 | 100 |
| 1-204 | 1280 | 100 |
| 1-235 | 1280 | 100 |
| 1-246 | 1280 | 100 |
| 1-247 | 1280 | 100 |

TABLE C6-continued

| Example number | Dosage [g/ha] | AMARE |
|---|---|---|
| 1-248 | 1280 | 100 |
| 1-250 | 1280 | 100 |
| 1-251 | 1280 | 100 |
| 1-252 | 1280 | 90 |
| 1-253 | 1280 | 100 |
| 1-254 | 1280 | 100 |
| 1-255 | 1280 | 100 |
| 1-256 | 1280 | 100 |
| 1-260 | 1280 | 100 |
| 1-261 | 1280 | 100 |
| 1-265 | 1280 | 100 |
| 1-266 | 1280 | 100 |
| 1-267 | 1280 | 100 |
| 1-268 | 1280 | 90 |
| 1-269 | 1280 | 100 |
| 1-270 | 1280 | 100 |
| 1-271 | 1280 | 100 |
| 1-272 | 1280 | 100 |
| 1-273 | 1280 | 100 |
| 1-274 | 1280 | 90 |
| 1-275 | 1280 | 100 |
| 1-278 | 1280 | 100 |
| 1-279 | 1280 | 100 |
| 1-280 | 1280 | 100 |
| 1-284 | 1280 | 100 |
| 1-285 | 1280 | 100 |
| 1-286 | 1280 | 100 |
| 1-287 | 1280 | 100 |
| 1-288 | 1280 | 100 |
| 1-289 | 1280 | 100 |
| 1-290 | 1280 | 90 |
| 1-291 | 1280 | 100 |
| 1-292 | 1280 | 100 |
| 1-293 | 1280 | 100 |
| 1-294 | 1280 | 100 |
| 1-298 | 1280 | 100 |
| 1-299 | 1280 | 100 |
| 1-300 | 1280 | 90 |
| 1-304 | 1280 | 100 |
| 1-305 | 1280 | 100 |
| 1-306 | 1280 | 100 |
| 1-308 | 1280 | 100 |
| 1-312 | 1280 | 100 |
| 1-337 | 1280 | 90 |
| 1-340 | 1280 | 100 |
| 1-342 | 1280 | 100 |
| 1-350 | 1280 | 100 |
| 1-369 | 1280 | 100 |
| 1-372 | 1280 | 100 |
| 1-374 | 1280 | 100 |
| 1-375 | 1280 | 100 |
| 3-53 | 1280 | 100 |
| 3-54 | 1280 | 100 |
| 3-55 | 1280 | 100 |
| 3-56 | 1280 | 100 |

TABLE C7

| Example number | Dosage [g/ha] | MATIN |
|---|---|---|
| 1-111 | 1280 | 90 |
| 1-204 | 1280 | 90 |
| 1-235 | 1280 | 100 |
| 1-239 | 1280 | 100 |
| 1-248 | 1280 | 100 |
| 1-251 | 1280 | 100 |
| 1-253 | 1280 | 100 |
| 1-256 | 1280 | 90 |
| 1-260 | 1280 | 90 |
| 1-261 | 1280 | 100 |
| 1-266 | 1280 | 100 |
| 1-267 | 1280 | 100 |
| 1-269 | 1280 | 100 |

TABLE C7-continued

| Example number | Dosage [g/ha] | MATIN |
|---|---|---|
| 1-270 | 1280 | 100 |
| 1-272 | 1280 | 100 |
| 1-275 | 1280 | 90 |
| 1-278 | 1280 | 100 |
| 1-279 | 1280 | 90 |
| 1-280 | 1280 | 100 |
| 1-286 | 1280 | 100 |
| 1-289 | 1280 | 100 |
| 1-291 | 1280 | 100 |
| 1-298 | 1280 | 90 |
| 1-300 | 1280 | 90 |
| 1-304 | 1280 | 100 |
| 1-305 | 1280 | 100 |
| 1-306 | 1280 | 90 |
| 1-308 | 1280 | 100 |
| 1-312 | 1280 | 100 |
| 1-350 | 1280 | 100 |
| 1-374 | 1280 | 100 |
| 1-375 | 1280 | 100 |
| 3-53 | 1280 | 100 |
| 3-54 | 1280 | 100 |
| 3-55 | 1280 | 100 |
| 3-56 | 1280 | 100 |

TABLE C8

| Example number | Dosage [g/ha] | STEME |
|---|---|---|
| 1-111 | 1280 | 100 |
| 1-129 | 1280 | 90 |
| 1-235 | 1280 | 100 |
| 1-246 | 1280 | 100 |
| 1-247 | 1280 | 100 |
| 1-248 | 1280 | 100 |
| 1-250 | 1280 | 100 |
| 1-251 | 1280 | 100 |
| 1-253 | 1280 | 100 |
| 1-255 | 1280 | 100 |
| 1-256 | 1280 | 100 |
| 1-260 | 1280 | 100 |
| 1-261 | 1280 | 100 |
| 1-265 | 1280 | 100 |
| 1-266 | 1280 | 100 |
| 1-267 | 1280 | 100 |
| 1-269 | 1280 | 100 |
| 1-270 | 1280 | 100 |
| 1-272 | 1280 | 100 |
| 1-274 | 1280 | 90 |
| 1-275 | 1280 | 100 |
| 1-278 | 1280 | 100 |
| 1-279 | 1280 | 100 |
| 1-280 | 1280 | 100 |
| 1-284 | 1280 | 90 |
| 1-285 | 1280 | 100 |
| 1-286 | 1280 | 100 |
| 1-288 | 1280 | 100 |
| 1-289 | 1280 | 100 |
| 1-291 | 1280 | 100 |
| 1-293 | 1280 | 90 |
| 1-294 | 1280 | 100 |
| 1-298 | 1280 | 100 |
| 1-299 | 1280 | 100 |
| 1-300 | 1280 | 100 |
| 1-304 | 1280 | 100 |
| 1-305 | 1280 | 100 |
| 1-306 | 1280 | 100 |
| 1-308 | 1280 | 100 |
| 1-312 | 1280 | 100 |
| 1-336 | 1280 | 100 |
| 1-340 | 1280 | 90 |
| 1-341 | 1280 | 90 |
| 1-369 | 1280 | 100 |
| 1-374 | 1280 | 100 |
| 1-375 | 1280 | 100 |
| 3-53 | 1280 | 100 |
| 3-54 | 1280 | 100 |
| 3-55 | 1280 | 100 |
| 3-56 | 1280 | 100 |

The test results show that compounds of the general formula (I) according to the invention, in the case of pre-emergence treatment, have good herbicidal activity against selected harmful plants such as *Echinochloa crusgalli, Lolium rigidum, Setaria viridis, Poa annua, Abutilon theophrasti, Amaranthus retroflexus, Stellaria media* and *Matricaria inodora* at an application rate of 1280 g of active substance per hectare.

The invention claimed is:
1. A compound of formula (I) or a salt thereof,

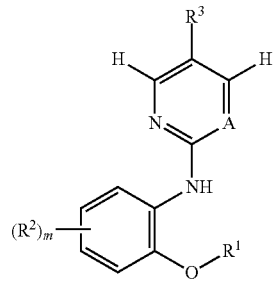

wherein:
A is nitrogen or —CX—,
X is hydrogen or halogen,
$R^1$ is an optionally substituted aryl or heteroaryl, where each ring or each ring system is optionally substituted by up to 5 substituents independently selected from the group $R^5$,
each $R^2$ is independently halogen, cyano, nitro, formyl, formamide, $(C_1-C_8)$-alkyl, $(C_1-C_8)$-haloalkyl, $(C_2-C_8)$-alkenyl, $(C_2-C_8)$-alkynyl, $(C_2-C_8)$-haloalkenyl, $(C_2-C_8)$-haloalkynyl, $(C_3-C_8)$-cycloalkyl, $(C_3-C_6)$-halocycloalkyl, $(C_3-C_6)$-cycloalkyl-$(C_1-C_6)$-alkyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, $(C_1-C_8)$-alkylcarbonyl, $(C_1-C_8)$-haloalkylcarbonyl, $(C_3-C_8)$-cycloalkylcarbonyl, carboxyl, $(C_1-C_8)$-alkoxycarbonyl, $(C_1-C_8)$-haloalkoxycarbonyl, $(C_3-C_8)$-cycloalkoxycarbonyl, carbamoyl, $(C_2-C_8)$-alkylaminocarbonyl, $(C_2-C_{10})$-dialkylaminocarbonyl, $(C_3-C_{10})$-cycloalkylaminocarbonyl, $(C_1-C_4)$-alkoxycarbonyl-$(C_1-C_4)$-alkyl, $(C_1-C_4)$-haloalkoxycarbonyl-$(C_1-C_4)$-alkyl, carboxy-$(C_1-C_4)$-alkyl, hydroxy, $NR^4R^6$, $(C_1-C_8)$-alkoxy, $(C_1-C_8)$-haloalkoxy, $(C_1-C_8)$-alkylthio, $(C_1-C_8)$-haloalkylthio, $(C_3-C_8)$-cycloalkylthio, $(C_1-C_4)$-alkoxy-$(C_1-C_4)$-alkylthio, $(C_1-C_8)$-alkylsulfinyl, $(C_1-C_8)$-haloalkylsulfinyl, $(C_3-C_8)$-cycloalkylsulfinyl, $(C_1-C_4)$-alkoxy-$(C_1-C_4)$-alkylsulfinyl, $(C_1-C_8)$-alkylsulfonyl, $(C_1-C_8)$-haloalkylsulfonyl, $(C_3-C_8)$-cycloalkylsulfonyl, $(C_1-C_4)$- alkoxy-$(C_1-C_4)$-alkylsulfonyl, $(C_1-C_8)$-alkylaminosulfonyl, $(C_2-C_8)$-dialkylaminosulfonyl or $(C_3-C_8)$-trialkylsilyl, m is 0, 1, 2 or 3, $R^3$ is hydrogen, halogen, cyano, nitro, $(C_1-C_8)$-alkyl, $(C_1-C_8)$-haloalkyl, $(C_2-C_4)$-alkenyl, $(C_2-C_4)$-alkynyl, $(C_3-C_6)$-cycloalkyl, $(C_3-C_6)$-cycloalkyl-$(C_1-C_6)$-alkyl, $(C_1-C_8)$-alkoxy, $(C_1-C_8)$-haloalkoxy, $(C_1-C_8)$-alkylthio, $(C_1-C_8)$-haloalkylthio, $(C_1-C_8)$-alkylsulfinyl, $(C_1-C_8)$-haloalkylsulfinyl, $(C_1-C_8)$-alkylsulfonyl, $(C_1-C_8)$-haloalkylsulfonyl, $R^4$ and $R^6$ are independently hydrogen, $(C_1-C_8)$-alkyl, $(C_1-C_8)$-haloalkyl, aryl-$(C_1-C_6)$-alkyl, heteroaryl-$(C_1-C_6)$-alkyl, $(C_3-C_6)$-cycloalkyl, $(C_3-C_6)$-cycloalkyl-$(C_1-C_6)$-alkyl, $(C_3-C_6)$-halocycloalkyl, $(C_3-C_6)$-halocycloalkyl-$(C_1-C_4)$-alkyl, $(C_2-C_8)$-alkenyl, $(C_2-C_8)$-alkynyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, $(C_1-C_8)$-alkylcarbonyl, $(C_1-C_8)$-haloalkylcarbonyl, $(C_3-C_8)$-cycloalkylcarbonyl, formyl, $(C_1-C_8)$-alkoxycarbonyl, $(C_1-C_8)$-haloalkoxycarbonyl, $(C_3-C_8)$-cycloalkoxycarbonyl, $(C_1-C_8)$-alkylaminocarbonyl, $(C_2-C_8)$-dialkylaminocarbonyl, $(C_3-C_8)$-cycloalkylaminocarbonyl, and $R^5$ is hydrogen, halogen, cyano, nitro, formyl, $(C_1-C_8)$-alkyl, $(C_1-C_8)$-haloalkyl, $(C_2-C_8)$-alkenyl, $(C_2-C_8)$-alkynyl, $(C_2-C_8)$-haloalkenyl, $(C_2-C_8)$-haloalkynyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, $(C_1-C_8)$-alkylcarbonyl, $(C_1-C_8)$-haloalkylcarbonyl, $(C_3-C_8)$-cycloalkylcarbonyl, carboxyl, $(C_1-C_8)$-alkoxycarbonyl, $(C_1-C_8)$-haloalkoxycarbonyl, $(C_3-C_8)$-cycloalkoxycarbonyl, $(C_1-C_8)$-alkylaminocarbonyl, $(C_2-C_8)$-dialkylaminocarbonyl, $(C_3-C_8)$-cycloalkylaminocarbonyl, hydroxy, $(C_1-C_8)$-alkoxy, $(C_1-C_8)$-haloalkoxy, $(C_1-C_8)$-alkylthio, $(C_1-C_8)$-haloalkylthio, $(C_3-C_8)$-cycloalkylthio, $(C_1-C_8)$-alkylsulfinyl, $(C_1-C_8)$-haloalkylsulfinyl, $(C_3-C_8)$-cycloalkylsulfinyl, $(C_1-C_8)$-alkylsulfonyl, $(C_1-C_8)$-haloalkylsulfonyl, $(C_3-C_8)$-cycloalkylsulfonyl, $(C_1-C_8)$-alkylaminosulfonyl, $(C_2-C_8)$-dialkylaminosulfonyl or $(C_3-C_8)$-trialkylsilyl, wherein the compound of formula (I) does not comprise:
2-(2-phenoxyphenylamino)pyridine;
5-bromo-2-(2-phenoxyphenylamino)pyridine;
5-chloro-2-(2-phenoxyphenylamino)pyridine;
2-(2-phenoxyphenylamino)pyrimidine;
5-bromo-2-(2-phenoxyphenylamino)pyrimidine;
5-iodo-2-(2-phenoxyphenylamino)pyrimidine;
2-(2-(2-pyridyloxy)phenylamino)pyridine; and
3-bromo-2-(2-phenoxyphenylamino)pyridine.

2. The compound of formula (I) of claim 1, or a salt thereof, wherein:

A is nitrogen or —CX—,

X is hydrogen, fluorine or chlorine, $R^1$ is an optionally substituted phenyl, pyridyl or pyrimidyl, where each ring or each ring system is optionally substituted by up to 5 substituents independently selected from the group $R^5$, each $R^2$ is independently halogen, cyano, nitro, $(C_1-C_4)$-alkyl, $(C_1-C_4)$-haloalkyl, $NR^4R^6$, $(C_1-C_4)$-alkoxycarbonyl, $(C_1-C_4)$-alkylthio or $(C_1-C_4)$-alkoxy, m is 0, 1, 2 or 3, $R^3$ is hydrogen, halogen, cyano, nitro, $(C_1-C_4)$-alkyl, $(C_1-C_4)$-haloalkyl, $(C_2-C_4)$-alkenyl, $(C_2-C_4)$-alkynyl, $(C_2-C_4)$-haloalkenyl, $(C_2-C_4)$-haloalkynyl, cyclpropyl, cyclopropylmethyl, $(C_1-C_4)$-alkoxy, $(C_1-C_4)$-haloalkoxy, $(C_1-C_4)$-alkylthio or $(C_1-C_4)$-haloalkylthio, $R^4$ and $R^6$ are independently hydrogen, $(C_1-C_4)$-alkyl, $(C_1-C_4)$-alkylcarbonyl or $(C_1-C_4)$-alkoxycarbonyl, and $R^5$ is hydrogen, halogen, cyano, $(C_1-C_4)$-alkyl, $(C_1-C_4)$-haloalkyl, $(C_1-C_4)$-alkylthio, $(C_1-C_4)$-alkoxy or $(C_1-C_4)$-haloalkoxy, wherein the compound of formula (I) does not comprise:
2-(2-phenoxyphenylamino)pyridine;
5-bromo-2-(2-phenoxyphenylamino)pyridine;
5-chloro-2-(2-phenoxyphenylamino)pyridine;
2-(2-phenoxyphenylamino)pyrimidine;
5-bromo-2-(2-phenoxyphenylamino)pyrimidine;
5-iodo-2-(2-phenoxyphenylamino)pyrimidine;
2-(2-(2-pyridyloxy)phenylamino)pyridine; and
3-bromo-2-(2-phenoxyphenylamino)pyridine.

3. The compound of formula (I) of claim 1, or a salt thereof, wherein:

A is nitrogen or —CX—,

X is hydrogen, fluorine or chlorine, $R^1$ is an optionally substituted phenyl, pyridyl or pyrimidyl, where each ring is optionally substituted by up to 5 substituents independently of one another selected from the group $R^5$, each $R^2$ is independently fluorine, chlorine, bromine, cyano, nitro, methyl, ethyl, trifluoromethyl, methoxy, methylthio or amino, m is 0, 1, 2 or 3, $R^3$ is hydrogen, fluorine, chlorine, bromine, cyano, nitro, methyl, ethyl, trifluoromethyl, methoxy, trifluoromethoxy, methylthio or trifluoromethylthio, and $R^5$ is hydrogen, fluorine, chlorine, bromine, cyano, methyl, trifluoromethyl, methoxy or trifluoromethoxy, wherein the compound of formula (I) does not comprise:
2-(2-phenoxyphenylamino)pyridine;
5-bromo-2-(2-phenoxyphenylamino)pyridine;
5-chloro-2-(2-phenoxyphenylamino)pyridine;
2-(2-phenoxyphenylamino)pyrimidine;
5-bromo-2-(2-phenoxyphenylamino)pyrimidine;
5-iodo-2-(2-phenoxyphenylamino)pyrimidine;
2-(2-(2-pyridyloxy)phenylamino)pyridine; and
3-bromo-2-(2-phenoxyphenylamino)pyridine.

4. A herbicidal composition, comprising a herbicidally active amount of at least one compound of formula (I) according to claim 1.

5. The herbicidal composition of claim 4, wherein the at least one compound of formula (I) is in a mixture with formulation auxiliaries.

6. The herbicidal composition of claim 4, further comprising at least one additional pesticidally active substance selected from the group consisting of insecticides, acaricides, herbicides, fungicides, safeners, and growth regulators.

7. The herbicidal composition of claim 6, comprising a safener.

8. The herbicidal composition of claim 7, comprising 6, wherein the composition comprises at least one safener selected from the group consisting of cyprosulfamide, cloquintocet-mexyl, mefenpyr-diethyl and isoxadifen-ethyl.

9. The herbicidal composition of claim 4, further comprising an additional further herbicide.

10. A method of controlling unwanted plants, comprising applying a herbicidally effective amount of at least one compound of formula (I) according to claim 1, to the plants or to the site of the unwanted plants.

11. A method of controlling unwanted plants, comprising applying a herbicidally effective amount of the herbicidal composition according to claim 4, to the plants or to the site of the unwanted plants.

12. The method of claim 11, wherein the herbicidal composition is used for controlling unwanted plants in crops of useful plants.

13. The method of claim 12, wherein the useful plants are transgenic useful plants.

14. The herbicidal composition of claim 5, further comprising at least one additional pesticidally active substance selected from the group consisting of insecticides, acaricides, herbicides, fungicides, safeners, and growth regulators.

15. The method of claim 10, wherein the herbicidal composition is used for controlling unwanted plants in groups of useful plants.

16. The method of claim 15, wherein the useful plants are transgenic useful plants.

17. A compound of formula (I) or a salt thereof,

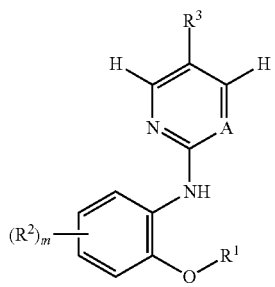

(I)

wherein:
A is nitrogen or —CX—,
X is hydrogen, fluorine or chlorine,
$R^1$ is an optionally substituted aryl or heteroaryl, where each ring or each ring system is optionally substituted by up to 5 substituents independently selected from the group $R^5$,
each $R^2$ is independently halogen, cyano, nitro, formyl, formamide, $(C_1-C_8)$-alkyl, $(C_1-C_8)$-haloalkyl, $(C_2-C_8)$-alkenyl, $(C_2-C_8)$-alkynyl, $(C_2-C_8)$-haloalkenyl, $(C_2-C_8)$-haloalkynyl, $(C_3-C_8)$-cycloalkyl, $(C_3-C_6)$-halocycloalkyl, $(C_3-C_6)$-cycloalkyl-$(C_1-C_6)$-alkyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, $(C_1-C_8)$-alkylcarbonyl, $(C_1-C_8)$-haloalkylcarbonyl, $(C_3-C_8)$-cycloalkylcarbonyl, carboxyl, $(C_1-C_8)$-alkoxycarbonyl, $(C_1-C_8)$-haloalkoxycarbonyl, $(C_3-C_8)$-cycloalkoxycarbonyl, carbamoyl, $(C_2-C_8)$-alkylaminocarbonyl, $(C_2-C_{10})$-dialkylaminocarbonyl, $(C_3-C_{10})$-cycloalkylaminocarbonyl, $(C_1-C_4)$-alkoxycarbonyl-$(C_1-C_4)$-alkyl, $(C_1-C_4)$-haloalkoxycarbonyl-$(C_1-C_4)$-alkyl, carboxy-$(C_1-C_4)$-alkyl, hydroxy, $NR^4R^6$, $(C_1-C_8)$-alkoxy, $(C_1-C_8)$-haloalkoxy, $(C_1-C_8)$-alkylthio, $(C_1-C_8)$-haloalkylthio, $(C_3-C_8)$-cycloalkylthio, $(C_1-C_4)$-alkoxy-$(C_1-C_4)$-alkylthio, $(C_1-C_8)$-alkylsulfinyl, $(C_1-C_8)$-haloalkylsulfinyl, $(C_3-C_8)$-cycloalkylsulfinyl, $(C_1-C_4)$-alkoxy-$(C_1-C_4)$-alkylsulfinyl, $(C_1-C_8)$-alkylsulfonyl, $(C_1-C_8)$-haloalkylsulfonyl, $(C_3-C_8)$-cycloalkylsulfonyl, $(C_1-C_4)$-alkoxy-$(C_1-C_4)$-alkylsulfonyl, $(C_1-C_8)$-alkylaminosulfonyl, $(C_2-C_8)$-dialkylaminosulfonyl or $(C_3-C_8)$-trialkylsilyl, m is 0, 1, 2 or 3, $R^3$ is hydrogen, halogen, cyano, nitro, $(C_1-C_8)$-alkyl, $(C_1-C_8)$-haloalkyl, $(C_2-C_4)$-alkenyl, $(C_2-C_4)$-alkynyl, $(C_3-C_6)$-cycloalkyl, $(C_3-C_6)$-cycloalkyl-$(C_1-C_6)$-alkyl, $(C_1-C_8)$-alkoxy, $(C_1-C_8)$-haloalkoxy, $(C_1-C_8)$-alkylthio, $(C_1-C_8)$-haloalkylthio, $(C_1-C_8)$-alkylsulfinyl, $(C_1-C_8)$-haloalkylsulfinyl, $(C_1-C_8)$-alkylsulfonyl, $(C_1-C_8)$-haloalkylsulfonyl, $R^4$ and $R^6$ are independently hydrogen, $(C_1-C_8)$-alkyl, $(C_1-C_8)$-haloalkyl, aryl-$(C_1-C_6)$-alkyl, heteroaryl-$(C_1-C_6)$-alkyl, $(C_3-C_6)$-cycloalkyl, $(C_3-C_6)$-cycloalkyl-$(C_1-C_6)$-alkyl, $(C_3-C_6)$-halocycloalkyl, $(C_3-C_6)$-halocycloalkyl-$(C_1-C_4)$-alkyl, $(C_2-C_8)$-alkenyl, $(C_2-C_8)$-alkynyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, $(C_1-C_8)$-alkylcarbonyl, $(C_1-C_8)$-haloalkylcarbonyl, $(C_3-C_8)$-cycloalkylcarbonyl, formyl, $(C_1-C_8)$-alkoxycarbonyl, $(C_1-C_8)$-haloalkoxycarbonyl, $(C_3-C_8)$-cycloalkoxycarbonyl, $(C_1-C_8)$-alkylaminocarbonyl, $(C_2-C_8)$-dialkylaminocarbonyl, $(C_3-C_8)$-cycloalkylaminocarbonyl, and $R^5$ is hydrogen, halogen, cyano, nitro, formyl, $(C_1-C_8)$-alkyl, $(C_1-C_8)$-haloalkyl, $(C_2-C_8)$-alkenyl, $(C_2-C_8)$-alkynyl, $(C_2-C_8)$-haloalkenyl, $(C_2-C_8)$-haloalkynyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, $(C_1-C_8)$-alkylcarbonyl, $(C_1-C_8)$-haloalkylcarbonyl, $(C_3-C_8)$-cycloalkylcarbonyl, carboxyl, $(C_1-C_8)$-alkoxycarbonyl, $(C_1-C_8)$-haloalkoxycarbonyl, $(C_3-C_8)$-cycloalkoxycarbonyl, $(C_1-C_8)$-alkylaminocarbonyl, $(C_2-C_8)$-dialkylaminocarbonyl, $(C_3-C_8)$-cycloalkylaminocarbonyl, hydroxy, $(C_1-C_8)$-alkoxy, $(C_1-C_8)$-haloalkoxy, $(C_1-C_8)$-alkylthio, $(C_1-C_8)$-haloalkylthio, $(C_3-C_8)$-cycloalkylthio, $(C_1-C_8)$-alkylsulfinyl, $(C_1-C_8)$-haloalkylsulfinyl, $(C_3-C_8)$-cycloalkylsulfinyl, $(C_1-C_8)$-alkylsulfonyl, $(C_1-C_8)$-haloalkylsulfonyl, $(C_3-C_8)$-cycloalkylsulfonyl, $(C_1-C_8)$-alkylaminosulfonyl, $(C_2-C_8)$-dialkylaminosulfonyl or $(C_3-C_8)$-trialkylsilyl, wherein the compound of formula (I) does not comprise:
2-(2-phenoxyphenylamino)pyridine;
5-bromo-2-(2-phenoxyphenylamino)pyridine;
5-chloro-2-(2-phenoxyphenylamino)pyridine;
2-(2-phenoxyphenylamino)pyrimidine;
5-bromo-2-(2-phenoxyphenylamino)pyrimidine;
5-iodo-2-(2-phenoxyphenylamino)pyrimidine; and
2-(2-(2-pyridyloxy)phenylamino)pyridine.

18. The compound of formula (I) of claim 17, or a salt thereof, wherein:
A is nitrogen or —CX—,
X is hydrogen, fluorine or chlorine,
$R^1$ is an optionally substituted phenyl, pyridyl or pyrimidyl, where each ring or each ring system is optionally substituted by up to 5 substituents independently selected from the group $R^5$,
each $R^2$ is independently halogen, cyano, nitro, $(C_1-C_4)$-alkyl, $(C_1-C_4)$-haloalkyl, $NR^4R^6$, $(C_1-C_4)$-alkoxycarbonyl, $(C_1-C_4)$-alkylthio or $(C_1-C_4)$-alkoxy, m is 0, 1, 2 or 3, $R^3$ is hydrogen, halogen, cyano, nitro, $(C_1$-$C_4)$-alkyl, $(C_1$-$C_4)$-haloalkyl, $(C_2$-$C_4)$-alkenyl, $(C_2$-$C_4)$-alkynyl, $(C_2$-$C_4)$-haloalkenyl, $(C_2$-$C_4)$-haloalkynyl, cyclpropyl, cyclopropylmethyl, $(C_1$-$C_4)$-alkoxy, $(C_1$-$C_4)$-haloalkoxy, $(C_1$-$C_4)$-alkylthio or $(C_1$-$C_4)$-haloalkylthio, $R^4$ and $R^6$ are independently hydrogen, $(C_1$-$C_4)$-alkyl, $(C_1$-$C_4)$-alkylcarbonyl or $(C_1$-$C_4)$-alkoxycarbonyl, and $R^5$ is hydrogen, halogen, cyano, $(C_1$-$C_4)$-alkyl, $(C_1$-$C_4)$-haloalkyl, $(C_1$-$C_4)$-alkylthio, $(C_1$-$C_4)$-alkoxy or $(C_1$-$C_4)$-haloalkoxy, wherein the compound of formula (I) does not comprise:

2-(2-phenoxyphenylamino)pyridine;
5-bromo-2-(2-phenoxyphenylamino)pyridine;
5-chloro-2-(2-phenoxyphenylamino)pyridine;
2-(2-phenoxyphenylamino)pyrimidine;
5-bromo-2-(2-phenoxyphenylamino)pyrimidine;
5-iodo-2-(2-phenoxyphenylamino)pyrimidine; and
2-(2-(2-pyridyloxy)phenylamino)pyridine.

19. The compound of formula (I) of claim 17, or a salt thereof, wherein:

A is nitrogen or —CX—,

X is hydrogen, fluorine or chlorine, $R^1$ is an optionally substituted phenyl, pyridyl or pyrimidyl, where each ring is optionally substituted by up to 5 substituents independently of one another selected from the group $R^5$, each $R^2$ is independently fluorine, chlorine, bromine, cyano, nitro, methyl, ethyl, trifluoromethyl, methoxy, methylthio or amino, m is 0, 1, 2 or 3, $R^3$ is hydrogen, fluorine, chlorine, bromine, cyano, nitro, methyl, ethyl, trifluoromethyl, methoxy, trifluoromethoxy, methylthio or trifluoromethylthio, and $R^5$ is hydrogen, fluorine, chlorine, bromine, cyano, methyl, trifluoromethyl, methoxy or trifluoromethoxy, wherein the compound of formula (I) does not comprise:

2-(2-phenoxyphenylamino)pyridine;
5-bromo-2-(2-phenoxyphenylamino)pyridine;
5-chloro-2-(2-phenoxyphenylamino)pyridine;
2-(2-phenoxyphenylamino)pyrimidine;
5-bromo-2-(2-phenoxyphenylamino)pyrimidine;
5-iodo-2-(2-phenoxyphenylamino)pyrimidine; and
2-(2-(2-pyridyloxy)phenylamino)pyridine.

20. A method of controlling unwanted plants, comprising applying a herbicidal composition comprising an herbicidally effective amount of at least one compound of formula (I) according to claim 17, to the plants or to the site of the unwanted plants.

* * * * *